(12) United States Patent
Jack et al.

(10) Patent No.: US 6,399,578 B1
(45) Date of Patent: Jun. 4, 2002

(54) CONJUGATES COMPRISING GALACTOSE α1,3 GALACTOSYL EPITOPES AND METHODS OF USING SAME

(75) Inventors: Richard M. Jack, Del Mar; David S. Jones; Lin Yu, both of San Diego, all of CA (US)

(73) Assignee: La Jolla Pharmaceutical Company, San Diego, CA (US)

( * ) Notice: Subject to any disclaimer, the term of this patent is extended or adjusted under 35 U.S.C. 154(b) by 0 days.

(21) Appl. No.: 09/457,913

(22) Filed: Dec. 8, 1999

Related U.S. Application Data

(60) Provisional application No. 60/160,997, filed on Oct. 23, 1999, and provisional application No. 60/111,644, filed on Dec. 9, 1998.

(51) Int. Cl.$^7$ .............................................. A01N 43/04
(52) U.S. Cl. ....................... 514/25; 536/17.4; 536/17.6
(58) Field of Search ...................... 435/7.94; 436/536, 436/815, 822; 514/53, 25; 536/17.4, 17.6

(56) References Cited

U.S. PATENT DOCUMENTS

| | | |
|---|---|---|
| 4,086,924 A | 5/1978 | Latham, Jr. |
| 4,191,668 A | 3/1980 | Katz |
| 4,223,672 A | 9/1980 | Terman et al. |
| 4,751,181 A | 6/1988 | Keene |

(List continued on next page.)

FOREIGN PATENT DOCUMENTS

| | | | |
|---|---|---|---|
| EP | 0 438 259 A1 B1 | 7/1991 | |
| EP | 0 442 724 A2 B1 | 8/1991 | |
| EP | 0 523 978 A1 | 1/1993 | |
| EP | 642798 A2 | * 3/1995 | |

(List continued on next page.)

OTHER PUBLICATIONS

Auchincloss et al. (1998) "Xenogeneic transplantation" *Ann. Rev. Immunol.* 16:433–470.
Bach et al. (1995) "Barries to xenotransplantation" *Nature Med.* 1:869–873.
Borel et al. (1990) "A novel technique to link either proteins or peptides to gammaglobulin to construct tolerogens" *J. Immunol. Methods* 126:159–168.
Borel et al. (1995) "Food allergens transformed into tolerogens" *Int. Arch. Allergy Immunol.* 107:264–267.
Borel et al. (1996) "Parenteral and oral administration of tolerogens: Protein–IgG conjugates" *Ann. N.Y. Acad. Sci.* 778:80–87.
Byrne et al. (1997) "Transgenic pigs expressing human CD59 and decay–accelerating factor produce an intrinsic barrier to complement–mediated damage" *Transplantation* 63:149–155.
Christie et al. (1993) "Treatment of refractoriness to platelet transfusion by protein A column therapy" *Transfusion* 33:234–242.
Cooper et al. (1996) "Manipulation of the anti–αGal antibody–αGal epitope system in experimental discordant xenotransplantation" *Xenotransplantation* 3:102–111.
Cooper et al. (1998) "Xenoantigens and xenoantibodies" *Xenotransplantation* 5:6–17.

(List continued on next page.)

*Primary Examiner*—Mary E. Ceperley
(74) *Attorney, Agent, or Firm*—Morrison & Foerster LLP

(57) ABSTRACT

This invention provides conjugates useful for xenotransplantation which comprise a galactose α1,3 galactosyl (αGal) epitope conjugated to a valency platform molecule, preferably a chemically defined valency platform molecule which allows precise valency. The invention also provides compositions comprising these conjugates, and methods (such as methods for inducing tolerance) using these conjugates and compositions.

22 Claims, 34 Drawing Sheets

Octomeric Conjugate:

U.S. PATENT DOCUMENTS

| | | | |
|---|---|---|---|
| 5,126,131 A | 6/1992 | Dintzis et al. |
| 5,162,515 A | 11/1992 | Conrad et al. |
| 5,268,454 A | 12/1993 | Barstad et al. |
| 5,276,013 A | 1/1994 | Conrad et al. |
| 5,391,785 A | 2/1995 | Jones et al. |
| 5,552,391 A | 9/1996 | Coutts et al. |
| 5,606,047 A | 2/1997 | Coutts et al. |
| 5,663,395 A | 9/1997 | Göbel et al. |
| 5,726,329 A | 3/1998 | Jones et al. |
| 5,733,254 A | 3/1998 | Jones et al. |
| 5,786,512 A | 7/1998 | Jones et al. |
| 5,874,409 A | 2/1999 | Victoria et al. |
| 6,022,544 A | 2/2000 | Dintzis et al. |
| 6,060,056 A | 5/2000 | Coutts et al. |

FOREIGN PATENT DOCUMENTS

| | | |
|---|---|---|
| WO | WO 87/00056 A1 | 1/1987 |
| WO | WO 88/09810 A1 | 12/1988 |
| WO | WO 91/10426 | 7/1991 |
| WO | WO 92/13558 | 8/1992 |
| WO | WO 93/02093 A1 | 2/1993 |
| WO | WO 93/03735 | 3/1993 |
| WO | WO 94/21799 | 9/1994 |
| WO | WO 95/07073 | 3/1995 |
| WO | WO 95/20661 | 8/1995 |
| WO | WO 96/40197 | 12/1996 |
| WO | WO 97/11963 | 4/1997 |
| WO | WO 97/16064 | 5/1997 |
| WO | WO 97/46251 | 12/1997 |
| WO | WO 98/03653 | 1/1998 |
| WO | WO 98/33528 | 8/1998 |
| WO | WO 98/47915 | 10/1998 |
| WO | WO 99/52561 | 10/1999 |
| WO | WO 99/64595 | 12/1999 |
| WO | WO 00/34296 | 6/2000 |

OTHER PUBLICATIONS

Dumas et al. (1995) "Induction of tolerance by administration of hapten–immunoglobulin conjugates is associated with decreased IL–2 and IL–4 production" *Arch. Dematol. Res.* 287:123–128.

Galili et al. (1997) "Porcine and bovine cartilage transplants in cynomolgus monkey" *Transplantation* 63:646–651.

Galili et al. (1998) "Man, apes, and old world monkeys differ from other mammals in the expression of α–galactosyl epitopes on nucleated cells" *J. Biol. Chem.* 263:17755–17762.

Galili et al. (1995) "Increased anti–gal activity in diabetic patients transplanted with fetal porcine islet cell clusters" *Transplantation* 59:1549–1556.

Galili et al. (1998) "Anti–gal antibody prevents xenotransplantation" *Science and Medicine* 5:28–37.

Galili et al. (1985) "Human natural anti–α–galactosyl IgG" *J. Exp. Med.*162:573–582.

Kujundzic et al. (1994) "Variability of anti–αGal antibodies in human serum and their relation to serum cytotoxicity against pig cells" *Xenotransplantation* 1:58–65.

Li et al. (1995) "Inhibition of human anti–αGal IgG by oligosaccharides derived from porcine stomach mucin" *Xenotransplantation* 2:279–288.

Mahato et al. (1997) "Cationic lipid–based gene delivery systems: Pharmaceutical perspectives" *Pharm. Res.* 14:853–859.

McKane et al. (1998) "Polymorphism in the human anti–pig natural antibody repertoire" *Transplantation* 66:626–633.

McKenzie et al., (1998) "A murine model of antibody–mediated hyperacute rejection by galactose–α(1,3)galactose antibodies in Gal o/o mice" *Transplantation* 66:754–763.

Nildsson et al. (1981) "A procedure for removing high titer antibodies by extracorporeal protein–a–sepharose adsorption in hemophilia: Substitution therapy and surgery in a patient with hemophilia B and antibodies" *Blood* 58(1):38–44.

Nilsson, Kurt G. I. (1997) "Glycosidase–catalysed synthesis of di–and trisaccharide derivatives related to antigens involved in the hyperacute rejection of xenotransplants" *Tetrahedron Lett.* 38:133–136.

Oriol et al. (1997) "Major carbohydrate xenotransplantation antigens" Chapter 4 in *Xenotransplantation*, D.K.C. Copper et al. (Eds.), Springer–Verlag:New York, pp. 24–32.

Parker et al. (1994) "Characterization and affinity isolation of xenoreactive human natural antibodies" *J. Immunol.* 153:3791–3803.

Richter et al. (1993) "Three–year treatment of familial heterozygous hypercholesterolemia by extracorporeal low–density lipoprotein immunoadsorption with polyclonal apolipoprotein B antibodies" *Metabolism* 42:888–894.

Richter et al. (1997) "Efficacy and safety of immunoglobulin apheresis" *ASAIO J.* 43(1):53–59.

Sablinski et al. (1995) "Xenotransplantation of pig kidneys to nonhuman primates: I. Development of the model" *Xenotransplantation* 2:264–270.

Sandrin et al. (1993) "Anti–pig IgM antibodies in human serum react predominantly with Gal(α1–3) Gal epitopes" *Proc. Natl. Acad. Sci. USA* 90:11391–11395.

Schmoeckel et al. (1996) "Prevention of hyperacute rejection by human decay accelerating factor in xenogeneic perfused working hearts" *Transplantation* 62:729–734.

Soulillou, Jean–Paul (1998) "Xenotransplantation: Towards clinical practice. 4th Xenotransplantation Congress highlights" *Xenotransplantation* 5:2–5.

Suzuki et al. (1994) "Preferential adsorption of cationic anti–DNA antibodies with immobilized polyanionic compounds, dextran sulfate" *Autoimmunity* 19:105–112.

Tange et al. (1997) "Demostration of the functional importance of the Gal epitope in an ex vivo model of xenotransplantation" *Xenotransplantation* 4:20–24.

Thall et al. (1995) "Oocyte galα1,3gal epitopes implicated in sperm adhesion to the zona pellucida glycoprotein ZP3 are not required for fertilization in the mouse" *J. Biol. Chem.* 270:21437–21440.

Wallukat et al. (1996) "Removal for autoantibodies in dilated cardiomyopathy by immunoadsorption" *Int'l J. Card.* 54:191–195.

Wieslander et al. (1990) "Specificity of human antibodies against Galα1–3Gal carbohydrate epitope and distinction from natural antibodies reacting with Galα1–2Gal or Galα1–4Gal" *Glycoconjugate J.* 7:85–100.

Wünsch et al. (1982) "1–(tert–butylthio)–1,2–hydrazinedicarboxylic acid derivates" *Hoppe–Seyler's Z. Physiol. Chem.* 363:S.1461–1464.

Yang et al. (1998) "Tolerization of anti–Galα1–3Gal natural antibody–forming B cells by induction of mixed chimerism" *J. Exp. Med.* 187:1335–1342.

Efimov, V.A. et al. (1993). "Synthesis of Polyethylene Glycol–Oligonucleotide Conjugates," *Bioorg. Khim.*, 19(8):800–804 (English abstract on p. 804).

Hertler, A.A. (1988). "Human Immune Response to Immunotoxins," *Cancer Treatment Research* 37:475–480.

Jones, D.S. et al. (1994). "Conjugates of Double–Stranded Oligonucleotides with Poly(ethylene glycol) and Keyhole Limpet Hemocyanin: A Model for Treating Systemic Lupus Erythematosus," *Bioconjugate Chem.* 5:390–399.

Jones, D.S. et al. (1995). "Immunospecific Reduction of Antioligonucleotide Antibody–Forming Cells with a Tetrakis–oligonucleotide Conjugate (LJP 394), a Therapeutic Candidate for the Treatment of Lupus Nephritis," *J. Med. Chem.* 38:2138–2144.

Sehon, A.H. (1991). "Suppression of Antibody Responses by Conjugates of Antigens and Monomethypoly(Ethylene Glycol)," *Advanced Drug Delivery Reviews* 6:203–217.

Jia, L. et al. (2001). "Biostability and Pharmacokinetics of LJP 920, and Octameric Gal ($\alpha$1–3) Gal Conjugate for the Inhibition of Xenotransplantation Rejection," *J. Pharmacy and Pharmacology* 53(7):999–1005.

* cited by examiner

General Conjugation Chemistry

Method 1:

Method 2:

R = H, tBUS, or COCH₃
X = I, Br, or Cl

General Conjugation Chemistry

Method 3:

Dimeric Platform:

23

24

Tetrameric Platform:

26

25

28

27

Monomeric Conjugate:

33

Dimeric Conjugate:

34

35

36

Tetrameric Conjugate:

37

38

Tetrameric Conjugate:

Octomeric Conjugate:

Octomeric Conjugate:

Octomeric Conjugate:

Octomeric Conjugate:

CONJUGATES COMPRISING GALACTOSE α1,3 GALACTOSYL EPITOPES AND METHODS OF USING SAME

CROSS REFERENCE TO RELATED APPLICATIONS

This application claims the priority benefit of provisional applications U.S. Ser. No. 60/111,644, filed Dec. 9, 1998, and U.S. Pat. No. 60/160,997, filed Oct. 23, 1999, the contents of both of which are incorporated by reference in their entirety.

STATEMENT OF RIGHTS TO INVENTIONS MADE UNDER FEDERALLY SPONSORED RESEARCH (Not applicable)

TECHNICAL FIELD

This invention relates to the field of xenotransplanation and immunotolerance. More specifically, it relates to conjugates of galactose α1,3 galactosyl epitope(s) (αGal) for use in reducing levels of circulating anti-αGal antibodies and inducing immune tolerance to xenotransplanted tissue.

BACKGROUND

There is a large and increasing need for organ transplantation, which is exacerbated by a critical shortage of available human organs for transplant. The possibility of employing xenotransplantation to overcome the lack of human organs for allotransplantation is a possible solution to the critical organ shortage but in itself presents serious problems.

Two basic types of xenografts have been studied. In concordant xenografts, an organ from a donor animal is transplanted into a similar species which lacks antibodies to the donor organ. Rejection of a concordant organ is usually caused by T cell-mediated reactivity to differences in major histocompatability antigens. Concordant xenotransplantation had been applied to human patients as early as 1963 with the most celebrated case being the transplantation of a baboon heart into a human neonate. Auchincloss et al. (1998) *Ann. Rev. Immunol.* 16:433. In discordant transplants, the donor and recipient are phylogenetically more distant and the recipient has antibodies to the donor organ as is the case of porcine organs transplanted into Old World primates. These xenografts are rejected within the first few minutes due to the phenomenon of hyperacute rejection (HAR).

In humans and Old World primates, natural antibodies specific for the galactose α1,3 galactosyl (αGal) epitope mediate both the hyperacute rejection (HAR) and delayed xenograft rejection (DXR) of organs xenotransplanted from animals such as pigs. Humans and Old World primates express high levels of circulating antibodies to galactose α1,3 galactosyl (αGal) residues which are expressed at high levels on membrane lipids and proteins of other animal species. Galili et al. (1988) *J. Biol. Chem.* 263:17755. This is due to the fact that humans and Old World primates lack the enzyme α1,3 galactosyltransferase which is required to express the αGal epitope (Sandrin et al. (1993) *Proc. Natl. Acad. Sci. USA* 90:11391) and thus make antibodies to the αGal epitope which is expressed on normal gut flora and is recognized as foreign. By contrast, xenograft organ donor species (e.g., pigs) express the α1,3 galactosyltransferase enzyme and thus express the αGal epitope. It has been estimated that there are approximately $10^7$ αGal epitopes per cell on many donor tissue cells. Cooper et al. (1998) *Xenotransplantation* 5:6–17.

When an αGal-expressing discordant organ is transplanted into a recipient that produces anti-αGal antibodies, the first deleterious result is HAR mediated by the high levels (up to 4% of circulating IgM) of the natural anti-αGal Ig. Parker (1994) *J. Immunol.* 153:3791. αGal bearing transplants (porcine islets) into humans have been shown to increase anti-αGal responses by up to 64-fold. Galili et al. (1995) *Transplantation* 59:1549. Transplantation of pig cartilage into cynomolgus monkeys causes a 30–300 fold increase in IgG anti-αGal and 2–16 fold increase in IgM. Galili et al. (1997) *Transplantation* 63:646. These natural antibodies bind to αGal expressed on the endothelial surfaces of the engrafted organ which both activates the complement system and the endothelium causing damage to the cell and sets up a net prothrombotic state on the vessel surface. The result is a damaged endothelium and massive clotting causing the rapid development of ischemia of the transplanted organ and its functional incapacitation within minutes to hours.

Anti-αGal antibodies also play a role in delayed xenograft rejection (DXR), the intermediate term (several days) damage to xenotransplanted organs which often results in rejection. Bach et al. (1995) *Nature Med.* 1:869–873. Anti-αGal antibodies bind to the endothelium and mediate a plethora of cell-mediated responses such as ADCC, leading to vascular and tissue damage which compromises the function of the transplanted organ. Anti-αGal antibodies can also cause chronic activation of receptors on xenograft cells and/or increased immunogenicity of xenograft-specific antigens. Cooper et al. (1998) *Xenotransplantation* 5:6–17. Diminution of anti-αGal antibodies levels can attenuate this damage, but the damage, even if not acute, is cumulative and can eventually leads to organ rejection.

Various strategies have been pursued to deal with the major sequelae of anti-αGal antibody binding. These include: 1) inhibition of effector functions mediated, directly or indirectly by anti-αGal antibodies; 2) depletion of recipient anti-αGal antibodies; 3) sublethal irradiation and reconstitution of recipient with autologous and donor bone marrow; 4) modification of donor tissue glycosylation; 5) suppression of anti-αGal antibodies in recipient; and 6) administration of αGal moieties found on donor tissue to the recipient.

In attempts to inhibit the effector functions mediated by anti-αGal antibody binding, much effort has been spent to generate donor animals transgenic for complement regulatory proteins such as decay accelerating factor (DAF, CD55), and homologous restriction factor (HRF, CD59). Schmoekel et al. (1996) Transplantation 62:729; and Byrne et al. (1997) *Transplantation* 63:149. These proteins, members of the regulators of complement activation (RCA) gene family, can downregulate the generation of complement proteins which mediate acute inflammation and cell lytic activity. Transgenic expression of RCA proteins does nothing, however, to address the effect of anti-αGal antibodies binding to the endothelium which sets up the net prothrombotic state subsequent to endothelial cell activation. Thus, while RCA-transgenic donor organs may have an ameliorative effect on HAR, this approach will not have an effect on DXR wherein xenograft damage is mediated by effector cells which bind to anti-αGal antibodies. Further, while the expression of RCA molecules on the transplanted organ may protect the transplant from protective functions of the host/recipient immune response, if the transplanted organ were to express pathogen antigens (from viral or bacterial infection), protective antibody effector function mediated by complement would be effectively shut off leaving the host with an organ full of pathogen-infected cells. For these reasons, strategies aimed at controlling complement are thought to be insufficient to achieve long-term graft survival unless acceptable regimens are developed to reduce antibody responses. Soulillou (1998) *Xenotransplantation* 5:1–2.

Depleting the recipient of pathogenic anti-αGal antibodies has been shown to prolong pig organ survival. Cooper et al. (1996) *Xenotransplantation* 4:27. However, attempts to remove the natural anti-αGal antibodies by apheresis have been only temporarily effective and result in an only slightly delayed antibody-mediated organ rejection. Pathogenic levels of anti-αGal antibodies return within 1–2 days and mediate xenograft damage. Sablinski et al. (1995) *Xenotransplantation* 2:264; Cooper et al. (1998) *Xenotransplantation* 5:6. Thus, very frequent ex vivo plasmapheresis to reduce the incidence of HAR would be required. Furthermore, the cumulative damage by levels of anti-αGal antibodies too low to mediate HAR but which mediate DXR are unavoidable using the plasmapheresis strategy. In addition, currently available pharmacological interventions, even in combination, only have modest effect in inhibiting anti-αGal antibody production. Cooper et al. (1998) *Xenotransplantation* 5:6. Thus, it seems unlikely that permanent suppression of anti-αGal responses will be possible using this approach.

The use of mixed chimerism, wherein human organ recipients would be sublethally irradiated and reconstituted with autologous and porcine bone marrow, has been contemplated. αGal transferase knock out mice which do not express αGal have been tolerized via mixed hematopoietic chimerism. Thall et al. (1998) *J. Exp. Med.* However, instituting microchimerism of porcine marrow cells in primates would be problematic since primate marrow does not have the requisite species-specific hematopoietic cytokines/growth factors to facilitate their engraftment in the primate marrow.

Attempts to modify glycosylation of donor tissue, such as pig vascular endothelium have also been contemplated. However, pig knockouts (KO) created to effect the glycosylation modifications have not yet been accomplished due to a lack of porcine embryonic stem cells. Homologous recombination leading to the elimination of the α1,3 galactosyl transferase enzyme which leads to the expression of the αGal moiety has been accomplished in mice. Thall et al. (1995) *J. Biol. Chem.* 270:21437. αGal knock-out hearts still undergo rapid rejection when perfused with human plasma in ex vivo systems indicating that decreasing αGal production may increase other xenoantigens such as the Forssman antigen. Tange et al. (1997) *Xenotransplantation* 4:20. In addition, extreme modifications of carbohydrate antigen expression on cell surfaces may have a detrimental effect on development and differentiation. Attempts to decrease αgal expression by making animals transgenic for a fucosyl transferase does not sufficiently decrease antigen expression. Galili et al. (1998) *Science and Medicine* 9:28. Thus, the general approach of modifying αGal expression, while theoretically appealing, may be untenable.

PCT application WO 98US2103 generally describes αGal compositions for inducing tolerance. French patent application FR 2751346 (based on WO 9803653) describes transgenic cells for transplantation which contain polynucleotides which encode antibodies directed against molecules involved in rejection. PCT application WO 9716064 describes transgenic cells which express a functional carbohydrate epitope modifying gene product which modifies a cell surface carbohydrate epitope such as αGal. See also PCT WO 950661 (nucleic acid sequences encoding α1,3-galactosyltransferase) and PCT WO 9421799 (nucleic acid sequences encoding α1,3-galactosyltransferase).

In sum, in humans and Old World primates, natural antibodies specific for the galactose α1,3 galactosyl (αGal) epitope mediate both the hyperacute rejection (HAR) and delayed xenograft rejection (DXR) of organs xenotransplanted from animals such as pigs. Anti-αGal-mediated complement activation and endothelial cell activation induce an acute net procoagulant state on the endothelium of the engrafted organ leading to rapid clotting, ischemia and loss of organ function. Attempts to remove the natural anti-αGal antibodies have been only temporarily effective and result in an only slightly delayed antibody-mediated organ rejection.

There is a serious need to develop compositions (such as toleragens) and methods that counteract the effect of circulating αGal antibodies in order to promote effectiveness of xenotransplantation.

All publications cited herein are hereby incorporated by reference in their entirety.

SUMMARY OF THE INVENTION

We have discovered αGal conjugates with significantly increased ability to bind to anti-αGal antibodies, including IgM antibodies, which are the major effector molecules of hyperacute rejection. The invention thus provides these conjugates, compositions comprising these conjugates, and methods using these conjugates.

Accordingly, in one aspect, the invention provides a conjugate comprising a valency platform molecule and an αGal epitope, wherein the valency platform molecule has a valency between two and 128. Preferred embodiments include valency platform molecules with a valency of two, four, six, eight, ten, twelve, sixteen, twenty, and twenty-five. The αGal epitope may be any moiety which specifically binds to an anti-αGal antibody.

In another aspect, the invention provides a conjugate comprising a valency platform molecule and an αGal epitope, wherein the valency platform molecule has a valency of at least two, four, six, eight, ten, 12, 16, 20, and 25. The αGal epitope may be any moiety which specifically binds to an anti-αGal antibody.

In another aspect, the invention provides compositions comprising the conjugates described herein, and preferably contain an effective amount of any of the conjugates described herein. In some embodiments, the compositions comprise a pharmaceutical excipient.

In another aspect, the invention provides methods of reducing circulating levels of anti-αGal antibodies in an individual, comprising administering an effective amount any of the conjugates described herein to the individual, wherein an effective amount is an amount sufficient to reduce the circulating levels of anti-αGal antibodies.

In another aspect, the invention provides methods of neutralizing circulating levels of anti-αGal antibodies in an individual, comprising administering an effective amount of any of the conjugates described herein to the individual, wherein an effective amount is an amount sufficient to neutralize circulating levels of anti-αGal antibodies.

In another aspect, the invention provides methods of inducing immunological tolerance (generally to a xenotransplantation antigen, more specifically to αGal), comprising administering an effective amount any of the conjugates described herein to the individual.

In another aspect, the invention provides methods of detecting the presence and/or amount of anti-αGal antibody in a biological sample comprising (a) contacting an αGal conjugate of the invention with the biological sample under conditions that permit the formation of a stable antigen-antibody complex; and (b) detecting stable complex, if any, formed in step (a).

In another aspect, the invention provides methods for performing a xenotransplantation in an individual, comprising the steps of: (a) administering any of the conjugate(s) or composition(s) described herein to the individual; and (b) introducing xenotissue to an individual.

In another aspect, the invention provides methods of suppressing rejection of a transplanted tissue comprising an α Gal epitope in an individual, said method comprising administering any of the conjugates described herein to the individual in an amount sufficient to suppress rejection.

MODES FOR CARRYING OUT THE INVENTION

Figure 1:
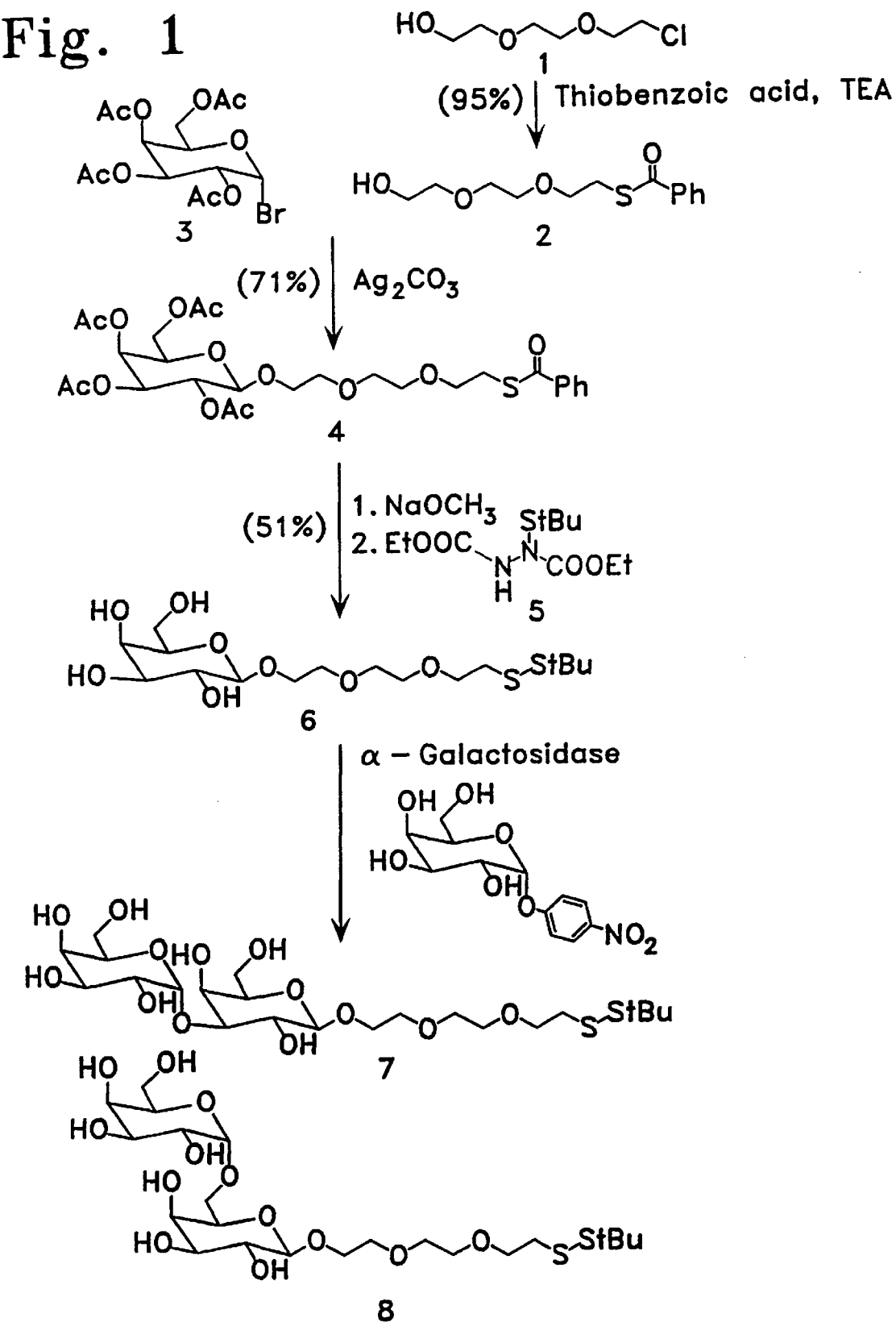
FIG. 1 is a reaction scheme illustrating the enzymatic synthesis of the αGal epitope, 2-[2-(2-thioethoxy)ethoxy] ethyl 3-O-(α-D-galactopyranosyl)-β-D-galactopyranoside.

We have discovered conjugates designed both to bind to and clear circulating anti-αGal antibodies and bind to and tolerize αGal-specific B cells. The conjugates can be used to neutralize, reduce and/or remove anti-αGal antibodies, whether transiently and/or more permanently (i.e., as a toleragen which dampens and/or eliminates the anti-αGal antibody response in potential recipients of αGal epitope-bearing organs). They may also be used to detect circulating levels anti-αGal antibodies. We have found that conjugates comprising a valency platform molecule and an αGal epitope can bind to and remove from the circulation the anti-αGal IgG and IgM (the major effector molecule of hyperacute rejection) in a valency dependent manner that is consistent with the high affinity of the IgG anti-αGal antibodies and the lower affinity but higher avidity of the IgM response.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait,ed., 1984); "Animal Cell Culture" (R. I. Freshney), ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR": The Polymerase Chain Reaction", (Mullis et al., eds., 1994); and "Current Protocols in Immunology" (J. E. Coligan et al., eds., 1991).

Definitions

An "αGal epitope" is any chemical moiety which exhibits specific binding to an anti-αGal antibody. As such, examples of an αGal epitope include, but are not limited to, any moiety comprising a α-D-galactopyranoside moiety, Gal, Galα1-3Gal, Galα1-4Gal, Galα1-6Gal, Galα1-3Galα1-3GlcNAc, Galα1-3Galα1-4Gal, Galα1-3Galα1-4GlcNAc, Galα1-3Galα1-4Glc, Galα1-3Galα1-4[3-deoxy]GlcNAc, Galα1-3Galα1-4[6-deoxy]GlcNAc, Galα1-3Galα1-4Galα1-3Gal, Galα1-3Galα1-4GlcNAcα1-3Galα1-4Glc, (McKane et al., *Transplantation* (1998) 66:626–633; Wieslander et al. *Glycoconjugate* (1990) 7:85–100; Galili et al. *J. Biol. Chem.* (1988) 263:17755–17762; Galili et al. *J. Exp. Med.* (1985) 162:573–582); peptides, and any multimers and combination(s) of the foregoing. Further discussion of αGal epitopes suitable for the conjugates of the invention are described below.

An epitope that "specifically binds" to an antibody is a term well understood in the art, and methods to determine such specific binding are also well known in the art. A molecule is said to exhibit "specific binding" if it reacts or associates more frequently, more rapidly, with greater duration and/or with greater affinity with a particular cell or substance than it does with alternative cells or substances. An antibody "specifically binds" to a target if it binds with greater affinity, avidity, more readily, and/or with greater duration than it binds to other substances. The term "epitope" also includes mimetics of αGal itself, which are described below, As used in the specification and claims, and as this description makes clear to one skilled in the art, the singular form "a", "an", and "the" include plural references unless the context clearly indicates otherwise.

An "anti-αGal antibody" or "αGal antibody", used interchangeably herein, is any antibody which specifically binds to αGal. Any antibody includes an antibody of any class, such as IgG, IgA, or IgM, and the antibody need not be of any particular class. As clearly indicated in the definition of "antibody" provided herein, a "anti-αGal antibody" encompasses any fragment(s) that exhibits this requisite functional (i.e., specific binding to αGal) property, such as fragments that contain the variable region, such as Fab fragments. As discussed below, it is understood that specific binding to any anti-αGal antibody (or functional fragment) is sufficient.

An "antibody" (interchangeably used in plural form) is an immunoglobulin molecule capable of specific binding to a target, such as a carbohydrate or polypeptide, through at least one antigen recognition site, located in the variable region of the immunoglobulin molecule. As used herein, the term encompasses not only intact antibodies, but also fragments thereof (such as Fab, Fab', F(ab')$_2$, Fv), single chain (ScFv), mutants thereof, fusion proteins comprising an antibody portion, humanized antibodies, and any other modified configuration of the immunoglobulin molecule that comprises an antigen recognition site of the required specificity.

"Naturally occurring" refers to an endogenous chemical moiety, such as a carbohydrate, polynucleotide or polypeptide sequence, i.e., one found in nature. Processing of naturally occurring moieties can occur in one or more steps, and these terms encompass all stages of processing. Conversely, a "non-naturally occurring" moiety refers to all other moieties, i.e., ones which do not occur in nature, such as recombinant polynucleotide sequences and non-naturally occurring carbohydrates.

As used herein, the term "mimetic" (also termed an "analog") means a biological or chemical compound which specifically binds to an anti-αGal antibody. As such, for purposes of this invention, an "αGal epitope" includes mimetics of naturally-occurring αGal (such as peptides). A "mimetic" shares an epitope, or binding specificity, with αGal. A mimetic may be any chemical substance which exhibits the requisite binding properties, and thus may be, for example, a simple or complex organic or inorganic molecule; a polypeptide; a polynucleotide; a carbohydrate; a lipid; a lipopolysaccharide; a lipoprotein, or any combination of the above, including, but not limited to, a polynucleotide-containing polypeptide; a glycosylated polypeptide; and a glycolipid. The term "mimetic" encompasses the term "mimotope", which is a term well known in the art.

An "individual" is a vertebrate, preferably a mammal, more preferably a human. Mammals include, but are not limited to, farm animals, sport animals, pets, primates, mice and rats. "Inducing tolerance" means a reduction and/or stabilization of the extent of an immune response to an immunogen. An "immune response" may be humoral and/or cellular, and may be measured using standard assays known in the art. For purposes of this invention, the immune response is generally reflected by the presence of anti-αGal antibodies. Quantitatively the reduction (as measured by reduction in antibody production and/or levels) is at least about 15%, more preferably at least about 25%, more preferably at least about 50%, more preferably at least about 75%, more preferably at least about 90%, even more preferably at least about 95%, and most preferably 100%. It is understood that the tolerance is antigen-specific, and applies for purposes of the invention to those individuals having anti-αGal antibodies. "Inducing tolerance" also includes slowing and/or delaying the rate of increase of antibody level.

An "effective amount" (when used in the toleragenic context) is an amount sufficient to effect beneficial or desired results, including clinical results. An effective amount can be administered in one or more administrations. For purposes of this invention, an effective amount of conjugate of this invention (or a composition comprising a conjugate of this invention) is an amount sufficient to reduce circulating levels of anti-αGal antibodies, preferably (but not necessarily) by inducing tolerance, particularly with respect to anti-αGal antibodies. In terms of treatment, an "effective amount" of conjugate of the invention (or a composition comprising a conjugate of the invention) is an amount sufficient to palliate, ameliorate, stabilize, reverse, slow or delay progression of or prevent rejection of αGal containing transplanted tissue. Detection and measurement of indicators of efficacy are generally based on measurement of αGal antibody and/or clinical symptoms associated with transplantation rejection.

In the case of hyperacute rejection, molecular changes subsequent to anti-αGal binding to αGal-expressing blood vessels include complement activation and donor endothelial cell activation. This shifts the donor endothelium from an anti-coagulant environment into a procoagualitive surface. This in turn leads to clotting in the vasculature of the engrafted organ and leads to an ischemic state in the organ. Thus, within minutes to 2 hours, blood flow to the organ ceases and the engrafted organ becomes black, with increasing hardness. If hyperacute rejection is avoided by antibody removal (pheresis) or complement regulation, antibodies produced subsequent to engraftment can lead to delayed xenograft rejection wherein antibodies bound to the endothelium of the engrafted organ can mediate graft cell activation, NK cell binding, antibody dependent cell-mediated cytotoxicity (ADCC) and increased immunogenicity of xenograft-specific antigens.

Accordingly, indications and/or clinical symptoms of transplantation rejection include, but are not limited to, reduction or loss of organ function (for example, change in urine output, for kidneys; and change in rhythm, for heart); complement activation, as indicated, for example, by presence or increased levels of components of the complement cascade, such as C3a, C5a, and C5b-9; NK activity; and antibody-dependent cell-mediated cytotoxicity (ADCC). For example, heart function may be monitored by measuring appropriate markers, such as creatine kinase (CK), and CK isoenzyme CK MB, and lactate dehydrogensase in serum. Kidney failure is characterized by hematuria, decreased urine output, elevated blood urea nitrogen levels, elevated serum creatinine levels, hypertension, and proteinuria. Accordingly, these parameters can be monitored as a means of monitoring kidney xenotransplant rejection.

As used herein "valency platform molecule" means a nonimmunogenic molecule containing sites which allow the attachment of a discrete number of epitopes and/or mimetic(s) of epitopes. A "valency" of a conjugate or valency platform molecule indicates the number of attachment sites per molecule for an αGal epitope(s). Alternatively, the valency of a conjugate is the ratio (whether absolute or average) of αGal epitope to valency platform molecule.

"Nonimmunogenic", when used to describe the valency platform molecule, means that the valency platform molecule fails to elicit an immune response, and/or fails to elicit a sufficient immune response, when it is administered by itself to an individual. The degree of acceptable immune response depends on the context in which the valency platform molecule is used, and may be empirically determined.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

A "stable complex" formed between any two or more components in a biochemical reaction, refers to a duplex or complex that is sufficiently long-lasting to persist between formation of the duplex or complex and subsequent detection, including any optional washing steps or other manipulation that may take place in the interim.

The term "neutralize", when used in the context of circulating anti-αGal antibody, is a term well understood in the art and intends that an αGal conjugate of the invention binds to a circulating anti-αGal antibody such that it can no longer bind to an αGal epitope on donor tissue.

The term "circulating anti-αGal antibody", as used herein, intends an anti-αGal antibody which is not bound to an αGal antigen/epitope on donor tissue/organ, i.e., free antibody. "Levels" of circulating antibody means amount (quantity) of antibody. "Reducing" levels of circulating anti-αGal antibody means that the level of free, or unbound, circulating antibodies has been reduced. Levels of free antibody can be reduced by any of a number of ways, including binding a conjugate (so that the antibody can no longer be an effector molecule); clearance (removal from circulation); reduction of production via, for example, B cell anergy.

Conditions that "allow" or "permit" an event to occur, such as binding of an anti-αGal antibody to an epitope which binds an anti-αGal antibody, are conditions that do not prevent such events from occurring. Thus, these conditions enhance, facility, and/or are conducive to the event. Such conditions, known in the art and described herein, may be determined and practiced using standard methods in the art.

Conjugates of the Invention

The invention provides conjugates useful for prevention, reduction, and/or delay of xenotransplantation rejection based on undesirable immune response to αGal present on the transplanted tissue. The conjugates of the invention comprise (a) an αGal epitope; and (b) a valency platform molecule. Optionally, a linker is provided between the platform and the αGal epitope, as described below. Various valencies are permitted, and particularly preferred valencies are described below.

αGal Epitope

αGal epitopes for use in the conjugates of the present invention may be any chemical moiety which specifically binds to an αGal antibody. As such, a conjugate which comprises an αGal epitope is a conjugate which contains any molecule or moiety which contains an αGal epitope.

Because the chemical structure of αGal is known, an the epitope is known (α-D-galactopyranoside), one may prepare and obtain an αGal epitope from naturally-occurring αGal. More preferably, an αGal epitope may also be made synthetically using standard chemical synthetic methods. Examples of synthetically produced αGal epitopes are provided in Example 1. Accordingly, examples of αGal epitopes used in the conjugates of the invention, include, but are not limited to, 2-[2-(2-thioethoxy)ethoxy]ethyl 3-O-(α-D-galactopyranosyl)-α-D-galactopyranoside; 2-[2-(2-thioethoxy)ethoxy]ethyl 6-O-(α-D-galactopyranosyl)-α-D-galactopyranoside; 2-[2-(2-Benzoylthioethoxy)ethoxy]ethyl α-D-galactopyranoside; 2-[2-(2-tert-Butyldithioethoxy)ethoxy]ethyl α-D-galactopyranoside; 2-[2-(2-tert-Butyldithioethoxy)ethoxy]ethyl 3-O-(α-D-galactopyranosyl)-α-D-galactopyranoside; 2-[2-(2-tert-butyldithioethoxy)ethoxy]ethyl 3-O-(α-D-galactopyranosyl)-α-D-galactopyranoside; p-aminophenyl-3-O-(α-D-galactopyranosyl)-α-D-galactopyranoside.

As made clear in the definition of an "αGal epitope", an αGal epitope need not be based on, or derived from, the naturally-occurring a carbohydrate moiety, but may be, for example, a peptide. Examples of peptide αGal epitopes are provided in WO 97/11963. An αGal epitope may also be comprised of other organic moieties. For example, a series of organic compounds (whether randomly produced or non-randomly designed) may be synthesized and screened for the requisite binding activity.

Detection of specific binding may be conducted using standard techniques in the art, such as ELISA, FACS, and competition assays. Anti-αGal antibodies may be isolated from a source of anti-αGal antibodies, such as the serum of an immunized animal, using, for example, affinity chromatography. The Examples provide exemplary description of isolation of anti-αGal antibodies and appropriate assays.

It is understood that, for purposes of this invention, more than one type of αGal epitope(s) may be used in preparing a conjugate. Alternatively, one type (i.e., one chemical species) of an αGal epitope may be used.

Valency Platform Molecules

Any of a variety of non-immunogenic valency platform molecules (also called "platforms") may be used in the conjugates of the invention.

A platform may be proteinaceous or non-proteinaceous (i.e., organic). Examples of proteinaceous platforms include, but are not limited to, albumin, gammaglobulin, immunoglobulin (IgG) and ovalbumin. Borel et al. (1990) *Immunol. Methods* 126:159–168; Dumas et al. (1995) *Arch. DematoL Res.* 287:123–128; Borel et al. (1995) *Int. Arch. Allergy Immunol.* 107:264–267; Borel et al. (1996) *Ann. N.Y. Acad. Sci.* 778:80–87.

Preferably, the conjugates comprise a chemically defined valency platform molecule in which a precise valency (as opposed to an average) is provided. Certain classes of chemically defined valency platforms, methods for their preparation, conjugates comprising them, and methods for the preparation of such conjugates, have been described in the U.S. Pat. Nos. 5,162,515; 5,391,785; 5,276,013; 5,786,512; 5,726,329; 5,268,454; 5,552,391; 5,606,047; and 5,663,395. Accordingly, a defined valency platform is a platform with defined structure, thus a defined number of attachment points and a defined valency. In contrast to previously described, more traditional platforms, these platforms have the advantage of having a homogeneous (i.e., uniform) molecular weight (as opposed to polydisperse molecular weight), and are thus "chemically defined". Accordingly, a population of conjugates using these platforms comprise a platform of homogeneous molecular weight or are substantially monodisperse (i.e., have a narrow molecular weight distribution). A measure of the breadth of distribution of molecular weight of a sample (such as a composition and/or population of platform molecules) of a platform molecule is the polydispersity of the sample. Polydispersity is used as a measure of the molecular weight homogeneity or nonhomogeneity of a polymer sample. Polydispersity is calculated by dividing the weight average molecular weight (Mw) by the number average molecular weight (Mn). The value of Mw/Mn is unity for a perfectly monodisperse polymer. Polydispersity (Mw/Mn) is measured by methods available in the art, such as gel permeation chromatography. The polydispersity (Mw/Mn) of a sample of platform molecules is preferably less than 2, more preferably, less than 1.5, or less than 1.2, less than 1.07, less than 1.02, or, e.g., about 1.05 to 1.5 or about 1.05 to 1.2. Typical polymers generally have a polydispersity of 2–5, or in some cases, 20 or more. Advantages of the low polydispersity property of the valency platform molecules include improved biocompatibility and bioavailability since the molecules are substantially homogeneous in size, and variations in biological activity due to wide variations in molecular weight are minimized. The low polydispersity molecules thus are pharmaceutically optimally formulated and easy to analyze. Further there is controlled valency of the population of molecules in the sample.

Figure 7:
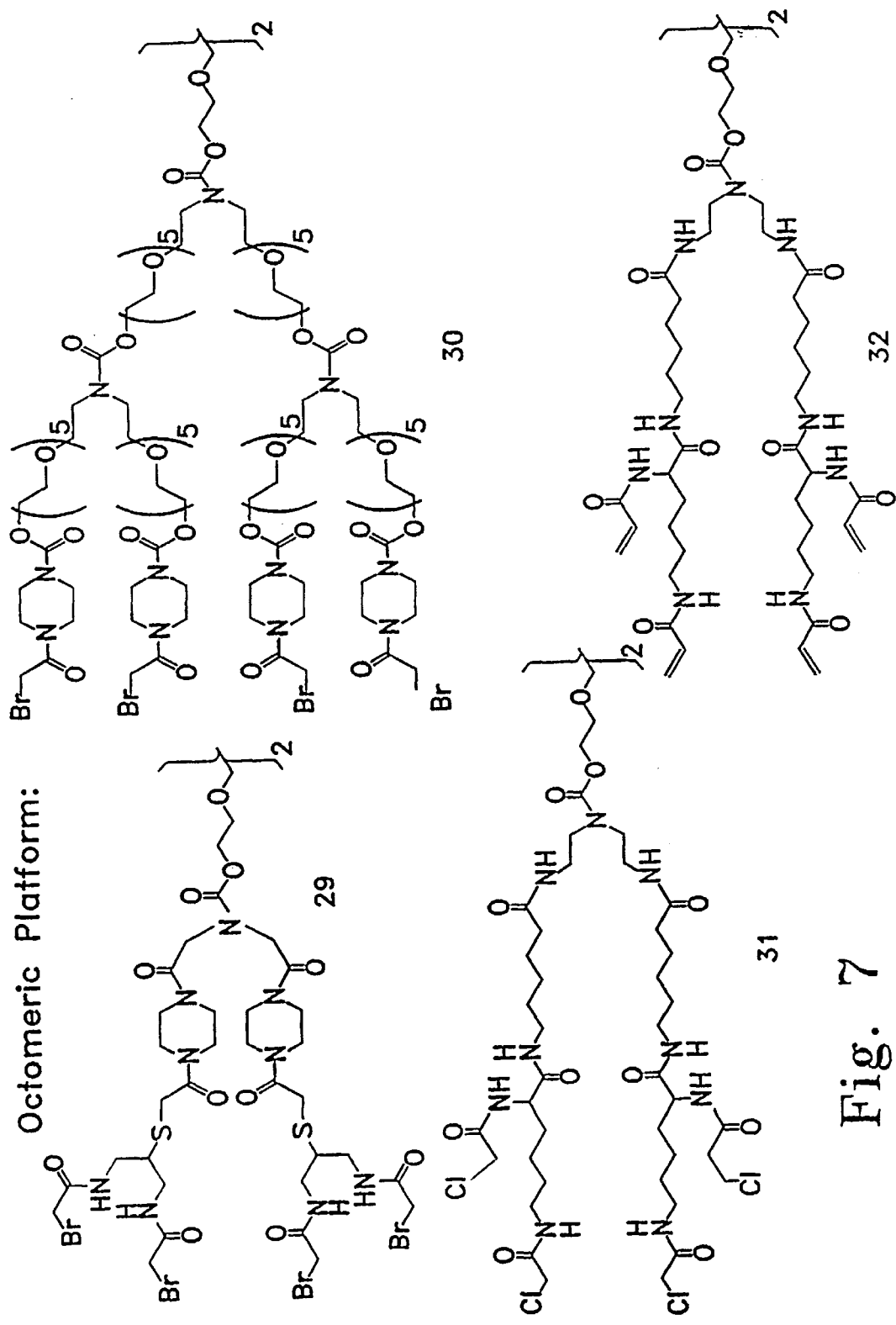
FIG. 7 illustrates four octameric platforms (compounds 29, 30, 31, and 32).
Figure 8:
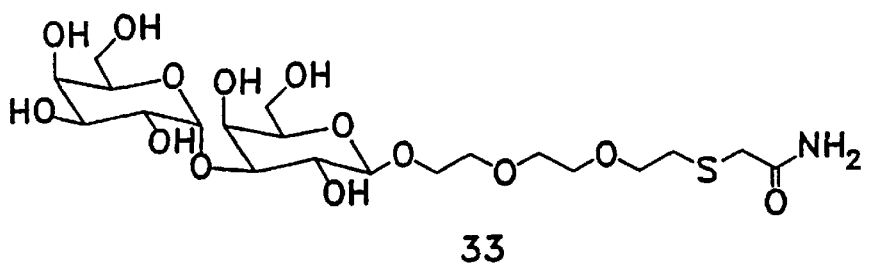
FIG. 8 illustrates a monomeric αGal conjugate (compound 33) and four dimeric αGal conjugates (compounds 33, 34, 35, and 36).
Figure 8:
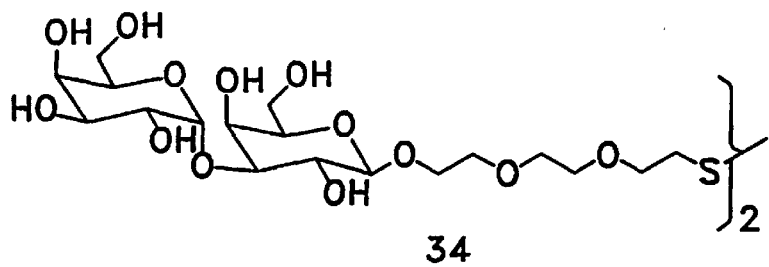
Figure 8:
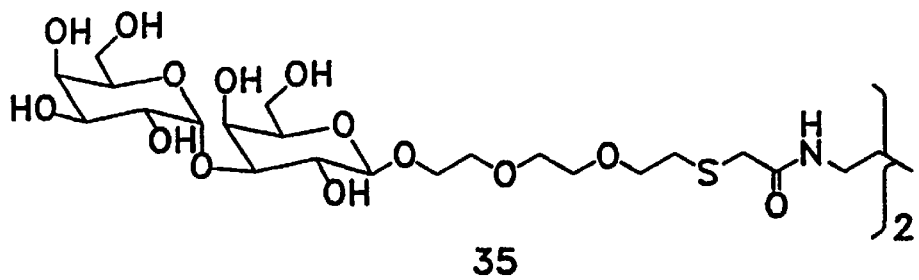
Figure 8:
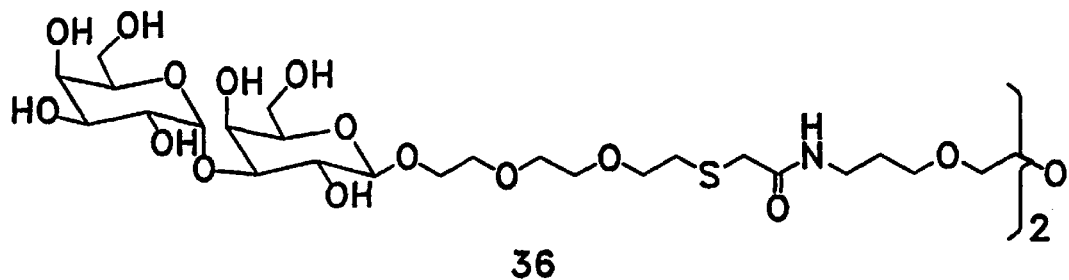
Figure 9:
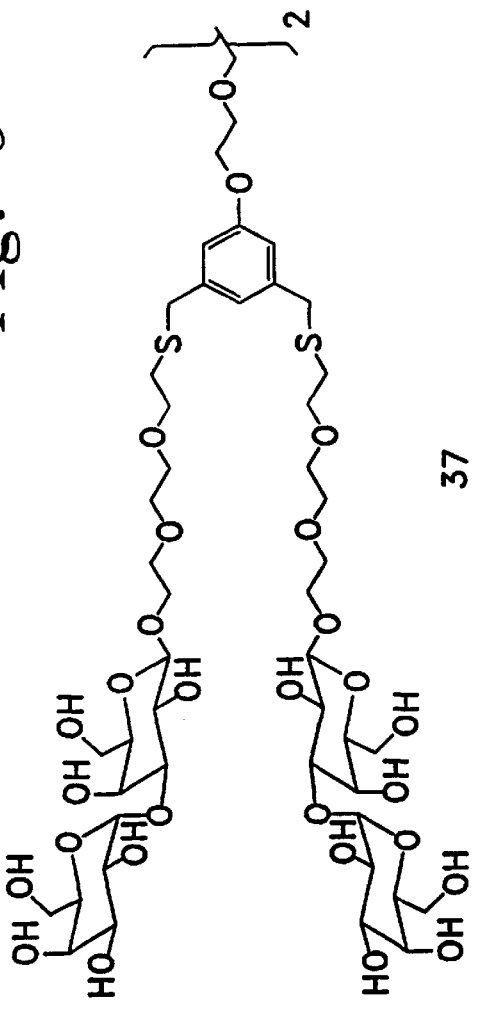
FIG. 9 illustrates two tetrameric αGal conjugates (compounds 37 and 38) as described in Example 3.
Figure 9:
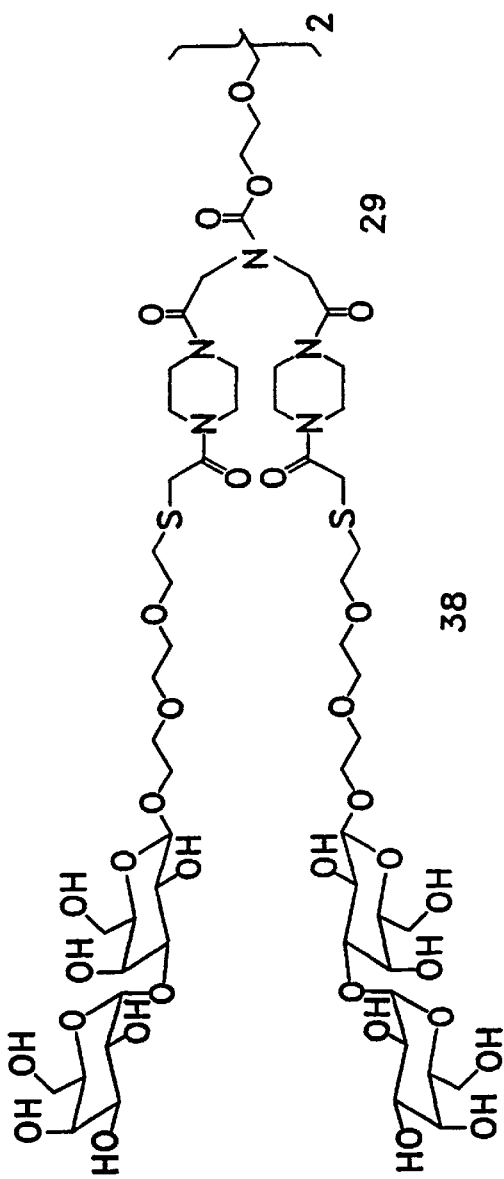
Figure 10:
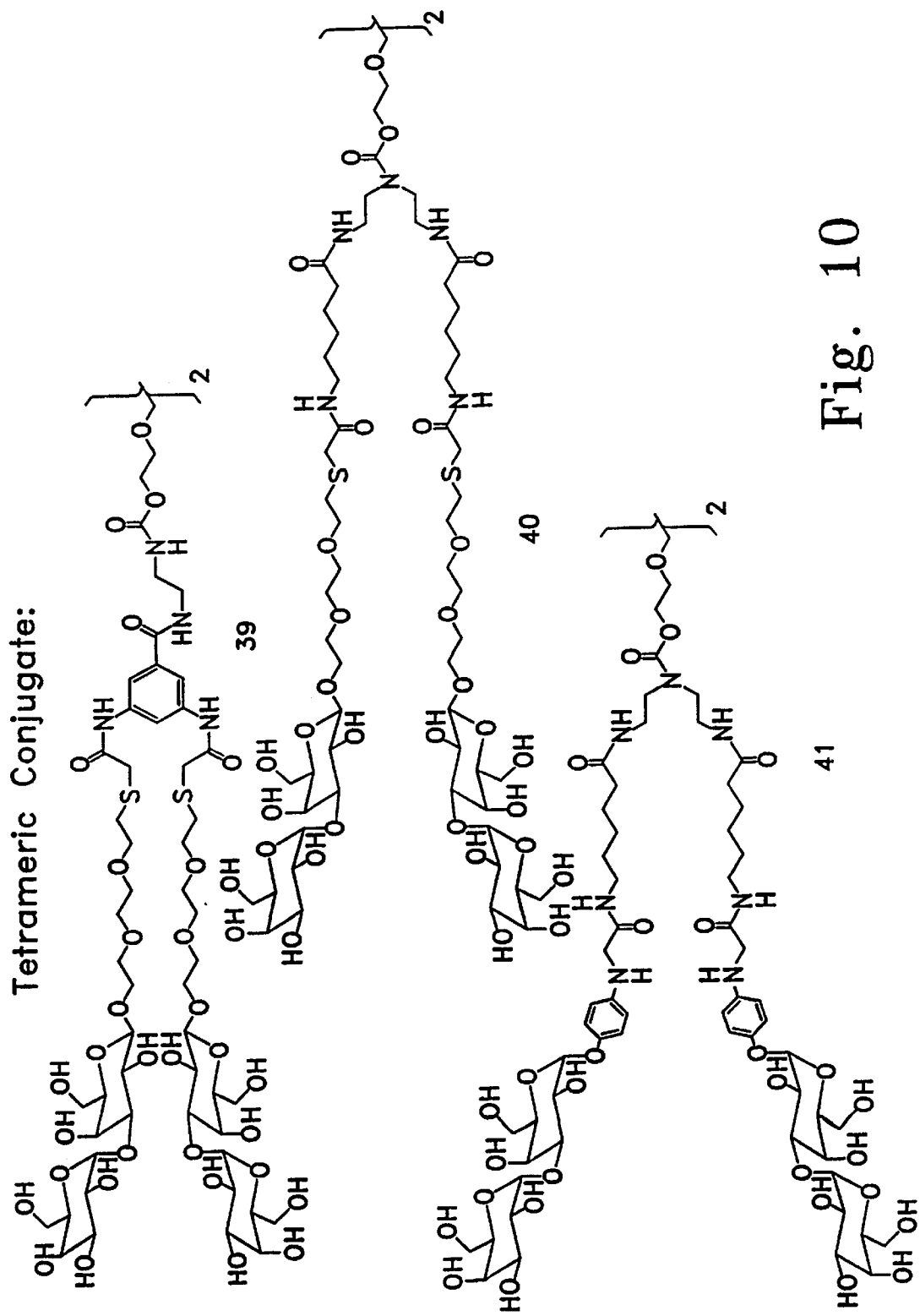
FIG. 10 illustrates three tetrameric αGal conjugates (compounds 39, 40, and 41) as described in Example 3.
Figure 11:
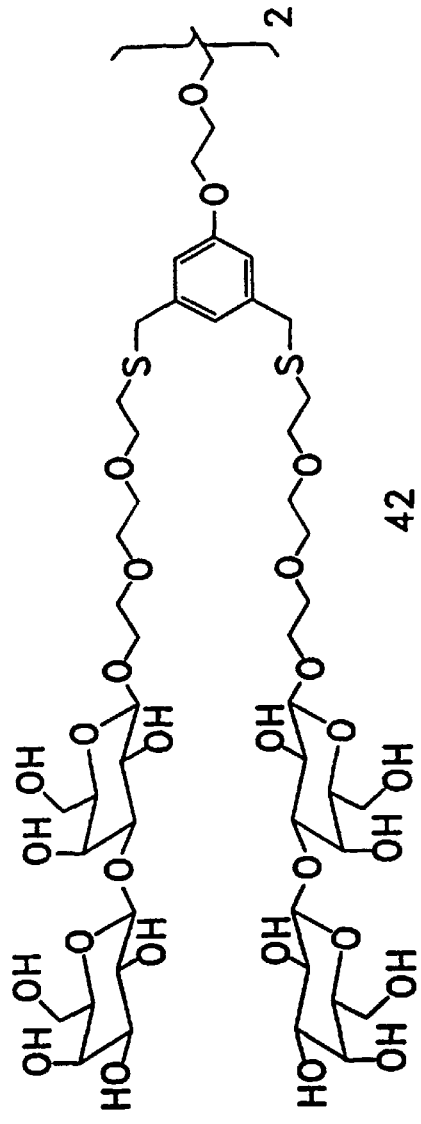
FIG. 11 illustrates two tetrameric conjugates (compounds 42 and 43) of two αGal -isomers as described in Example 3.
Figure 11:
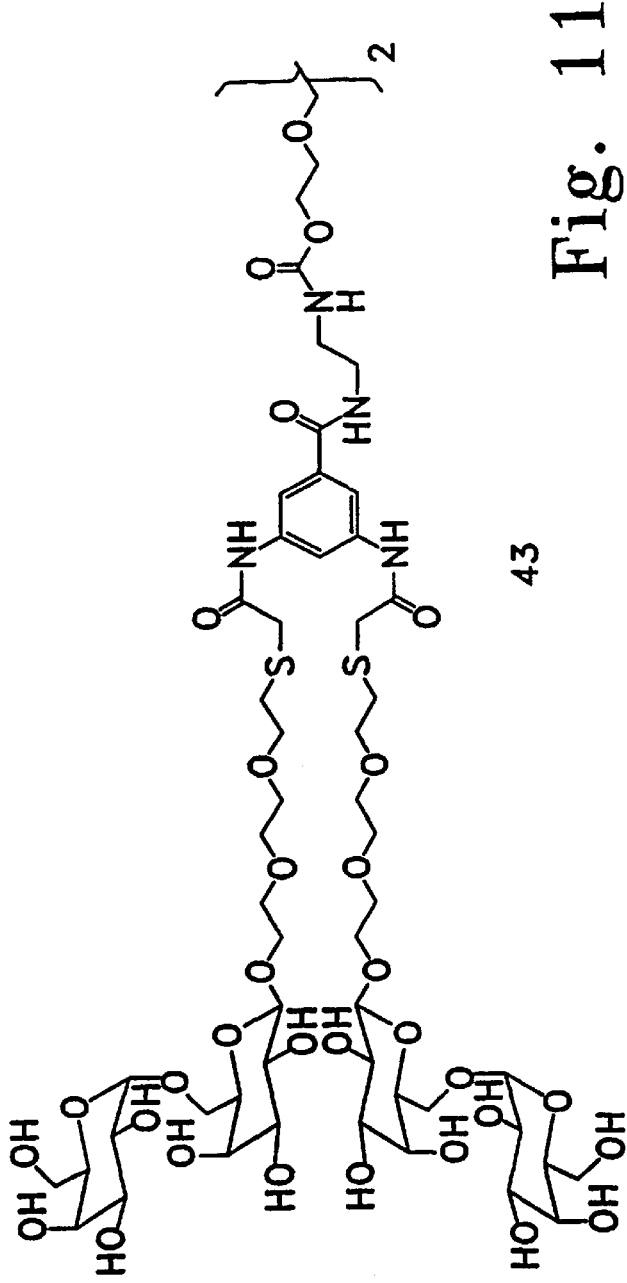
Figure 12:
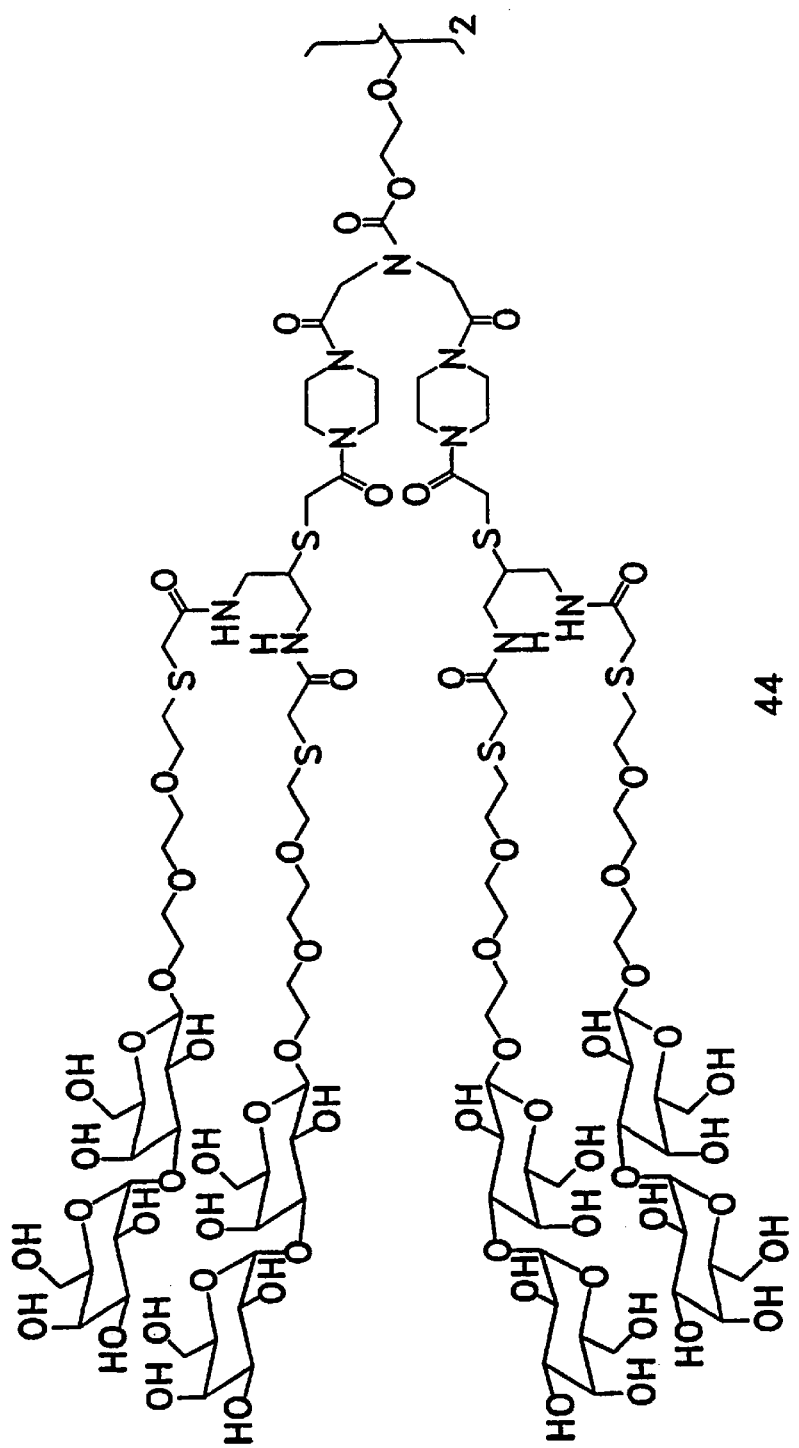
FIG. 12 illustrates an octameric αGal conjugate (compound 44) as described in Example 3.
Figure 13:
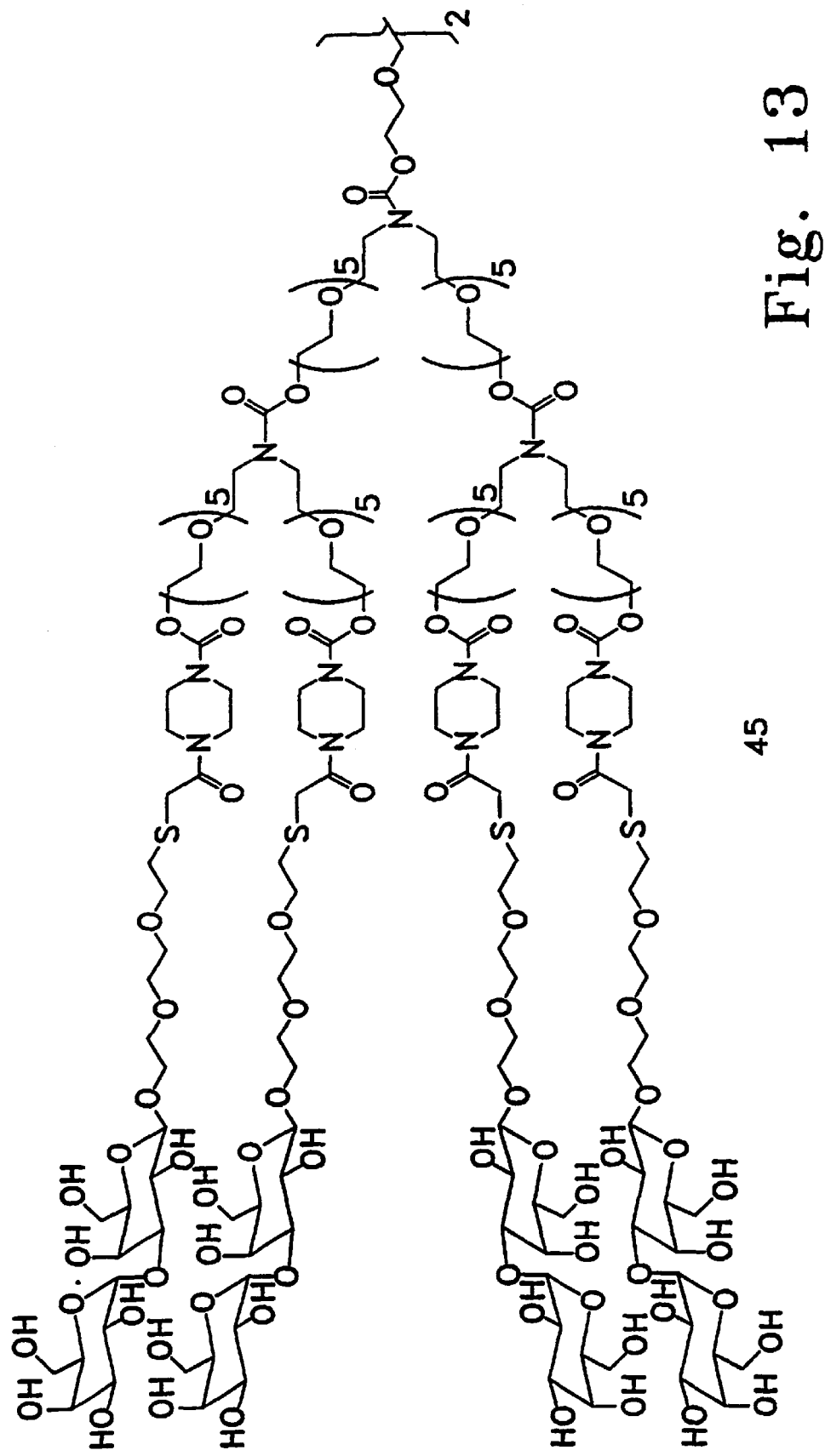
FIG. 13 illustrates an octameric αGal conjugate (compound 45) as described in Example 3.
Figure 14:
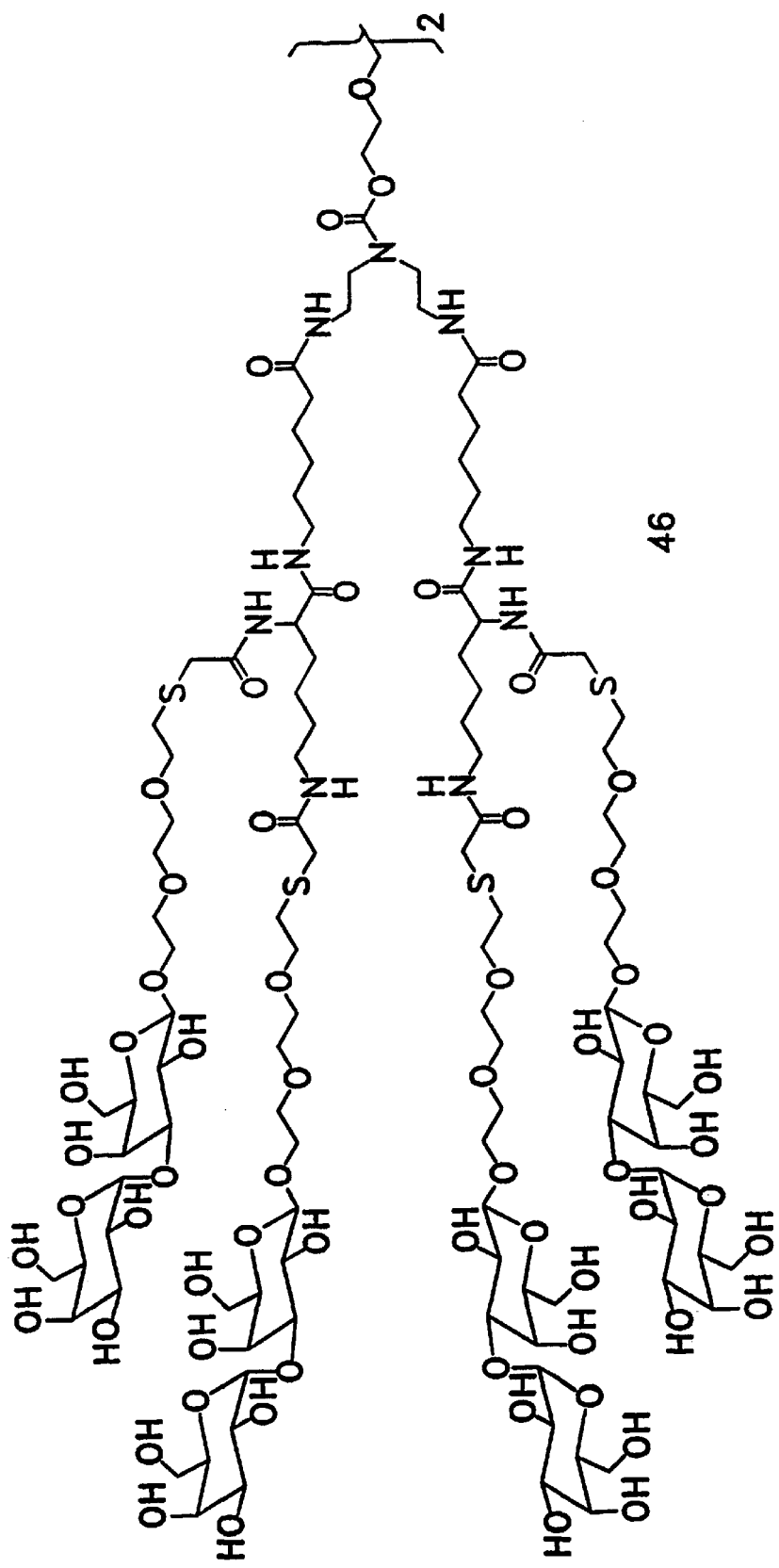
FIG. 14 illustrates an octameric αGal conjugate (compound 46) as described in Example 3.
Figure 15:
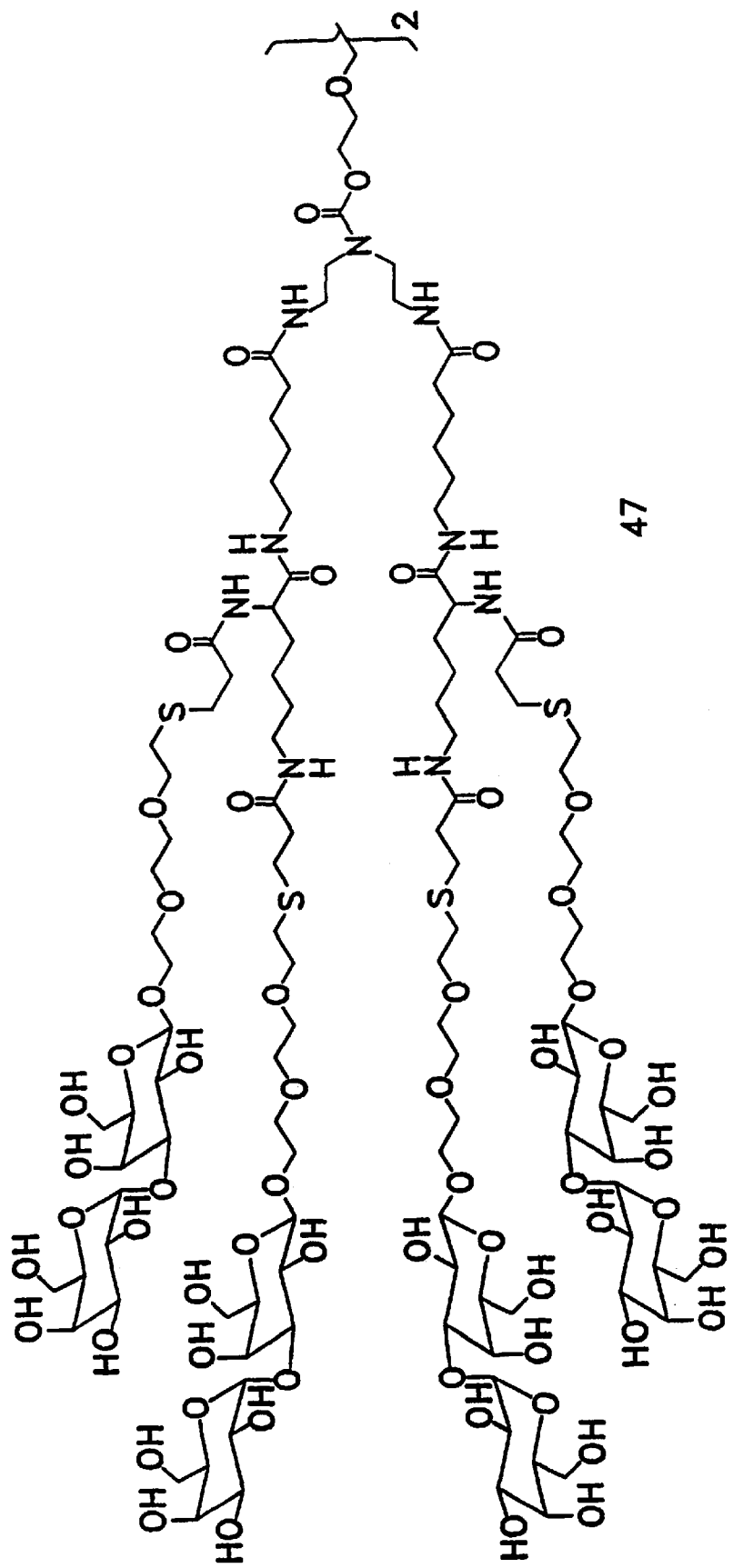
FIG. 15 illustrates an octameric αGal conjugate (compound 47) as described in Example 3.

In some embodiments, the valency platform molecule comprises a carbamate linkage, i.e., —O—C(=O)—N<. Such platforms are described in a co-owned patent application entitled "Valency Platform Molecules Comprising Carbamate Linkages" U.S. Ser. No. 60/111,641. An example of such a platform is compound 30, which is shown in FIG. 7. In other embodiments, the valency platform molecule comprises an aminooxy group, as described in co-owned U.S. Ser. No. 60/138,260.

Preferred valency platform molecules are biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 200,000, preferably about 200 to about 50,000 (or less, such as 30,000). Examples of valency platform molecules within the present invention are polymers (or are comprised of polymers) such as polyethylene glycol (PEG), poly-D-lysine, polyvinyl alcohol, polyvinylpyrrollidone, D-glutamic acid and D-lysine (in a ratio of 3:2). Preferred polymers are based on polyethylene glycols (PEGs) having a molecular weight of about 200 to about 8,000. Other suitable platform molecules for use in the conjugates of the invention are albumin and IgG.

Other preferred valency platform molecules suitable for use within the present invention are the chemically-defined, non-polymeric valency platform molecules disclosed in co-owned U.S. Pat. No. 5,552,391. Preferred homogeneous chemically-defined valency platform molecules suitable for use within the present invention are derivatized 2,2'-ethylenedioxydiethylamine (EDDA) and triethylene glycol (TEG).

Additional suitable valency platform molecules include, but are not limited to, tetraaminobenzene, heptaaminobetacyclodextrin, tetraaminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Figure 6:
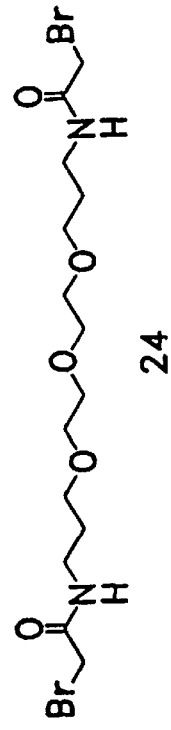
FIG. 6 illustrates two dimeric platforms (compounds 23 and 24) and four tetrameric platforms (compounds 25, 26, 27, and 28).
Figure 6:
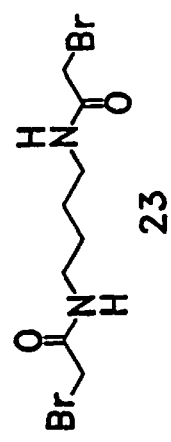
Figure 6:
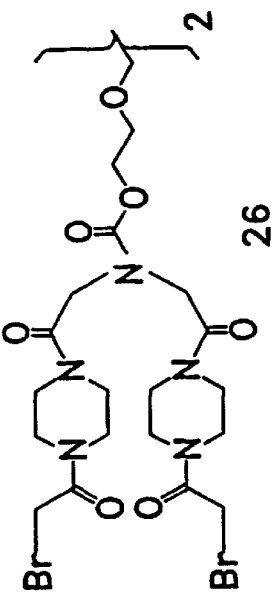
Figure 6:
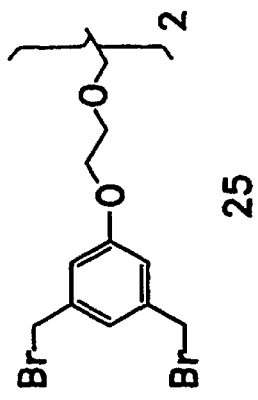
Figure 6:
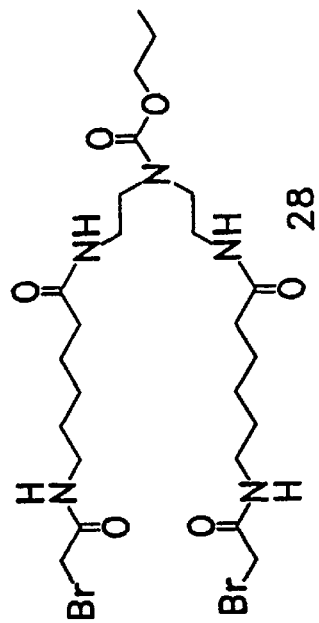
Figure 6:
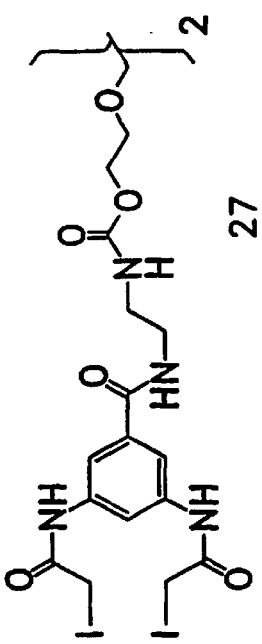

Synthesis of valency platforms, such as compound 25, 26, and 27, whose structures are shown in FIG. 6, is described in co-owned patent application U.S. Ser. No. 08/660,092, now U.S. Pat. No. 6,207,160, and co-owned International Patent Application Nos PCT/US96/09976 and PCT/US97/10075.

Synthesis of valency platforms 23, 24, 29, 30, 31 and 32, whose structures are shown in FIGS. 6 and 7, is described in Example 2.

As discussed above, αGal epitopes may be conjugated to any of a number of suitable platforms by any of a number of ways. In a preferred embodiment, the tetra-bromoacetyl platform PIZ/IDA/TEG platform is used. Derivatives of the PIZ/IDA/TEG (PITG) platform can be prepared as shown below.

Examples of Compatible Cross-linking Groups on PITG Platform

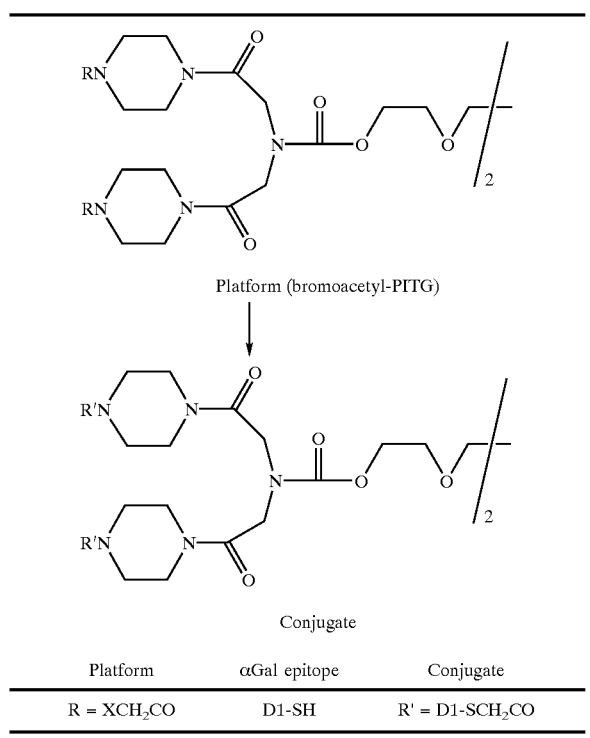

| Platform | αGal epitope | Conjugate |
|---|---|---|
| R = XCH$_2$CO | D1-SH | R' = D1-SCH$_2$CO |

By way of example of a conjugate embodiment, an αGal epitope is prepared with a thiol linker at the N terminus by chemical or enzymatic synthesis (or by recombinant methods if the αGal epitope is a peptide). The linker can be cysteine or an SH containing moiety. The modified epitope may then be alkylated by a suitably derivatized platform (such as bromoacetyl or iodoacetyl).

For purposes of this invention, the valency platform molecules have a minimum valency of at least two, preferably at least four, preferably at least six, more preferably at least eight, preferably at least 10, preferably at least 12. As an upper limit, valency is generally less than 128, preferably less than 64, preferably less than 35, preferably less than 30, preferably less than 25, preferably less than 24, preferably less than 20, although the upper limit may exceed 128. Without wishing to be bound by a particular theory, the valency is generally limited to numbers above which a conjugate could become a T cell independent antigen, i.e., would not induce B cell tolerance due to its T cell independence. Thus, the invention includes conjugates with a valency of ranges of any of the lower limits of 2, 4, 6, 8, 10, 12, 16, with any of the upper limits of 128, 64, 35, 30, 25, 24, 20.

Preferably, the valency is at least eight (with the upper limits as described above). As described in the Examples, a synthetically prepared αGal epitope presented on a platform as an octamer inhibited both IgG and IgM anti-αGal in serum from binding to BSA-αGal or to the αGal-expressing porcine kidney epithelial cell line PK-15. By contrast, the tetrameric construct only removed the IgG. This difference may be attributed to the lower affinity of the IgM anti-αgal antibodies which was overcome by increased epitope valency. This is significant, since IgM is the major effector molecule of HAR. By ELISA, there was no statistically significant diminution of anti-αGal Ig responses with the tetramer at 2–10 mg/kg. By contrast, treatment with 20 mg/kg of the tetrameric conjugate (denoted "LJP 712", and also referred to as cpd 38 in the Examples) resulted in the diminution of the anti-αGal IgG response by up to 24% ($p<0.05$) and anti-αGal IgM levels by up to 12% (p=NS).

In some embodiments, the valency is two. In other embodiments, the valency is four. In other embodiments, the valency is eight. In other embodiments, the valency is 16. In other embodiments, the valency is any of the following: 6, 10, 14, 18, 20, 22, 24, 26, 28, 30, 34, 36, 38, 40, 42, 44, 46, 48, 50, 52, 54, 56, 58, 60, 62, 66, 68, 70, 72, 74, 76, 78, 80, 90, 120, 128. An example of a valency platform molecule with a valence of two is provided in Example 2 and FIG. 6. An example of a valency platform molecule with a valence of four is provided in Example 2 and FIG. 6. Examples of valency platform molecules with a valence of eight are provided in Example 2 and FIG. 7. Accordingly, the invention includes conjugates comprising these valency platform molecules.

In other embodiments, valency platforms may be used which, when conjugated, provide an average valency (i.e., these platforms are not chemically defined in terms of their valency). Examples of such platforms are polymers such as linear PEG; branched PEG; star PEG; polyamino acids; polylysine; proteins; amino-functionalized soluble polymers.

Conjugation of αGal Eptitope(s) with Valency Platform Molecules

Figure 4:
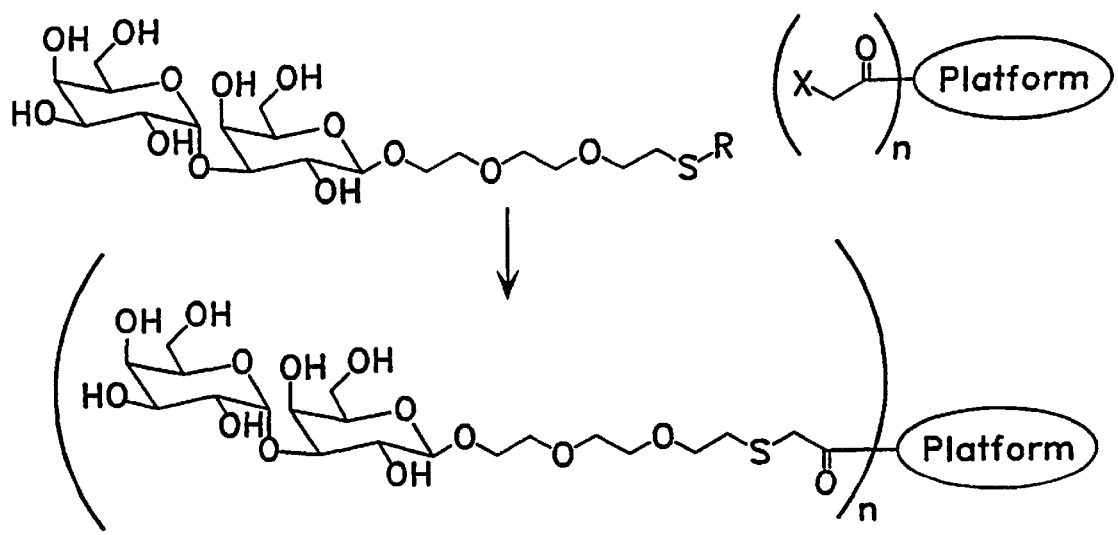
FIG. 4 illustrates two general synthetic strategies for conjugation chemistry.
Figure 4:
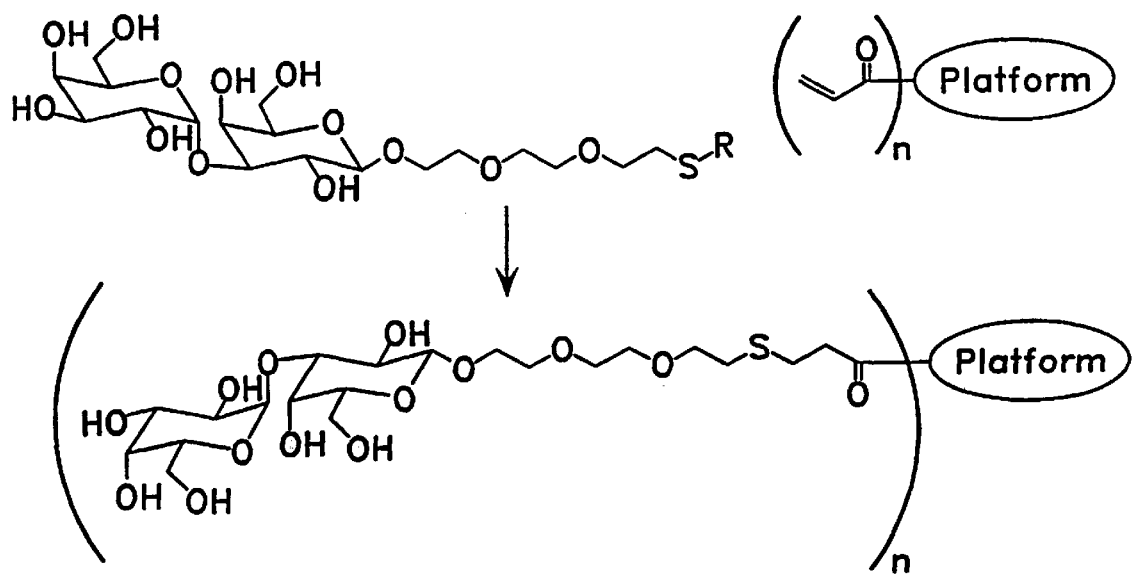
Figure 5:
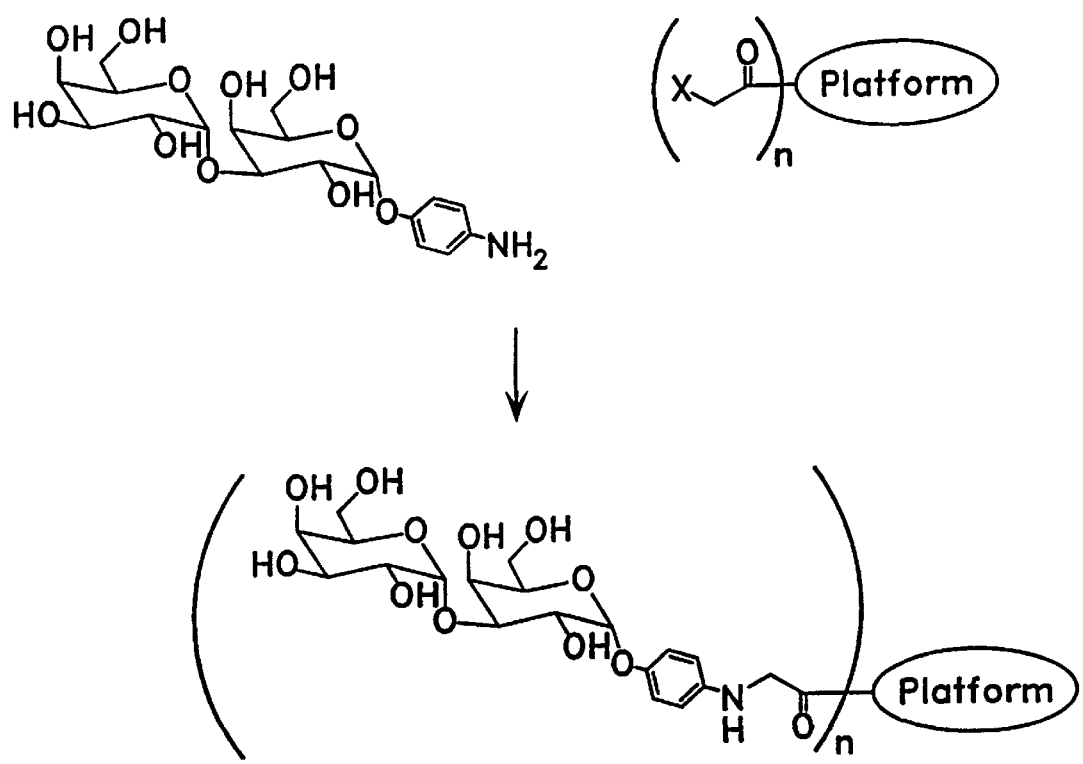
FIG. 5 illustrates a third general synthetic strategy for conjugation chemistry.

Conjugation of αGal epitope(s) with valency platform molecules is performed using standard chemical techniques. The following are examples of standard chemistry which can be used: 1) thiol substitution; 2) thiol Michael addition; 3) amino alkylation; 4) disulfide bond formation. FIGS. 4 and 5 provide general, exemplary conjugation strategies.

Conjugation of an αGal epitope to a valency platform molecule may be effected in any number of ways, typically involving one or more crosslinking agents and functional groups on the epitope and valency platform molecule. Platforms and αGal epitope(s) must have appropriate linking groups. Linking groups are added to platforms using standard synthetic chemistry techniques. Linking groups may be added to an αGal epitope(s) using either standard solid phase synthetic techniques or recombinant techniques (if, for example, the αGal epitope is a peptide). Recombinant approaches may require post-translational modification in order to attach a linker, and such methods are known in the art.

As a further example, if the αGal epitope is a polypeptide, polypeptides contain amino acid side chain moieties containing functional groups such as amino, carboxyl, or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s), functional amino, sulfhydryl and/or aldehyde groups may be incorporated therein by conventional chemistry. For instance, primary amino groups may be incorporated by reaction with ethylenediamine in the presence of sodium cyanoborohydride, sulflhydryls may be introduced by reaction of cysteamine dihydrochloride followed by reduction with a standard disulfide reducing agent, while aldehyde groups may be generated following periodate oxidation. In a similar fashion, the valency platform molecule may also be derivatized to contain functional groups if it does not already possess appropriate functional groups.

Hydrophilic linkers of variable lengths are useful for connecting αGal epitopes to valency platform molecules. Suitable linkers include linear oligomers or polymers of ethylene glycol. Such linkers include linkers with the formula $R^1S(CH_2CH_2O)_nCH_2CH_2O(CH_2)_mCO_2R^2$ wherein n=0–200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. These linkers are flexible with regard to the order of attachment, i.e., the thioether can be formed first or last.

Particular conjugates are described in Example 3 and are depicted in FIGS. 8–15, which accordingly are provided as embodiments of the invention.

Compositions of the Invention

The invention also provides compositions comprising any of the conjugates of the invention. Preferably, the compositions comprise an effective amount of a conjugate(s). An "effective amount" depends on the desired or intended result and may be determined empirically. For example, an amount effective to reduce circulating levels of anti-αGal antibodies may be determined by conducting appropriate tests or studies. An amount effective to more permanently reduce the level of circulating anti-αGal antibodies (i.e., induce tolerance) may likewise be determined empirically.

With respect to compositions which may be used as reagents (such as in detection of anti-αGal antibodies), these compositions generally comprise an amount of an αGal conjugate of the invention sufficient to effect detection. These amounts are readily determined empirically. These compositions may further comprise a substance, such as a buffer, to effect detection and/or to allow formation of a stable complex between an anti-αGal antibody and an αGal epitope on a conjugate of the invention. These compositions may also optionally be complexed to a detection matrix, such as a solid phase (e.g., in an immunoaffinity column).

In some embodiments, the compositions comprise a conjugate(s) and a pharmaceutically acceptable excipient, and may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonperenteral drug delivery are set forth in *Remington's Pharmaceutical Sciences* 19th Ed. Mack Publishing (1995).

Generally, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like. Generally, the conjugate will normally constitute about 0.01% to 10% by weight of the formulation due to practical, empirical considerations such as solubility and osmolarity. The particular dosage regimen, i.e., dose, timing and repetition, will depend on the particular individual and that individual's medical history. Generally, a dose of about 1 µg to about 100 mg conjugate/kg body weight, preferably about 100 µg to about 10 mg/kg body weight, preferably about 50 µg to about 5 mg/kg body weight, preferably about 1 µg to about 1 g conjugate/kg body weight, preferably about 5 µg to about 500 mg body weight. Empirical considerations, such as the half life, generally will contribute to determination of the dosage. If used as a toleragen, conjugate may be administered daily, for example, in order to effect antibody clearance (pheresis), followed by less frequent administrations, such as two times per week, once a week, or even less frequently. Frequency of administration may be determined and adjusted over the course of therapy, and is based on maintaining tolerance (i.e., reduced or lack of immune response to αGal). Other appropriate dosing schedules may be as frequent as daily or 3 doses per week, or one dose per week, or one dose every two to four weeks, or one dose on a monthly or less frequent schedule depending on the individual or the disease state. Repetitive administrations, normally timed according to B cell turnover rates, may be required to achieve and/or maintain a state of humoral anergy. Such repetitive administrations generally involve treatments of about 1 µg to about 10 mg/kg body weight or higher every 30 to 60 days, or sooner, if an increase in anti-αgal antibody level is detected. Alternatively, sustained continuous release formulations of the compositions may be appropriate. Various formulations and devices for achieving sustained release are known in the art.

Other formulations include suitable delivery forms known in the art including, but not limited to, carriers such as liposomes. Mahato et al. (1997) *Pharm. Res.* 14:853–859. Liposomal preparations include, but are not limited to, cytofectins, multilamellar vesicles and unilamellar vesicles.

In some embodiments, more than one conjugate (e.g., mixtures that vary with respect to valency and/or nature of epitope) may be present in a composition. Such compositions may contain at least one, at least two, at least three, at least four, at least five different conjugates. Such "cocktails", as they are often denoted in the art, may be particularly useful in treating a broader range of population of individuals. They may also be useful in being more effective than using only one (or fewer than are contained in the cocktail) conjugate(s).

The compositions may be administered alone or in conjunction with other forms of agents that serve to enhance and/or complement the effectiveness of a conjugate of the invention, including, but not limited to, anti-helper T cell treatments. Such treatments usually employ agents that suppress T cells such as steroids or cyclosporin. The compositions may also be administered with agents (such as immunosuppressants) which are used to suppress transplantation rejection.

An individual suitable for administration of a conjugate(s) (or composition comprising an conjugate(s) of the invention) is one who has or will receive tissue which is known to contain (i.e., expressed on the cell surface), or is believed to contain, αGal. In order to tolerize an individual to a donor organ or tissue, it is generally preferable to administer the conjugate before transplantation, generally at least about 1 to about 5, preferably at least about 5 to about 10, more preferably at least about 10 to about 30; even more preferably at least about 30 to about 60 days before transplantation. In order to neutralize circulating anti-αGal Ab, e.g., in an acute setting, the conjugate can be administered either concurrently with or after xenotransplantation. Accordingly, depending on the desired result, the conjugate can be administered before, during, or after transplantation. Preferably, the individual is human. Measurable circulating levels of anti-αGal antibody need not be detectable, as mounting an immune response after transplantation could occur.

Kits Comprising Conjugates

The invention also provides kits containing (i.e., comprising) one or more conjugates of the invention. The kits may be used, for example, as vehicles for administration of the conjugate(s) contained therein in a clinical setting. The kits of this invention are in suitable packaging, and may optionally provide additional components such as, buffers and instructions (which may pertain to administration and/or detection). Because the conjugates of the invention may be used to detect anti-αGal antibody, kits of the invention may additionally or alternatively contain reagents suitable for detection of anti-αGal antibody, such as capture reagents, developing reagents, labels, reacting surfaces, means for detection, control samples, and interpretive information.

Any appropriate means for detecting binding of the antibodies may be employed (and provided in the kits) such as a labeled anti-human antibody, when the presence of human anti-αGal antibodies is tested, wherein the label may be an enzyme, fluorophore, chemiluminescent material radioisotope or coenzyme. Generally, the label used will be an enzyme.

Methods Using the Conjugates of the Invention

The invention provides methods of using conjugate(s) of this invention. The conjugates can be used to reduce circulating levels of anti-αGal antibody; induce immunological tolerance in an individual to αGal epitopes on donor tissue/ organs; to neutralize circulating anti-αGal antibodies in an individual; to detect the presence and/or amount of anti-αGal Ab in a biological sample; and can also be used in a method of performing a xenotransplantation in an individual. Reduction of circulating levels of anti-αGal antibody can be accomplished, using αGal conjugates of the invention, by inducing immunological tolerance to αGal and/or by neutralizing anti-αGal antibody. Neutralizing anti-αGal antibody can be achieved in vivo or ex vivo. With respect to all of these methods, the conjugate(s) (or composition comprising the conjugate(s)) may be used alone or in conjunction with other agents which promote the desired activity/objective. Various formulations and means of administration have been discussed above.

Inducing Immunological Tolerance in an Individual

The invention provides methods of inducing tolerance in an individual comprising administering an effective amount of any of the conjugate(s) (or compositions comprising the conjugate(s)) described herein. It is understood that, for purposes of this invention, that the immune response to be reduced (and/or eliminated, stabilized, and or rate of increase reduced), via inducing tolerance, is an immune response to αGal. Accordingly, the tolerance induced is antigen specific, wherein the antigen is αGal.

Determination of whether tolerance has been induced may be achieved by any means known in the art. In general, tolerance is determined by measuring the immune response, which can be measured using standard assays, including, for example, measuring serum levels of anti-αGal antibody; measuring anti-αGal Ab-producing B cells by ELISpot assay; measuring cytokine production following immunization with αGal (or αGal conjugate); performing in vitro analyses of T-cell response to αGal (or αGal epitope) after administration of αGal or conjugates thereof using T cells from the individual receiving such administration, including, for example, standard assays such as $^3$H-thymidine uptake to measure proliferation of T cells when presented with αGal (or αGal epitope) in the context of an antigen-presenting cell, standard $^{51}$Cr release assays to measure killing by cytotoxic T cells of a cell presenting αGal (or αGal epitope), and the like.

Immunological tolerance in B cells toward αGal can occur, for example, by anergy, or as a result of apoptosis. Regardless of the mechanism, B cell tolerance results in a reduction in, or loss of, the ability of B cells to produce, express on their surface and/or secrete anti-αGal antibody. To determine whether a reduction or loss of the ability of B cells to produce, express on their surface and/or secrete anti-αGal Ab, B cells can be obtained from, for example a primary or secondary lymphoid organ such as spleen or lymph node, or blood, and production of anti-αGal antibody measured. If the anti-αGal antibody is secreted, it can be measured by an immunoassay such as ELISA, using, for example an immobilized αGal conjugate of the invention, and detecting bound anti-αGal antibody using an appropriate labelled second antibody, such as an anti-isotype antibody. Anti-αGal antibody present on the surface of a B cell can be measured by FACS, using labelled anti-human IgM antibody or, alternatively, labelled αGal conjugate.

Reducing circulating anti-αGal antibodies in an individual The invention further provides methods of reducing circulating levels of anti-αGal antibody in an individual, comprising administering an effective amount (i.e., an amount sufficient to reduce antibody levels) of any of the conjugate(s) (or compositions comprising the conjugate(s)) described herein.

Determination of reduction of circulating levels of αGal antibodies may be achieved using standard assays in the art, such as ELISA. Preferably, the reduction (as compared to an earlier measured level) is at least about any of the following: 10%, 20%, 30%, 40%, 50%. The extent of reduction desired will depend on a number of factors, including, but not limited to, condition of the individual; whether other agent (s) are or will be used; nature of the transplant tissue.

Reducing Levels of Anti-αGal Antibody in Fluids Ex Vivo

In some embodiments, reduction of levels of circulating anti-αGal antibody is performed ex vivo. Accordingly, this invention provides methods for reducing levels of anti-αGal antibodies in a biological fluid of an individual, comprising contacting the fluid with an αGal conjugate of the invention ex vivo under conditions that permit the antibodies to bind epitopes on the platform. Suitable bodily fluids include those that can be returned to the individual, such as blood, plasma, or lymph.

Affinity adsorption apheresis is described generally in Nilsson et al. (1981) *Blood* 58(1):38–44; Christie et al. (1993) *Transfusion* 33:234–242; Richter et al. (1997) *ASAIO*

J. 43(1):53–59; Suzuki et al. (1994) *Autoimmunity* 19: 105–112; U.S. Pat. No. 5,733,254; Richter et al. (1993) *Metabol. Clin. Exp.* 42:888–894; Richter et al. (1997) *ASAIO J.* 43(1):53–59; and Wallukat et al. (1996) *Int'l J. Card.* 54:191–195. Any of these methods can be used.

In the methods of the invention, the bodily fluid is removed from the individual for extracorporeal binding to an αGal conjugate of this invention comprising epitopes reactive with anti-αGal antibody. For example, apparatuses and methods for removing blood and separating it into its constituent components are known in the art (see, e.g., U.S. Pat. Nos. 4,086,924; 4,223,672). The blood or portions thereof are then exposed to an αGal conjugate. The αGal conjugate neutralizes anti-αGal antibody, and the blood components are then optionally returned to the individual.

In a preferred technique, the anti-αGal-αGal conjugate complex is removed before the fluid is returned to the individual. This may be done, for example, by using a carrier attached to a solid phase, or by using a soluble carrier and selectively removing the complex from the treated solution.

To create a solid phase, an αGal conjugate can be adapted to render it insoluble. For example, where αGal conjugate comprises one of the platforms listed above, then the platform can be chemically adapted during synthesis to include an additional reactive group in the core structure. For example, an additional linkage can be added to a triethlyene glycol structure present in the core. The linkage is then used to attach the platform to an insoluble structure, such as a polystyrene or polyethylene bead, a polycellulose membrane, or other desirable structure. Commercially available matrices include agarose (a neutral linear polysaccharide generally composed of D-galactose and altered 3,6-anhydrogalactose residues, for example Sepharose™, Pharmacia), activated gels, nitrocellulose, borosilicate, glass fiber filters, silica, polyvinylchloride, polystyrene, and diazotized paper. Methods for preparing peptide-peptide conjugates are described in Hermanson, G. T., "Bioconjugate Techniques", Academic Press: New York, 1996; and in "Chemistry of Protein Conjugation and Cross-linking" by S. S. Wong, CRC Press, 1993. The biological fluid to be treated is simply treated with the solid phase, and antibodies in the fluid complex to the solid phase. The supernatant fluid can then be removed from the solid phase for return to the individual. In some instances, the solid phase can also be cleared of antibody for repeat use by using a suitable wash, providing both the epitope and the carrier is resistant to the washing solution. Suitable washing solutions may include 0.1 M glycine buffer, pH 2.4, dilute acetic acid, or 1 M KSCN buffered to ~pH 7.

If the αGal conjugate is not part of a solid phase, then the antibody-αGal conjugate complex can be removed from the fluid by any other appropriate method, including but not limited to microfiltration, antibody capture, or precipitation. Solutions suitable to cause precipitation of the complex depend on the solubility of the complex, and may include ammonium sulfate or polyethylene glycol. If the fluid is to be returned to the individual, then the precipitating solution should be chosen so that any that remains in the fluid does not cause an adverse reaction in the individual. Methods of returning blood to the individual are well-known in the art. Two processes commonly used are continuous and discontinuous processes. The continuous process involves removing the blood of an individual in a steady flow, separating the plasma from the cellular components, treating the plasma, recombining the plasma with the cellular component and then reinfusing the individual. The discontinuous process involves removing a small volume of blood, separating the plasma from the cellular components of that particular volume, treating the plasma of that volume, reconstituting the two components and reinfusing the volume into the individual.

This disclosure contemplates devices which can be used for reducing the level of anti-αGal antibody in a biological fluid using an αGal conjugate of this invention. Typically, the device will be a flow system, comprising the following elements: a) a port that permits biological fluid to flow into the device; b) a chamber in which the fluid is permitted to contact the αGal conjugate (optionally in a solid phase); c) a port that permits the treated fluid to flow out of the device. Such devices can be designed as continuous flow systems, and as systems that permit the treatment of a single sample from an individual for purposes of analysis or readministration at a subsequent time.

Neutralizing Anti-αGal Antibodies

The invention also provides methods of neutralizing circulating levels of anti-αGal antibodies in an individual, comprising administering an effective amount of any of the conjugates described herein to the individual, wherein an effective amount is an amount sufficient to neutralize circulating levels of anti-αGal antibodies. Not all circulating anti-αGal antibodies need be neutralized. Methods of detecting binding of conjugate to circulating anti-αGal antibodies may be performed using methods standard in the art and described below. For example, a blood sample may be obtained from an individual who has received a conjugate described herein, and levels of anti-αGal antibodies (as detected by using the same epitope as used on the conjugate) may be compared to initial level of anti-αGal antibodies (i.e., before administration). A lowering of levels indicates that anti-αGal antibodies are being neutralized. Because neutralization should occur relatively quickly upon administration of conjugate, such measurements are preferably taken within 1 day, preferably within about 12 hours, more preferably within about 10 hours, more preferably within about 8 hours, more preferably within about 4 hours of administration of conjugate.

Detecting Presence And/or Amount of Anti-αGal Antibody

The invention further provides methods for detecting the presence of and/or quantitating the amount of anti-αGal antibody in a biological sample comprising (a) contacting an αGal conjugate of the invention with the biological sample under conditions that permit the formation of a stable antigen-antibody complex; and (b) detecting stable complex, if any, formed in step (a). Current detection methods employ αGal epitopes coupled to a protein carrier, so that the epitope recognized by any given antibody could also include the αGal epitope plus one or more amino acids, the identity of which could vary widely, depending upon where the linkage to the protein carrier occurred. In addition, the valency of such αGal-protein conjugates is highly variable. The conjugates of the present invention, in contrast, are defined, both in terms of structure and valency, and thus confer a major advantage in a diagnostic assay, such as an ELISA, in that one would be detecting only anti-αGal Ab, and standard curves generated with αGal conjugates of the invention would be more uniform, i.e., less subject to lot-to-lot variation.

In one embodiment, the invention provides methods of detecting an antibody that specifically binds to an αGal epitope(s) in a biological sample. These methods are generally applicable in the clinical setting, for example, for diagnosing and/or monitoring anti-αGal antibody levels in an individual. These methods entail contacting (anti-αGal) antibody in the sample with an αGal conjugate (i.e., any conjugate of this invention) under conditions suitable to allow the formation of a stable complex between anti-αGal antibody (such as an anti-αGal antibody reactive with donor tissue/organ) and an αGal epitope(s), and detecting a stable complex formed, if any. The αGal conjugates of the invention render these methods particularly useful, as no generally convenient or suitable assay for these antibodies has yet been developed. A number of immunoassay methods are known in the art and need not be described in detail.

An anti-αGal antibody may be expressed on the surface of a B cell. Accordingly, in another embodiment, the invention provides methods of detecting a B cell expressing an anti-αGal antibody on its surface. These methods entail contacting (anti-αGal) antibody-expressing B cells in a biological sample with an αGal conjugate (i.e., any conjugate of this invention) under conditions suitable to allow the formation of a stable complex between anti-αGal antibody (such as an anti-αGal antibody reactive with donor tissue/ organ) and an αGal epitope(s), and detecting a stable complex formed, if any.

Suitable samples in which to measure αGal antibody are biological samples, including serum or plasma (preferably serum) and donor tissue eluate. For detection of anti-αGal antibody-expressing B cells, suitable samples include whole blood, which has preferably been treated to remove red blood cells. It is well understood in the art that detection of a complex formed may be direct (such as by measuring the amount of label associated with a complex) or indirect (such as in measuring the amount of labeled ligand which is displaced during the assay).

To use an αGal conjugate of this invention in the detection of such antibodies in an individual, an immunoassay is conducted. The αGal conjugate is provided as a reagent, and the anti-αGal antibody is the target in the biological sample. For example, human IgG antibody molecules present in a serum sample may be captured with solid-phase protein A, and then overlaid with the labeled polypeptide reagent. The amount of antibody would then be proportional to the label attached to the solid phase. Alternatively, cells or tissue sections expressing αGal may be overlaid first with the test sample containing the antibody, and then with a detecting reagent such as labeled anti-immunoglobulin. The amount of antibody would then be proportional to the label attached to the cells. The amount of antibody detected in the sample would be compared with the amount detected in a control sample.

To detect anti-αGal antibody-expressing B cells, after formation of a stable complex between a B cell and a suitably labeled αGal conjugate of the invention, the complex can be detected by, for example, fluorescence activated cell sorting (FACS) analysis. Suitable sources of B cells include, but are not limited to, blood, or a secondary lymphoid organ such as spleen or lymph node.

In the methods of the invention, an αGal conjugate will typically be immobilized, by known techniques, onto a suitable solid phase, such as affinity column packing material, or a plastic surface such as a microtiter plate or a dipstick. Appropriate affinity column packing materials include, for example, a beaded agarose matrix, polyacrylamide, glass, cellulose or cross-linked dextran. Suitable plastic surfaces include polymethacrylate, polystyrene, polyethylene, polyterepthalate, ethylene glycol, polyester, polypropylene, and the like. Generally, any standard microtiter plate may be used. Alternatively, the solid phase may be in the form of a gel or matrix into which the αGal conjugate is incorporated.

For further illustration, a test sample potentially containing an antibody that specifically binds to an αGal epitope(s) can be mixed with a pre-determined non-limiting amount of the αGal conjugate which is generally detectably labeled (such as with a radioisotope or enzyme). In a liquid phase assay, unreacted reagents are removed by a separation technique, such as filtration or chromatography. In these immunoassay techniques, the amount of label associated with the complex positively correlates with the amount of anti-αGal antibody present in the sample. Similar assays can be designed in which anti-αGal antibody in the test sample compete with labeled antibody for binding to a limiting amount of the αGal conjugate. Here, the amount of label negatively correlates with the amount of anti-αGal antibody in the sample.

In some embodiments, the biological sample is a tissue sample, or a tissue eluate, and the amount of anti-αGal antibody associated with the tissue sample is measured by, for example, a competitive binding assay. These methods may be especially useful in those contexts in which a particular tissue should be tested and/or monitored for presence and/or amount of anti-αGal antibody. This type of assay may indicate, for example, whether a particular disease (or risk of disease) may be indicated (such as a particular form of thrombosis or clotting disorder). Such an assay may also be useful in providing more precise and sensitive determination of localization of anti-αGal antibody for diagnostic and/or monitoring purposes. Further, localization information about anti-αGal antibody may also provide a clinician with indication about suitable treatment options.

It is understood that these detection methods are applicable in a variety of clinical contexts. For instance, detection may be used to identify individuals who show. risk of developing anti-αGal antibody-associated conditions or disorders, such as xenoplant rejection, which may in turn arise from being unable to distinguish antibodies associated with pathology and those not associated with pathology. Detection may also be used to monitor treatment (such as administration of any of the compositions described above). Detection may also assist in distinguishing between pathogenic antibodies from non-pathogenic antibodies. Detection may also assist the clinician in deciding the best treatment options and/or prognosis.

Performing Xenotransplantation

The invention also provides methods of performing a xenotransplantation in an individual, comprising (a) introduction of αGal-bearing tissue to the individual; and (b) administering an effective amount of any of the conjugate(s) (or compositions comprising the conjugate(s) described herein) to the individual. Methods of transplantation, such as surgical transplantation, are known in the art and need not be described herein. Any αGal-bearing tissue (i.e., tissue which contains, or is believed to contain, αGal on at least part of its surface (i.e., surface cells of the tissue)) may be used, including, but not limited to, kidney; liver; pancreas; lung; heart; lung-heart block transplants; cells, including, but not limited to, insulin-producing cells of the pancreas, and fetal neural cells (e.g., dopamine-producing brain cells for treating Parkinson's disease). The source of these tissues may vary, and generally are from pig. Administration of conjugates and compositions has been discussed above. Preferably, the conjugate(s) is administered to the individual prior to introduction of αGal-bearing tissue. Accordingly, the transplantation methods of the invention also include administering a conjugate described herein at least about any of the following prior to introduction of tissue: 5 days, 10 days, 15 days, 20 days, 30 days, 45 days, 50 days, 60 days. The relationship between administration of conjugate and introduction of αGal-bearing tissue will depend on several factors, including but not limited to, the conjugate used, the tissue introduced, and/or the individual's condition (including medical history).

As is understood by one skilled in the art, an αGal-bearing tissue includes αGal-bearing cells, and, as such, the xenotransplantation methods of the invention include administration of αGal-bearing cells.

The invention also includes methods of suppressing rejection of a transplanted αGal-bearing tissue in an individual, comprising administering any of the conjugates described herein to the individual in an amount sufficient to suppress rejection. Indicia of rejection have been discussed herein. "Suppressing" rejection means any one or more of the following states: slowing, delaying, stopping rejection. "Suppressing" rejection indicates an extent of rejection that is reduced or curtailed compared to the extent of rejection without administering the conjugate, i.e., that the extent of rejection at a given time point is reduced when compared to otherwise same conditions except for receiving the conjugate. Preferably, the conjugate is compound 46 (LJP 920). Administration, formulations, and αGal bearing tissues have been discussed above, including the discussion of transplantation methods. Conjugate may be administered before and/or after the individual receives the αGal bearing tissue. The dosage may vary depending, inter alia, on whether a conjugate is used in conjunction with another agent(s) designed to suppress rejection, such as an immunosuppressant.

The following examples are provided to illustrate but not limit the present invention.

EXAMPLES

Example 1

Synthesis of αGal Epitopes

The general analytical methods and characterization techniques used in the present disclosure are identified below. NMR spectra were recorded on a Bruker AC300 spectrometer at 300 MHz for $^1$H and 75 MHz for $^{13}$C. Chemical shifts were recorded in parts per million (δ) relative to TMS (i.e., tetramethylsilane, δ=0.0 ppm) or to the residual signal of deuterated solvents: chloroform (δ=7.27 ppm for $^1$H; δ=77.23 ppm for $^{13}$C), methanol (δ=4.87 ppm for $^1$H; δ=49.15 ppm for $^{13}$C) and D$_2$O (δ=4.80 (DSS) ppm for $^1$H). Couplin constants (j) are reported in hertz. Analytical HPLC analyses were performed on a Hewlett Packard liquid chromatography HP 1090 instrument fitted with a Vydac C18 column (4.6×250 mm, 5 µm particle size). Preparative HPLC was performed on Dynamax SD 200 system with Vydac C18 column (22×250 mm, 10 µm particle size). Mass spectra were recorded on Finnigan LCQ mass spectrometer.

Enzymatic Synthesis of the αGal Epitope, 2-[2-(2-thioethoxy)ethoxy]ethyl 3-O-(α-D-galactopyranosyl)-β-D-galactopyranoside: A reaction scheme illustrating the synthesis is shown in FIG. 1.

Compound 2

S-2-[2-(2-Hydroxylethoxy)ethoxy]ethyl Thiobenzoate

To a mixture of 2-[2-(2-cloroethoxy)ethoxy]ethanol, compound 1 (20 g, 0.12 mol) and thiobenzoic acid (16.4 g, 0.12 mol) was added 12 g of triethylamine at room temperature. The mixture was then stirred at 90° C. for 1 h. After cooled to room temperature, ethyl acetate (100 mL) was added to the reaction mixture and filtered. The filtrate was concentrated and purified via silica gel chromatography (hexane/ethyl acetate, 1:1) to give compound 2 (30.6 g, 95%) as an orange syrup: $^1$H NMR (CDCl$_3$): δ 7.97 (dd, J=8.3, 1.4, 2 H), 7.56 (d, J=7.4, 1 H), 7.45 (t, J=6.9, 2 H), 3.73 (m, 4 H), 3.68 (s, 4 H), 3.62 (m, 2 H), 3.31 (t, 2 H).

Compound 4

2-[2-(2-Benzoylthioethoxy)ethoxy]ethyl 2,3,4,6-tetra-O-acetyl-β-D-galactopyranoside To a solution of compound 2 (7.79 g, 28.9 mmol) and acetobromo-α-D-galactose, compound 3 (17.80 g, 43.28 mmol) in dry CH$_2$Cl$_2$ (100 mL) were added Ag$_2$CO$_3$ (9.27 g, 36.1 mmol) and activated 4 Å molecular sieve (powder, 10 g) at 0° C. After stirred at room temperature for 3 d, the reaction mixture was filtered through Celite and the filtrate was concentrated and purified via silica gel chromatography (hexane/ethyl acetate, 4:1) to give compound 4 (12.29 g, 71%) as a colorless syrup: $^1$H NMR (CDCl$_3$): δ 7.99–7.95 (m, 2 H), 7.61–7.55 (m, 1 H), 7.48–7.43 (m, 2 H), 5.39 (dd, J=1.0,3.4, 1 H), 5.21 (dd, J=7.9, 10.5, 1 H), 5.03 (dd, J=3.4, 10.5, 1 H), 4.58 (d, J=7.9, 1 H), 4.14 (dd, J=2.9, 6.9, 1 H), 3.99–3.89 (m, 2 H), 3.79–3.65 (m, 10 H), 3.30 (t, J=6.4,2 H), 2.15–1.98 (4s, 12 H); $^{13}$C NMR (CDCl$_3$): δ 191.4, 170.3, 170.2, 170.0, 169.4, 136.9, 133.4, 128.5, 127.2, 101.3, 97.4, 70.9, 70.6, 70.5, 70.3, 69.8, 69.0, 68.8, 67.0, 61.2, 20.7, 20.6, 20.5; MS (ESI): m/e (M+Na$^+$) Calcd. for C$_{27}$H$_{36}$O$_{13}$SNa: 623.2, obsd.: 623.2.

Compound 6

2-[2-(2-tert-Butyldithioethoxy)ethoxy]ethyl β-D-galactopyranoside

To a stirred solution of compound 4 (3.47 g, 5.77 mmol) in methanol (15 mL) was added NaOCH$_3$ (0.50 g, 9.28 mmol) at 0° C. After 3 h, diethyl 1-(tert-bytylthio)-1,2-hydrzainedicarboxylate, compound 5 (2.2 g, 8.3 mmol), which was prepared as described (Wunsch, E., et al. *Hoppe-Seyler's Z. Physiol. Chem.* 1982, 363, 1461–1464), was added. The reaction mixture was stirred at room temperature for another 2 h. Dowex 50X2-400 resin was then added to neutralized the solution and filtered. The filtrate was concentrated and purified via silica gel chromatography (CH$_2$Cl$_2$/MeOH, 9:1) to give compound 6 (1.22 g, 51%) as a white solid: $^1$H NMR (CDCl$_3$): δ 4.39 (br s, 1 H), 4.35 (br d, 2 H), 4.11 (br s, 1 H), 4.02 (br s, 2 H), 3.84 (br s, 2 H), 3.78–3.48 (m, 13 H), 2.89 (t, J=6.7, 2 H), 1.33 (s, 9H); MS (ESI): m/e (M+1) Calcd. for C$_{16}$H$_{33}$O$_8$S$_2$: 417.2, obsd.: 417.5.

Compounds 7 and 8

2-[2-(2-tert-Butyldithioethoxy)ethoxy]ethyl 3-O-(α-D-galactopyranosyl)-β-D-galactopyranoside(7)

2-[2-(2-tert-Butyldithioethoxy)ethoxy]ethyl 3-O-(α-D-galactopyranosyl)-p-D-galactopyranoside (8)

To a solution of compound 6 (2.87 g, 6.89 mmol) and p-nitrophenyl α-D-galactopyranoside (200 mg) in 10 mL of sodium phosphate buffer (50 mM, pH 6.5) was added 20 mg of coffee bean α-galactosidase. The reaction was proceeded at room temperature with gradual addition of donor until 300 mM p-nitrophenol had been formed (3 d). The reaction mixture was lyophilized and the residue was suspended in methanol, filtered and concentrated. The unreacted starting material (2.5 g) was recovered by silica gel chromatography ($CH_2Cl_2$/MeOH, 95:5 to 70:30). The products were first purified on P2 Gel filtration column eluted with water and then on reverse phase HPLC column to yield compound 7 (80 mg, 2.0%) and compound 8 (106 mg, 2.6%) as white solids. For compound 7: analytical RF-HPLC: $t_R$ 8.49 min with a gradient of 25 to 30% ACN in $H_2O$ at a flow rate of 1 mL/min, purity, 100%; $^1$H NMR ($CD_3OD$): 5.04 (d, J=1.9, 1 H), 4.32 (dd, J=1.6, 6.2, 1 H), 4.25 (t, J=5.5, 1 H), 4.05–4.00 (m, 2 H), 3.93 (d, J=1.2, 1 H), 3.83–3.61 (m, 17 H), 3.52 (t, 1 H), 2.89 (t, J=6.6, 2 H), 1.33 (s, 9H); MS (ESI): m/e (M+Na$^+$) Calcd. for $C_{22}H_{42}O_{13}S_2Na$: 601.2, obsd.: 601.2. For compound 8: analytical RF-HPLC: $t_R$ 7.14 min with a gradient of 25 to 30% ACN in $H_2O$ at a flow rate of 1 mL/min, purity, 100%; $^1$H NMR ($CD_3OD$): 4.27(d, J=7.5, 1 H), 4.00–3.62 (m, 22 H), 3.50 (m, 1 H), 2.89 (t, J=6.6, 2 H), 1.36 (s, 9 H); MS (ESI): m/e (M+Na$^+$) Calcd. for $C_{22}H_{42}O_{13}S_2Na$: 601.2, obsd.: 601.1.

These two disaccharides were further characterized after acetylated with $Ac_2O$ in pyridine at room temperature overnight: for acetylated compound 7: $^1$H NMR ($CDCl_3$): δ 5.46 (br d, J=3.3, 1 H), 5.37 (br d, J=3.3, 1 H), 5.31–5.22 (m, 3 H), 5.14 (dd, J=3.3, 10.2, 1 H), 4.50 (d, J=7.8, 1 H), 4.29 (br t, J=6.5, 7.3, 1 H), 4.21 (dd, J =7.3, 11.3, 1 H), 4.14 (d, J=7.3, 2 H), 4.04 (dd, J=6.5, 10.8, 1 H), 3.91 (dd, J=10.4, 2.9, 1 H), 3.84 (br t, J=7.3, 1 H), 3.87–3.62 (m, 10 H), 2.91 (t, J=7.6, 2 H), 2.15–1.95 (7s, 21 H), 1.35 (s, 9 H) and for acetylated compound 8: $^1$H NMR ($CDCl_3$): δ 5.42 (br d, J=3.1, 1 H), 5.41 (br d, J=3.0, 1 H), 5.28 (dd, J=3.0, 10.4, 1 H), 5.19 (dd, J=7.8, 10.4, 1 H), 5.12(dd, J=3.3, 10.4, 1 H), 5.02 (dd, J=3.1, 10.4, 1 H), 4.93 (d, J=3.3, 1 H), 4.57 (d, J=7.8, 1 H), 4.21 (br t, J=6.8, 1 H), 4.09 (m, 2 H), 3.95 (dt, J=3.9, 10.8, 1 H), 3.86 (br t, J=6.6, 1 H), 3.81–3.62 (m, 10 H), 3.44 (dd, J=7.4, 10.2, 1 H), 2.89 (t, J=6.7,2 H), 2.12–1.98 (7s, 21 H), 1.35 (s, 9 H).

Figure 2:
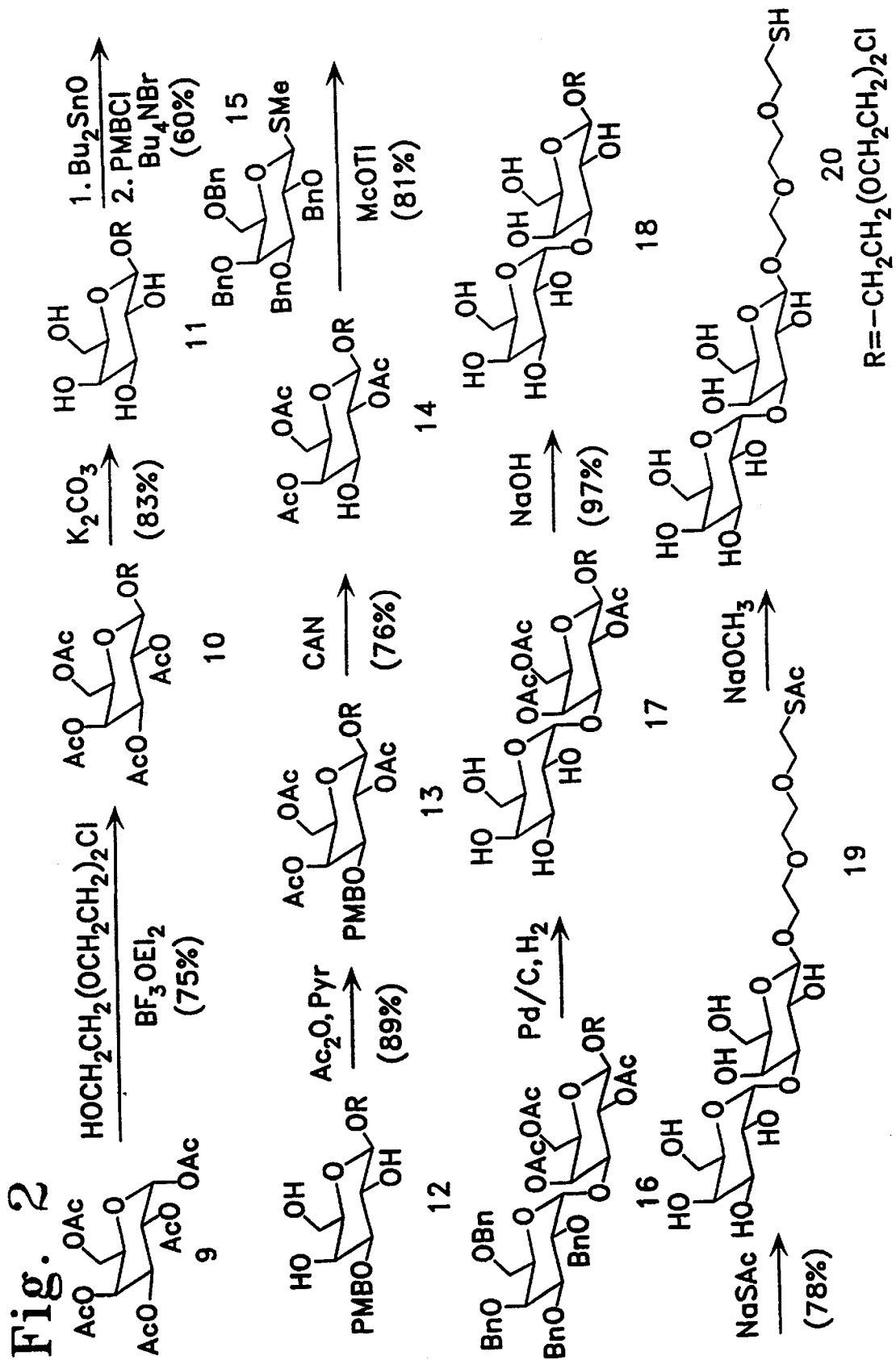
FIG. 2 is a reaction scheme illustrating the chemical synthesis of the αGal epitope, 2-[2-(2-thioethoxy)ethoxy] ethyl 3-O-(α-D-galactopyranosyl)-β-D-galactopyranoside.

Chemical synthesis of the αGal epitope, 2-[2-(2-thioethoxy)ethoxy]ethyl 3-O-(α-D-galactopyranosyl)-β-D-galactopyranoside: A reaction scheme illustrating this synthesis is shown in FIG. 2.

Compound 10

2-[2-(2-Chloroethoxy)ethoxy]ethyl 2,3,4,6-tetra-O-acetyl-β-D-galactopyranoside

To a mixture of galactose pentaacetate, compound 9 (70 g, 179 mmol), 2-[2-(2-chloroethoxy)ethoxy]ethanol (45.4 g, 270 mmol) and activated 4 Å molecular sieve (20 g) in dry $CH_2Cl_2$ (500 mL) was added $BF_3Et_2O$ (52 g, 370 mmol) dropwise at room temperature for 3 h. After stirred for 2 d, the suspension was filtered through Celite and the filtrate was poured into 300 mL of saturated aqueous $NaHCO_3$ cooled in an ice bath. The organic phase was separated and the aqueous phase was extracted with $CH_2Cl_2$. The combined organic phases were washed with brine, dried, and concentrated. The residue was purified via silica gel chromatography (hexane/ethyl acetate, 1:1) to give compound 10 (67 g, 75%) as a colorless oil: $^1$H NMR ($CDCl_3$): δ 5.36 (d, J=3.2, 1 H), 5.19 (dd, J=10.4, 8.0, 1 H), 5.00 (dd, J=10.4, 3.6, 1 H), 4.55 (d, J=8.0, 1 H), 4.18–4.08 (m, 3 H), 391–3.87 (m, 2 H), 3.74 (m, 2H), 3.72–3.61 (m, 8 H), 2.13 (s, 3 H), 2.04 (s, 3 H), 2.03 (s, 3 H), 1.96 (s, 3 H).

Compound 11

2-[2-(2-Chloroethoxy)ethoxy]ethyl β-D-galactopyranoside

A solution of compound 10 (67 g, 134 mmol) in 200 mL of methanol and 250 mL of 1 M $K_2CO_3$ aqueous solution was stirred at room temperature overnight. The reaction mixture was poured into 700 mL of methanol cooled with ice-water bath. The precipitate was filtered through celite and washed with methanol. The filtrate was combined and neutralized with Dowex resin (H form) until pH 6. The resin was filtered and washed with water. The filtrate was concentrated and lyophilized to give compound. 11 (37 g, 83%) as a colorless oil: $^1$H NMR ($D_2O$): δ 4.30 (d, J=7.2, 1 H), 3.95 (m, 1 H), 3.80 (d, J=3.6, 1 H), 3.80–3.50 (m, 15 H), 3.40 (m, 1 H).

Compound 12

2-[2-(2-Chloroethoxy)ethoxy]ethyl 3-O-p-methoxybenzyl-β-D-galactopyranoside

A mixture of compound 11 (37 g, 112 mmol) and dibutyltin oxide (46 g, 210 mmol) in dry MeOH (300 mL) was refluxed under nitrogen until clear (10 hr). The reaction mixture was concentrated and the residue was dried under vacuum. The residue was dissolved in 800 mL of dioxane and 80 mL of DMF and p-methoxybenzyl chloride (32 g, 28 ml, 0.20 mol) was added. The resulting mixture was stirred at 100° C. for 10 h to give a brownish solution with precipitate. After cooled to room temperature, the precipitate was removed by filtration through Celite and washed with dioxane (100 mL) and chloroform (100 mL). The combined organic phases were concentrated and purified by silica gel chromatography (ethyl acetate) to give compound 12 (30 g, 60%) as a colorless oil.

Compound 13

2-[2-(2-Chloroethoxy)ethoxy]ethyl 2,4,6-tri-O-acetyl-3-O-p-methoxybenzyl β-D-galactopyranoside Compound 12 (30 g, 66.5 mmol) was acetylated with $Ac_2O$ (150 mL) in pyridine (150 mL), catalyzed by DMAP (120 mg). After stirred for 5 h, the reaction mixture was concentrated. The residue was dissolved in chloroform (300 mL) and washed with HCl solution (0.5 M), water, saturated aqueous $NaHCO_3$ and brine. The organic phase was dried over anhydrous $Na_2SO_4$ and concentrated to give compound 13 (34 g, 89%) as a colorless oil: $^1$H NMR ($CDCl_3$): δ 7.19 (d, J=8.6, 2 H), 6.87 (d, J=8.6,2 H), 5.48 (d, J=3.3, 1 H), 5.10 (dd, J=10.0,8.1, 1 H), 4.62 (d, J=11.6, 1 H), 4.45 (d, J=8.1, 1 H), 4.34 (d, J=11.6, 1 H), 4.17 (dd, J=6.7, 1.0, 2 H), 3.94 (m, 1 H), 3.82–3.61 (m, 15 H), 3.49 (dd, J=10.0, 3.3, 1 H), 2.16 (s, 3 H), 2.08 (s, 3 H), 2.04 (s, 3 H); MS (ESI): m/e (M+Na$^+$) Calcd. for $C_{26}H_{37}ClO_{12}Na$: 599.2, obsd: 599.4.

Compound 14

2-[2-(2-Chloroethoxy)ethoxy]ethyl 2,4,6-tri-O-acetyl β-D-galactopyranoside

To a solution of compound 13 (34 g, 59 mmol) in 300 mL of $CH_3CN$/water (9:1) was added CAN (64 g, 120 mmol) slowly during 3 h at 0° C. After addition, the mixture was stirred at the same temperature for 3 h. The reaction mixture was then concentrated, diluted with 250 mL of water, and extracted with chloroform. The organic extracts were washed with saturated aqueous $NaHCO_3$ and brine, dried over anhydrous $Na_2SO_4$, and concentrated. The residue was purified via flash column chromatography (hexane/ethyl acetate, 3:1 to 2:3) to give compound 14 (20.4 g, 76%) as a colorless oil: $^1$H NMR ($CDCl_3$): δ 5.31 (d, J=3.6, 1 H), 4.95 (dd, J=10.0, 7.8, 1 H), 4.51 (d, J=8.0, 1 H), 4.13 (m, 2 H), 3.94 (m, 1 H), 4.00–3.61 (m, 14 H), 2.15 (s, 3 H), 2.11 (s, 3 H), 2.04 (s, 3 H).

Compound 16

2-[2-(2-Chloroethoxy)ethoxy]ethyl 3-O-(2,3,4,6-tetra-O-benzyl-α-D-galactopyranosyl)-2,4,6-tri-O-acetyl-β-D-galactopyranoside

To a mixture of compound 14 (10 g, 22 mmol), compound 15 (25.4 g, 45 mmol), 4-methyl-2,6-di-t-butyl pyridine (6.8 g, 33 mmol), and activated 4 Å molecular sieve (10 g) in dry ether (300 mL) was added a solution of methyl triflate (7.2 mL) in ether (50 mL) dropwise via a syringe-pump over a period of 24 h. After stirred at room temperature for 36 h, the reaction mixture was filtered through Celite. The filtrate was concentrated and purified via silica gel chromatography (hexane/ethyl acetate, 4:1 to 1:1) to give compound 16 (17.3 g, 81%) as a yellowish oil: $^1$H NMR (CDCl$_3$): δ 7.35–7.22 (m, 20 H), 5.43 (d, J=3.2, 1 H), 5.16 (dd, J=10.0, 8.0, 1 H), 5.06 (d, J=3.4, 1 H), 4.90 (d, J=11.6, 1 H), 4.81 (d, J=12.0, 1 H), 4.68–4.62 (m, 3 H), 4.46–4.39 (m, 4 H), 4.12–3.59 (m, 20 H), 3.49 (d, J=6.4, 2.03 (s, 3 H), 1.94 (s, 3 H), 1.79(s, 3 H); MS (ESI): m/e (M+Na$^+$) Calcd. for C$_{52}$H$_{63}$ClO$_{16}$Na: 1001.4, obsd: 1001.8.

Compound 17

2-[2-(2-Chloroethoxy)ethoxy]ethyl 3-O-α-D-galactopyranosyl-2,4,6-tri-O-acetyl-β-D-galactopyranoside

A mixture of compound 16 (18.1 g, 18.5 mmol) and Pd/C (20%, 3 g) in 300 mL of methanol and 1.5 mL of acetic acid was shaken under compressed hydrogen (50 psi) at room temperature for 9 h. The reaction mixture was filtered through Celite and concentrated. Water (10 mL) was added to the residue to assist the removal of acetic acid and the crude product was used directly in next reaction without purification. $^1$H NMR (CD$_3$OD): δ 5.52 (dd, J=10.0, 8.4, 1 H), 4.98 (d, J=3.6, 1 H), 4.62 (d, J=8.0, 1 H), 4.14 (m, 2 H), 4.06 (m, 1 H), 3.98 (t, J=8.4, 1 H), 3.92 (m, 1 H), 3.86 (d, J=2.7, 1 H), 3.77–3.61 (m, 16 H), 3.55 (dd, J=10.0, 3.2, 1 H), 2.13 (s, 3 H), 2.11 (s, 3 H), 2.03 (s, 3 H). MS (ESI): m/e (M+Na$^+$) Calcd. for C$_{24}$H$_{39}$ClO$_{16}$Na: 641.2, obsd: 641.3.

Compound 18

2-[2-(2-Chloroethoxy)ethoxy]ethyl 3 -O-α-D-galactopyranosyl-β-D-galactopyranoside

A solution of compound 17 in 40 mL of 1 M NaOH and 300 mL of methanol was stirred at room temperature for 6 h. The reaction mixture was neutralized with Dowex resin (H form) to pH 6, filtered and lyophilized to give compound 18 (8.9 g, 97%) as a white solid. $^1$H NMR (D$_2$O): δ 5.18 (d, J=3.7, 1 H), 4.53 (d, J=7.7, 1 H), 4.25–3.68 (m, 24 H). MS (ESI): m/e (M+Na$^+$) Calcd. for C$_{18}$H$_{33}$ClO$_{13}$Na: 515.2, obsd: 515.5.

Compound 19

2-[2-(2-Acetylthioethoxy)ethoxy]ethyl 3-O-(α-D-galactopyranosyl)-β-D-galactopyranoside

A solution of compound 18 (8.9 g, 18.1 mmol) in 100 mL of 1 M potassium thioacetate was stirred at 95° C. under nitrogen for 36 h. The reaction mixture was cooled and loaded on a column packed with Dowex ion exchange resin (H form, 100 g) and eluted with water. The aqueous solution was neutralized with Dowex Marathon WBA anion exchange resin (from pH 2 to 5), filtered, and lyophilized to give compound 19 (7.5 g, 78%) as an off-white solid. $^1$H NMR (D$_2$O): δ 5.17 (d, J=3.8, 1 H), 4.52 (d, J=7.7 Hz, 1 H), 4.24–3.67 (m, 25 H), 3.15 (t, J=6.2,2 H); MS (ESI): m/e (M+Na$^+$) Calcd. for C$_{20}$H$_{36}$O$_{14}$SNa: 555.2, obsd: 555.3.

Compound 20

2-[2-(2-Thioethoxy)ethoxy]ethyl 3-O-(α-D-galactopyranosyl)-β-D-galactopyranoside

A mixture of compound 19 (650, 1.22 mmol) and 4 g of DOWEX 550A OH anion-exchange resin, pre-washed with methanol, in 50 mL of methanol was stirred at room temperature overnight. The reaction mixture was filtered and the resin was washed with 5% acetic acid in methanol. The filtrate was concentrated to give compound 20 (578 mg, 97%) as a white solid: $^1$H NMR (CD$_3$OD): δ 5.00 (d, J=3.6, 1 H), 4.35 (d, J=7.6 Hz, 1 H), 4.04 (m, 2H), 3.93 (m, 1 H), 3.84 (m, 1 H), 3.82 (dd,J=10.4, 3.2, 1 H), 3.73–3.51 (m, 18 H), 2.83 (t, J=6.0, 2 H); $^{13}$C NMR (D$_2$O): δ 103.2, 95.8, 77.8, 75.4, 72.7, 71.4, 70.2, 70.1, 69.9, 69.7, 69.2, 68.9, 68.7, 65.4, 61.5, 37.9, 23.5; MS (ESI): m/e (M+Na$^+$) Calcd. for C$_{18}$H$_{34}$O$_{13}$SNa: 513.5, obsd: 513.3.

The synthetically prepared αGal epitope on resin was antigenically active as demonstrated by its ability to remove >95% of anti-αGal Ig from normal rhesus monkey or human serum, as measured by FACS.

Compound 22 p-Aminophenyl 3-O-β-D-galactopyranosyl-α-D-galactopyranoside

Figure 3:
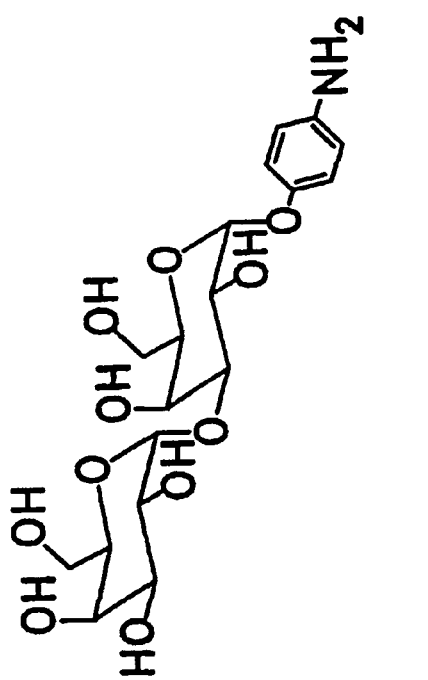
FIG. 3 is a reaction scheme illustrating the chemoenzymatic synthesis of the αGal epitope, p-aminophenyl 3-O-α-D-galactopyranosyl-α-D-galactopyranoside.
Figure 3:
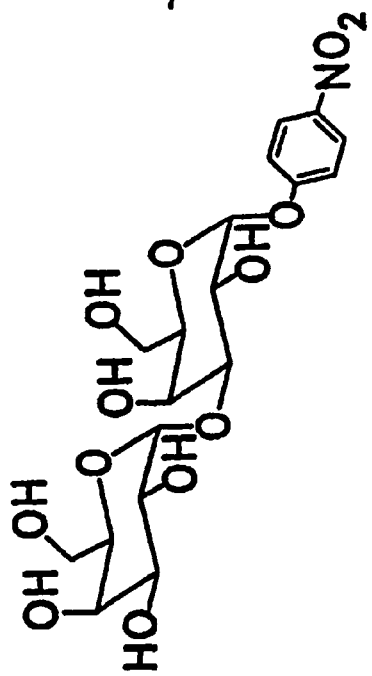

A reaction scheme illustrating the chemoenzymatic synthesis of the αGal epitope, p-aminophenyl 3-O-β-D-galactopyranosyl-α-D-galactopyranoside (22) is shown in FIG. 3. p-Nitrophenyl 3-O-α-D-galactopyranosyl-α-D-galactopyranoside (compound 21) was prepared enzymatically as described by Nilsson (Tetrahedron Lett. (1997) 38:133–136). A mixture of p-nitrophenyl 3-O-β-galactopyranosyl-α-D-galactopyranoside (70 mg, 0.15 mmol) and 10 mg Pd/C (10%) in methanol (4 mL) was stirred under hydrogen at room temperature overnight. The reaction mixture was then filtered through Celite and the filtrate was concentrated in vacuo to give (50 mg) as a yellowish solid: $^1$H NMR (CD$_3$OD): δ 6.87 (t, 2 H), 6.57 (d, 2 H), 5.21 (d, 1 H), 4.98 (d, 1 H), 4.2–4.1 (m, 2 H), 4.1–3.8 (m, 3 H), 3.8–3.7 (m, 3 H), 3.7–3.5 (m,4 H); $^{13}$C NMR (CD$_3$OD): δ 143.8, 120.1, 117.9, 115.4, 101.2, 97.6, 78.3, 77.0, 72.6, 71.5, 71.4, 70.3, 68.7, 67.4, 63.2, 62.6; MS (ESI): m/e (M+Na$^+$) Calcd. for C$_{18}$H$_{27}$NO$_{11}$Na: 456.2, obsd: 456.2.

Example 2

Synthesis of Valency Platforms

Synthesis of Compound 23

A solution of 1,4-diaminobutane and NaHCO$_3$ in water/dioxane 1/1 is treated with bromoacetic anhydride. The mixture is extracted with CH$_2$Cl$_2$, and the CH$_2$Cl$_2$ layer is dried and concentrated to give crude product which is purified by silica gel chromatography to give compound 23.

Synthesis of Compound 24

A solution of 4,7,10-trioxa- 1,3-tridecanediamine and NaHCO$_3$ in water/dioxane 1/1 is treated with bromoacetic anhydride. The mixture is extracted with CH$_2$Cl$_2$, and the CH$_2$Cl$_2$ layer is dried and concentrated to give crude product which is purified by silica gel chromatography to give compound 24.

Synthesis of Compound 29

Figure 24:
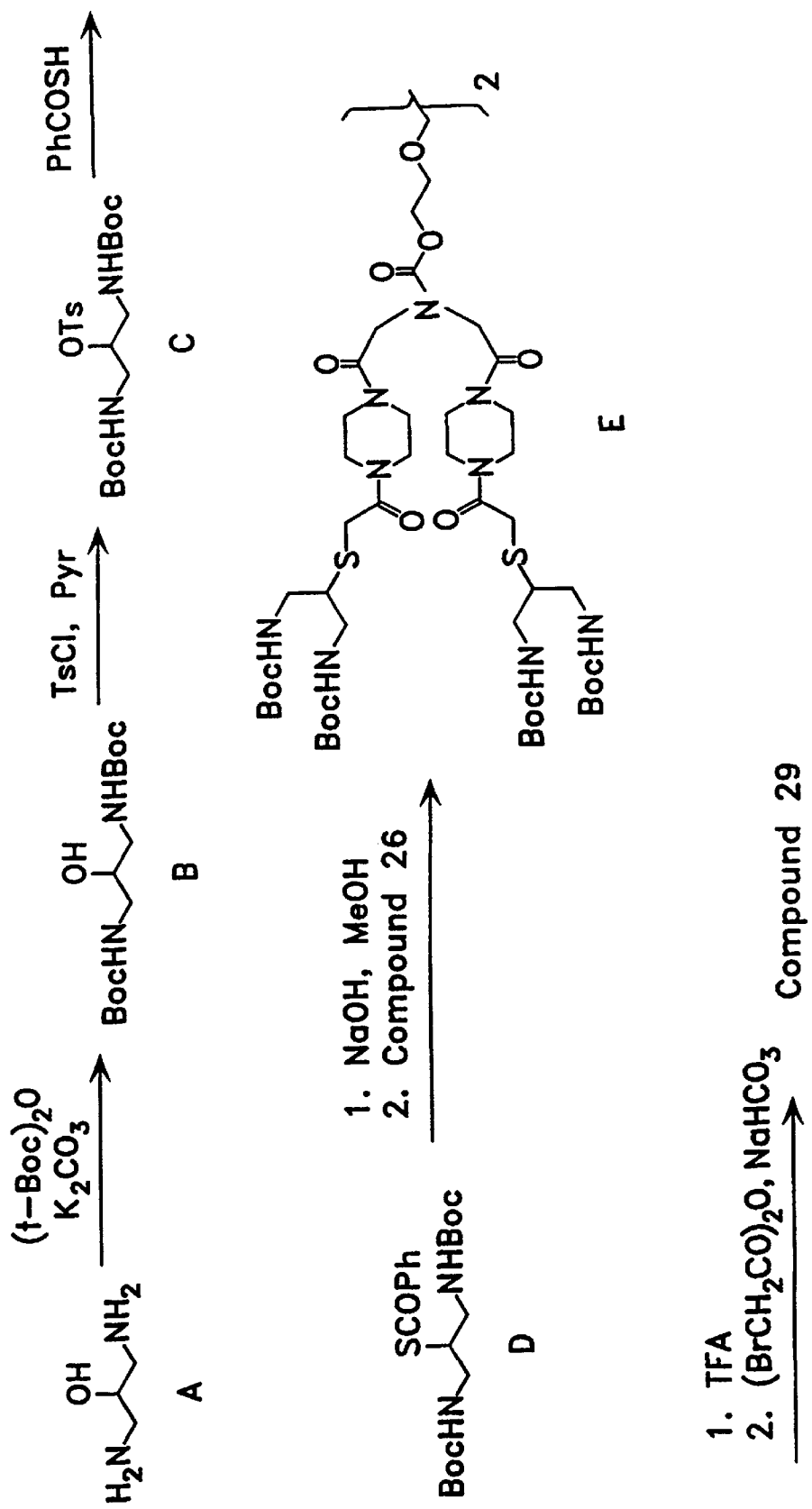
FIG. 24 depicts a strategy for the synthesis of octameric platform compound 29.

A strategy for synthesis of compound 29 is shown in FIG. 24.

Compound A: A solution of 1,3-diamino-2-hydroxypropane in aqueous dioxane was treated with di-t-butyldicarbonate and $Na_2CO_3$. The mixture was extracted with $CH_2Cl_2$, and the $CH_2Cl_2$ layer was dried and concentrated to give crude product which was purified by silica gel chromatography to give compound B.

Compound B was treated with p-toluensulfonyl chloride in pyridine. The mixture was acidified with aqueous HCl and extracted with $CH_2Cl_2$. The $CH_2Cl_2$ layer was dried and concentrated to give crude product which was purified by silica gel chromatography to give compound C.

A solution of compound C in a suitable solvent is treated with thiobenzoic acid and a suitable base. The mixture is extracted with $CH_2Cl_2$, and the $CH_2Cl_2$ layer is dried and concentrated to give crude product which is purified by silica gel chromatography to give compound D.

A solution of compound D in MeOH is treated with one equivalent of NaOH until the thiobenzoate ester is hydrolyzed as evidenced by TLC. To the resulting mixture is added 0.25 equivalents of compound 26. The mixture is stirred until complete as evidenced by TLC. The mixture is acidified with aqueous $H_2SO_4$ and extracted with $CH_2Cl_2$. The $CH_2Cl_2$ layer is dried and concentrated to give crude product which is purified by silica gel chromatography to give compound E.

Compound E is treated with trifluoroacetic acid to remove the BOC protecting groups. The mixture is concentrated, and the residue is dissolved in a solution of $NaHCO_3$ in 1/1 dioxane/water. To the resulting solution is added eight equivalents of bromoacetic anhydride. The mixture is stirred until complete as evidenced by TLC. The mixture is acidified with aqueous $H_2SO_4$ and extracted with $CH_2Cl_2$. The $CH_2Cl_2$ layer is dried and concentrated to give crude product which is purified by silica gel chromatography to give compound 29.

Synthesis of Compound 30

Figure 26A:
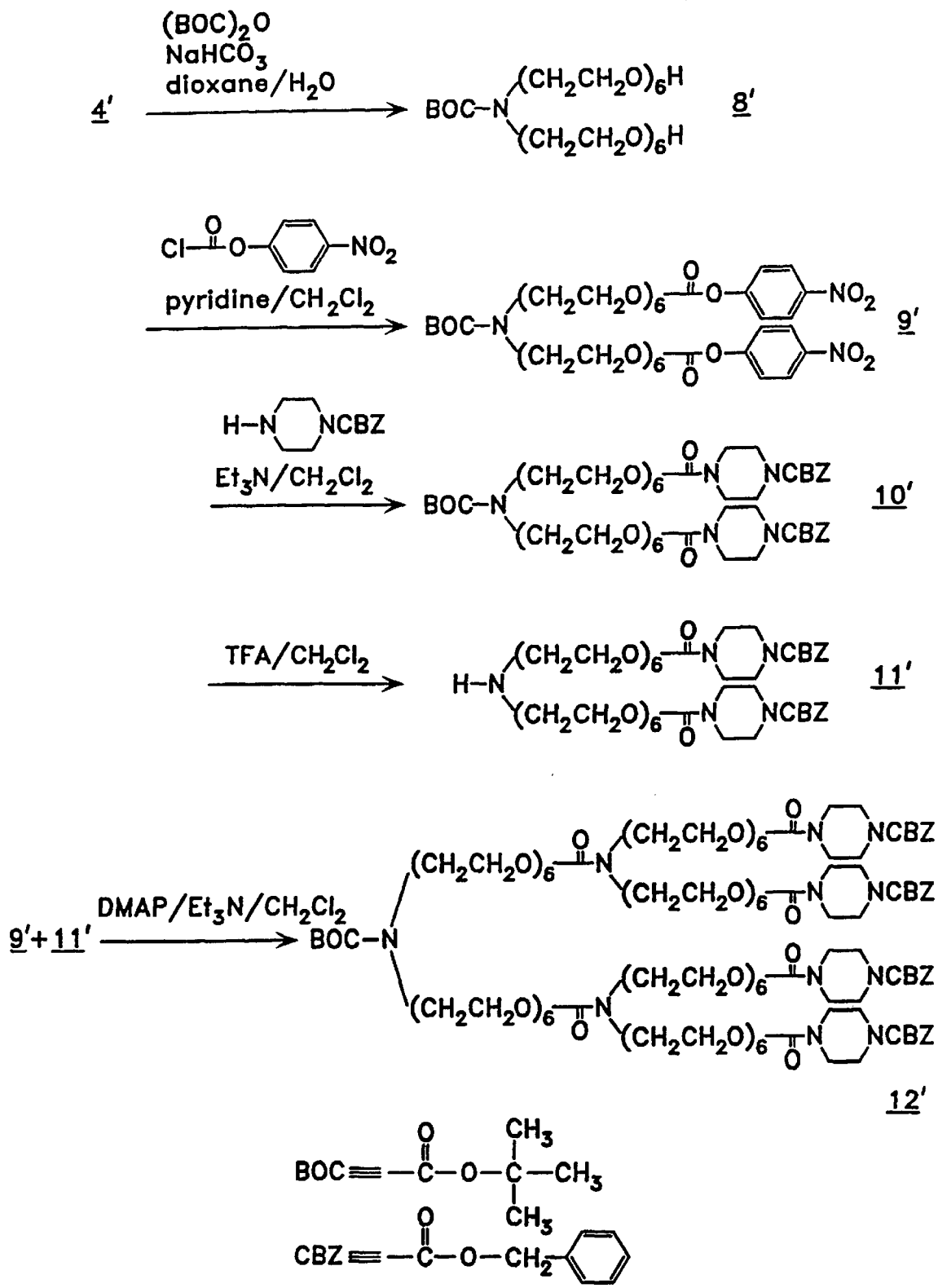
FIGS. 26A and 26B depict the synthesis of octameric platform compound 30.
Figure 26B:
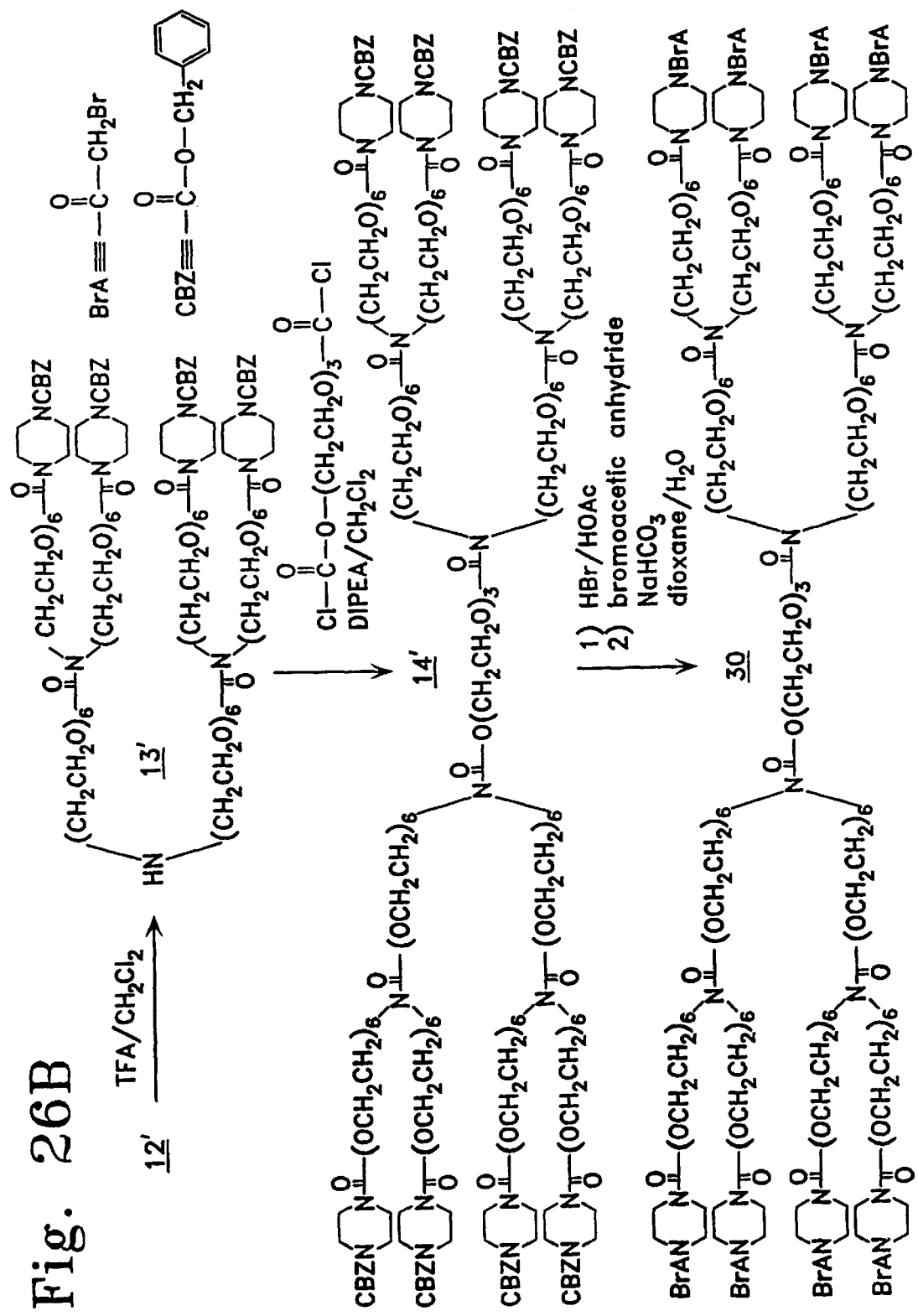

A chemical scheme for the preparation of an octamer of HEGA/TEG is shown in FIGS. 26A and 26B. Compound 30. The bis-hexaethyleneglycolamine (compound 4') was reacted with di-tert-butyldicarbonate to yield the N-BOC compound (compound 8'), which was then reacted with para-nitrophenylchloroformate to yield the para-nitrophenylcarbonate compound (compound 9'). The para-nitrophenylcarbonate (PNP) group was then converted to a carbamate group by reaction with mono-CBZ-protected piperazine, yielding compound 10'. The BOC group was removed using trifluoroacetic acid to yield compound 11'. Compounds 9' and 11' were then reacted together to form a "one-sided" dendritic compound (compound 12'). Again, the BOC group was removed using trifluoroacetic acid to yield compound 13'. Compound 13' was then reacted with triethyleneglycol bis chloroformate (from which the "core" is derived) to yield the "two-sided" dendritic compound (compound 14'). The terminal CBZ-protected amino groups were then converted to the hydrobromide salt of amino group, and further reacted with bromoacetic anhydride to yield reactive bromoacetyl groups at each of the termini in compound 30.

Synthesis of Compounds 31 and 32

Figure 25:
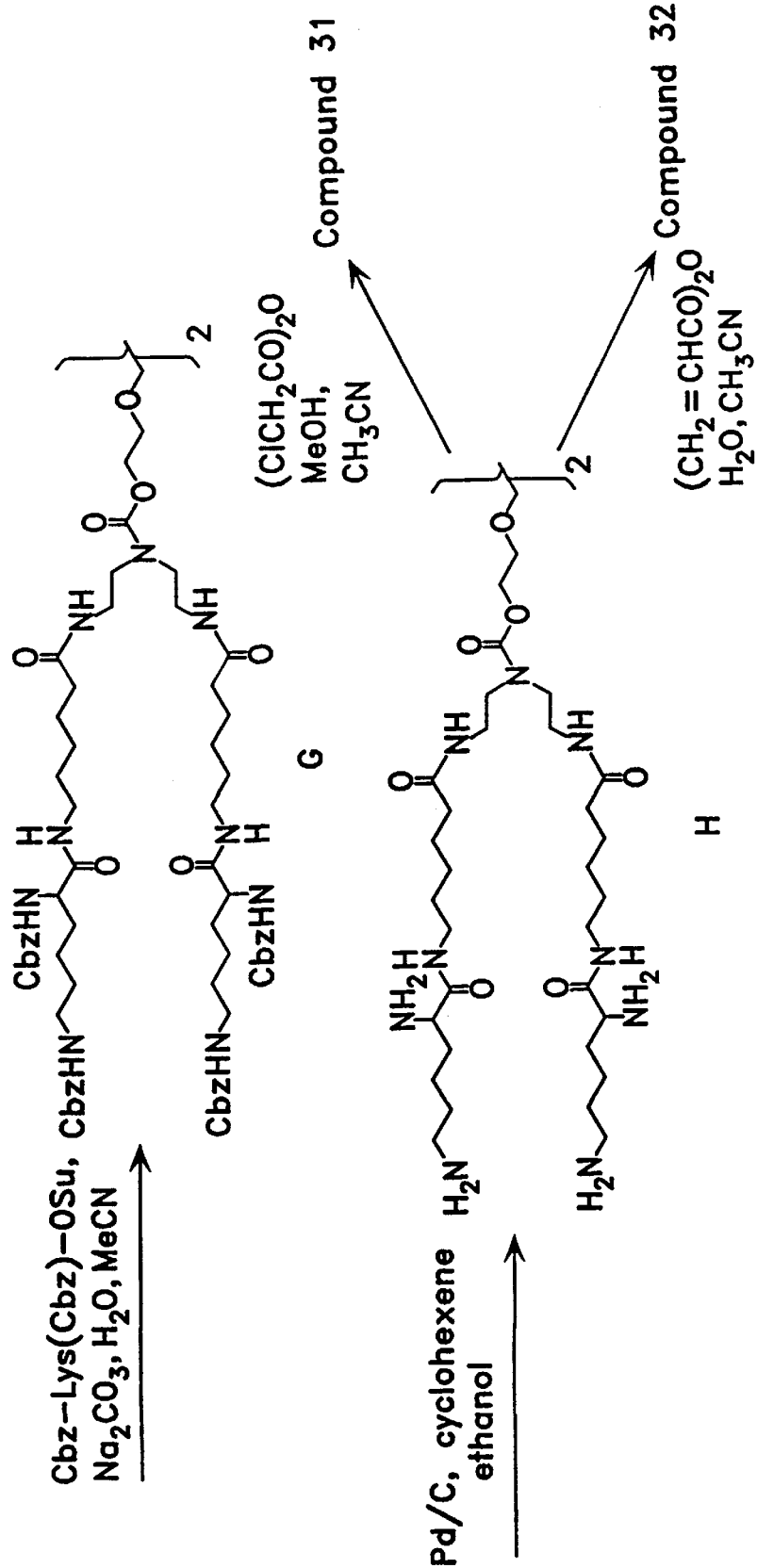
FIG. 25 depicts a strategy for the synthesis of octameric platforms compounds 31 and 32.

A strategy for synthesis of compound 31 and 32 is shown in FIG. 25.

Tetraamino platform, compound F, was reacted with the N-hydroxysuccinimidyl ester of $N_\alpha,N_\epsilon$-bis-CBZ-lysine in a solution of water/acetonitrile which contained $Na_2CO_3$. The acetonitrile was removed under vacuum, and the product precipitated. The precipitate was washed with water and recrystallized from acetonitrile to give G.

The CBZ groups were removed from compound G by catalytic hydrogenation using 10% Pd on carbon in ethanol. The mixture was filtered, and the filtrate was concentrated to give the octa-amine, compound H, as a brown oil.

Compound H was reacted with chloroaceticanhydride in methanol/acetonitrile at room temperature overnight. The crude product was purified by silica gel chromatography to give compound 31.

Compound 32

A solution of compound H is reacted with acryloyl chloride or acrylic anhydride in the presence of suitable base. The solvent is removed, and the crude product is purified by silica gel chromatography to give compound 32.

Example 3

Synthesis of αGal Conjugates

Compound 33

Synthesis of Monomeric αGal Conjugate

A mixture of αGal 20 (100 mg, 0.204 mmol), chloroacetamide (38 mg, 0.408 mmol), and tributylphosphine (10 μL) in 1 mL of $Na_2CO_3$ (10 mg/mL) solution in water/ACN (1:1) was stirred at room temperature overnight. After removing the organic solvent, the remaining aqueous solution was purified on reversed phase HPLC column eluted at 10 mL/min with a gradient of acetonitrile-water (5 to 15%) over 40 minutes to give 33 (96.3 mg, 86%) as a white solid: analytical RF-HPLC: $t_R$ 4.78 min with a gradient of 5 to 20% ACN in $H_2O$ at a flow rate of 1 mL/min. purity, 100%; MS (ESI): m/e (M+Na$^+$) Calcd. for $C_{20}H_{37}NO_{14}SNa$: 570.2, obsd: 570.3.

Compound 34

Synthesis of Dimeric αGal Conjugate

A mixture of αGal 20 (65 mg, 0.133 mmol) in 1 mL of $Na_2CO_3$ (20 mg/mL) aqueous solution was stirred at room temperature overnight. The solution was purified on reversed phase HPLC column eluted at 10 mL/min with a gradient of acetonitrile-water (10 to 25%) over 40 minutes to give 34 (31.3 mg, 48%) as a white solid: analytical RF-HPLC: $t_R$ 9.96 min with a gradient of 5 to 30% ACN in $H_2O$ at a flow rate of 1 mL/min. purity, 100%; MS (ESI): m/e (M+Na$^+$) Calcd. for $C_{36}H_{66}NO_{26}S_2Na$: 1001.3, obsd: 1001.3.

Compound 35

Synthesis of Dimeric αGal Conjugate

A mixture of αGal 19 (30 mg, 0.056 mmol), dimeric platform 23 (9.3 mg, 0.028 mmol), and tributylphosphine (0.030 mL) in 3 mL of $Na_2CO_3$ solution (20 mg/mL) and 2 mL of ACN was stirred under $N_2$ at room temperature overnight. After removing the organic solvent, the remaining aqueous solution was purified on reversed phase HPLC column eluted at 10 mL/min with a gradient of acetonitrile-water (5 to 15%) over 40 minutes to give 35 (10 mg, 31%)

as a white solid: analytical RF-HPLC: $t_R$ 8.69 min with a gradient of 5 to 30% ACN in $H_2O$ at a flow rate of 1 mL/min. purity, 97.9%; $^1H$ NMR ($D_2O$): δ 5.09 (d, J=3.5, 2 H), 4.39 (d, J=7.3, 2 H), 4.21 (t, J=6.5, 2 H), 4.10 (d, J=2.5, 2 H), 4.05 (m, 2 H), 3.96 (d, J=2.6, 2 H), 3.88 (d, J=2.5, 2 H), 3.85 (d, J=3.0, 2 H), 3.82–3.57 (m, 32 H), 3.27 (s, 4 H), 3.23 (s, 4 H), 2.79 (t, J=6.5, 4 H), 1.56 (br s, 4 H); $^{13}C$ NMR ($D_2O$): δ 173.1, 105.6, 103.4, 98.2, 96.0, 80.2, 78.3, 77.2, 75.3, 73.16, 71.8, 71.3, 70.9, 69.8, 69.4, 69.1, 65.4, 32.4, 40.5, 36.5, 34.6, 32.8; MS (ESI): m/e (M+Na$^+$) Calcd. for $C_{44}H_{80}N_2O_{28}S_2Na$: 1171.4, obsd: 1172.5.

Compound 36

Synthesis of Dimeric αGal Conjugate

This compound was prepared following the procedure described above for compound 35. Compound 19 (30 mg, 0.056 mmol) was conjugated with dimeric platform 24 (13.0 mg, 0.028 mmol) to give 36 as a white solid: analytical RF-HPLC: $t_R$ 11.3 min with a gradient of 5 to 30% ACN in $H_2O$ at a flow rate of 1 mL/min. purity, 97.4%; $^1H$ NMR ($D_2O$): δ 5.19 (d, J=3.5, 2 H), 4.53 (d, J=8.8, 2 H), 4.22 (t, J=3.9, 4 H), 4.13 (m, 2 H), 4.05–3.98 (m, 2 H), 3.91 (d, J=2.7, 2 H), 3.88–3.66 (m, 42 H), 3.63 (t, J=6.5, 4 H), 3.35 (t, J=7.2, 8 H), 2.84 (t, J=6.4, 4 H), 1.81 (m, 4 H); MS (ESI): m/e (M+Na$^+$) Calcd. for $C_{50}H_{92}N_2O_{31}S_2Na$: 1303.5, obsd: 1303.4.

Compound 37

Synthesis of Tetrameric αGal Conjugate

The tert-butylthio protecting group of αGal 7 (30 mg, 0.052 mmol) was removed by reducing with tributylphosphine (25 μL) in 5 mL of water at room temperature overnight. The reaction mixture was concentrated and dried under high vacuum overnight to remove any residual tert-butylthiol. The residue was dissolved in 5 mL of $Na_2CO_3$ (10 mg/mL) solution in water/ACN (1:1). Tetrameric platform 25 (5.0 mg, 0.0074 mmol) was added and the resulted solution was stirred at room temperature overnight. After removing the organic solvent, the remaining aqueous solution was purified on a reverse phase HPLC column eluted at 10 mL/min with a gradient of acetonitrile-water (20 to 25%) over 40 minutes to give 37 (9.6 mg, 56%) as a white solid after lyophilization: MS (ESI): m/e (M/2+Na$^+$) Calcd. for $C_{47}H_{79}O_{28}S_2Na$: 1178.4, obsd.: 1178.4.

Compound 38

Synthesis of Tetrameric αGal Conjugate

This compound was prepared following the procedure described above for compound 37. Compound 7 (22 mg, 0.038 mmol) was conjugated with platform 26 (7.0 mg, 0.0057 mmol). The product was purified on a reverse phase HPLC column with a gradient of acetonitrile-water (15 to 20%) over 40 minutes to yield 38 (13 mg, 80%) as a white solid: analytical RF-HPLC: $t_R$ 5.24 min with a gradient of 15 to 20% ACN in $H_2O$ at a flow rate of 1 mL/min, purity, 100%; MS (ESI): m/e (M/2+Na$^+$) Calcd. for $C_{56}H_{96}N_5O_{33}S_2Na$: 1454.6, obsd.: 1454.5.

Compound 39

Synthesis of Tetrameric αGal Conjugate

This compound was prepared following the procedure described above for compound 38. The conjugation of compound 7 (22 mg, 0.038 mmol) with platform 27 (6.0 mg, 0.0048 mmol) yielded 39 (12 mg, 93%) as a white solid: analytical RF-HPLC: $t_R$ 11.32 min with a gradient of 15 to 20% ACN in $H_2O$ at a flow rate of 1 mL/min, purity, 100%; MS (ESI): m/e (M/2+Na$^+$) Calcd. for $C_{53}H_{87}N_4O_{32}S_2Na$: 1379.1, obsd.: 1379.1.

Compound 40

Synthesis of Tetrameric αGal Conjugate

This conjugate is prepared by following the procedure described above for compound 38 using αGal 7 and platform 28.

Compound 41

Synthesis of Tetrameric αGal Conjugate 41

A mixture of p-aminophenyl 3-O-α-D-galactopyranosyl-α-D-galactopyranoside 22 (11 mg, 0.025 mmol), tetrameric platform 28, and $NaHCO_3$ (3 mg, 0.030 mmol) in 0.15 mL of $H_2O/CH_3CN$ (1:1) was slightly shaken for 1 h. After addition of 0.15 mL of $H_2O$, the reaction mixture was set at room temperature for 2 d and purified on reversed phase HPLC column eluted at 1 mL/min with a gradient of acetonitrile-water (0 to 30%) over 15 minutes to yield 41 (4.6 mg, 40%) as a white solid: MS (ESI): m/e (M/2+1) Calcd. for $C_{60}H_{95}N_7O_{29}$: 1377.6 obsd: 1377.9.

Compound 42

Synthesis of Tetrameric αGal Conjugate

A solution of the beta isomer of αGal 7, 2-[2-(2-thioethoxy)ethoxy]ethyl 3-O-(β-D-galactopyranosyl)-β-D-galactopyranoside (30 mg, 0.061 mmol), platform 25 (5 mg, 0.0074 mmol), and tributylphosphine (0.10 mL) in 5 mL of $Na_2CO_3$ (10 mg/mL) solution in water/ACN (1:1) was stirred at room temperature overnight. After removing the organic solvent, the remaining aqueous solution was purified on a reverse phase HPLC column eluted at 10 mL/min with a gradient of acetonitrile-water (20 to 25%) over 40 minutes to give 42 (2.4 mg, 14%) as a white solid: MS (ESI): m/e (M/2+Na$^+$) Calcd. for $C_{47}H_{79}O_{28}S_2Na$: 1178.4, obsd.: 1179.0.

Compound 43

Synthesis of Tetrameric αGal Conjugate

This conjugate was prepared by following the procedure described above for compound 38. The conjugation of compound 8 (25 mg, 0.043 mmol) with platform 27 (6.0 mg, 0.0048 mmol) yielded 43 (8.8 mg, 68%) as a white solid: analytical RF-HPLC: $t_R$ 6.84 min with a gradient of 15 to 20% ACN in $H_2O$ at a flow rate of 1 mL/min, purity, 100%; MS (ESI): m/e (M/2+Na$^+$) Calcd. for $C_{53}H_{87}N_4O_{32}S_2Na$: 1379.4, obsd.: 1379.1.

Compound 44

Synthesis of Octameric αGal Conjugate

A solution of αGal 19 (23 mg, 0.429 mmol) and platform 29 (10 mg, 0.0043 mmol) in 2 mL of $Na_2CO_3$ (10 mg/mL) solution in water/ACN (1:1) was stirred under $N_2$ at room temperature overnight. The reaction mixture was concentrated and purified on a reverse phase HPLC column eluted at 10 mL/min with a gradient of acetonitrile-water (10 to 30%) over 40 minutes to give 44 (8.5 mg, 37%) as a white solid.

Compound 45

Synthesis of Octameric αGal Conjugate

This compound was prepared following the procedure described above for compound 44. Compound 19 (50 mg, 0.094 mmol) was conjugated with platform 30 (10 mg, 0.0018 mmol). The product was purified on a reverse phase HPLC column with a gradient of acetonitrile-water (10 to 50%) over 40 minutes to yield 45 (10.8 mg, 67%) as a white solid: analytical RF-HPLC: $t_R$ 11.16 min with a gradient of 5 to 70% ACN in $H_2O$ at a flow rate of 1 mL/min, purity, 100%.

Compound 46

Synthesis of Octameric αGal Conjugate

This compound was prepared following the procedure described above for compound 44. Compound 19 (691 mg, 1.41 mmol) was conjugated with platform 31 (280 mg, 0.141 mmol). The product was purified on a reverse phase HPLC column with acetonitrile-water (19.5%) over 40 minutes to yield 46 (604 mg, 76%) as a white solid: analytical RF-HPLC: $t_R$ 9.16 min with a gradient of 15–25% ACN in $H_2O$ at a flow rate of 1 mL/min, purity, 100%; $^1H$ NMR ($D_2O$): δ 5.13 (d, J=3.8, 8 H), 4.47 (d, J=7.8, 8 H), 4.12–4.16 (m, 24 H), 4.12–4.05 (m, 8 H), 4.00 (d, J=0.8, 8 H), 3.99–3.92 (m, 8 H), 3.86–3.64 (m, 144 H), 3.39–3.34 (m, 24 H), 3.28 (S, 8 H), 3.22–3.11 (m, 16 H), 2.79 (dd, J=6.1, 10.6, 16 H), 2.20 (t, J=7.1, 8 H), 1.82–1.68 (m, 8 H), 1.59–1.20 (m, 40 H); $^{13}C$ NMR ($D_2O$): δ 178.5, 178.4, 175.1, 174.2, 174.0, 159.3, 104.4, 97.0, 78.9, 76.6, 72.5, 71.4, 71.3, 71.1, 71.0, 70.9, 70.8, 70.3, 69.9, 66.5, 62.6, 55.9, 48.5, 48.1, 41.1, 40.8, 39.1, 38.9, 37.4, 37.0, 36.5, 33.0, 32.9, 32.6, 29.8, 29.6, 27.4, 26.7, 24.3; MS (ESI): m/e (M/3+Na$^+$) Calcd. for ($C_{224}H_{400}N_{18}O_{126}S_8$)/3+Na: 1895.7, obsd.: 1895.3.

Compound 47

Synthesis of Octameric αGal Conjugate

This compound was prepared following the procedure described above for compound 44. Compound 19 (29 mg, 0.055 mmol) was conjugated with platform 32 (10 mg, 0.0055 mmol). The product was purified on reverse phase HPLC column with a gradient of acetonitrile-water (15 to 20%) over 40 minutes to yield 47 (20 mg, 65%) as a white solid: analytical RF-HPLC: $t_R$ 11.35 min with a gradient of 15 to 25% ACN in $H_2O$ at a flow rate of 1 mL/min. purity, 82%; MS (ESI): m/e (M/3+Na$^+$) Calcd. for ($C_{232}H_{416}N_{18}O_{126}S_8$)/3+Na: 1933.1, obsd.: 1932.1.

Example 4

In Vitro Characterization of αGal Conjugates

Materials and Methods

Figure 16:
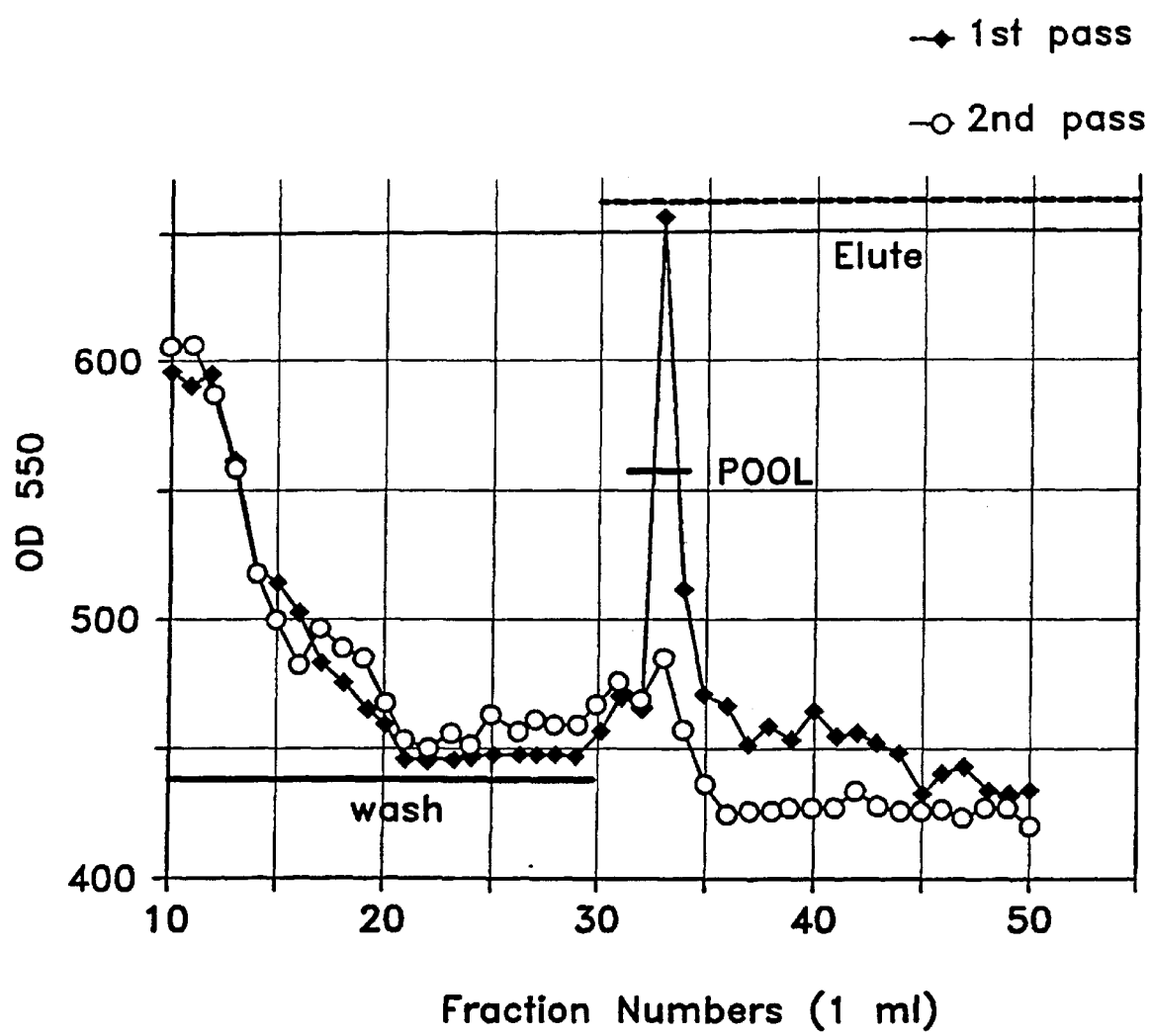
FIG. 16 is a graph depicting the elution profile of anti-αGal from an αGal affinity column (OD550 versus fraction number).
Figure 17A:
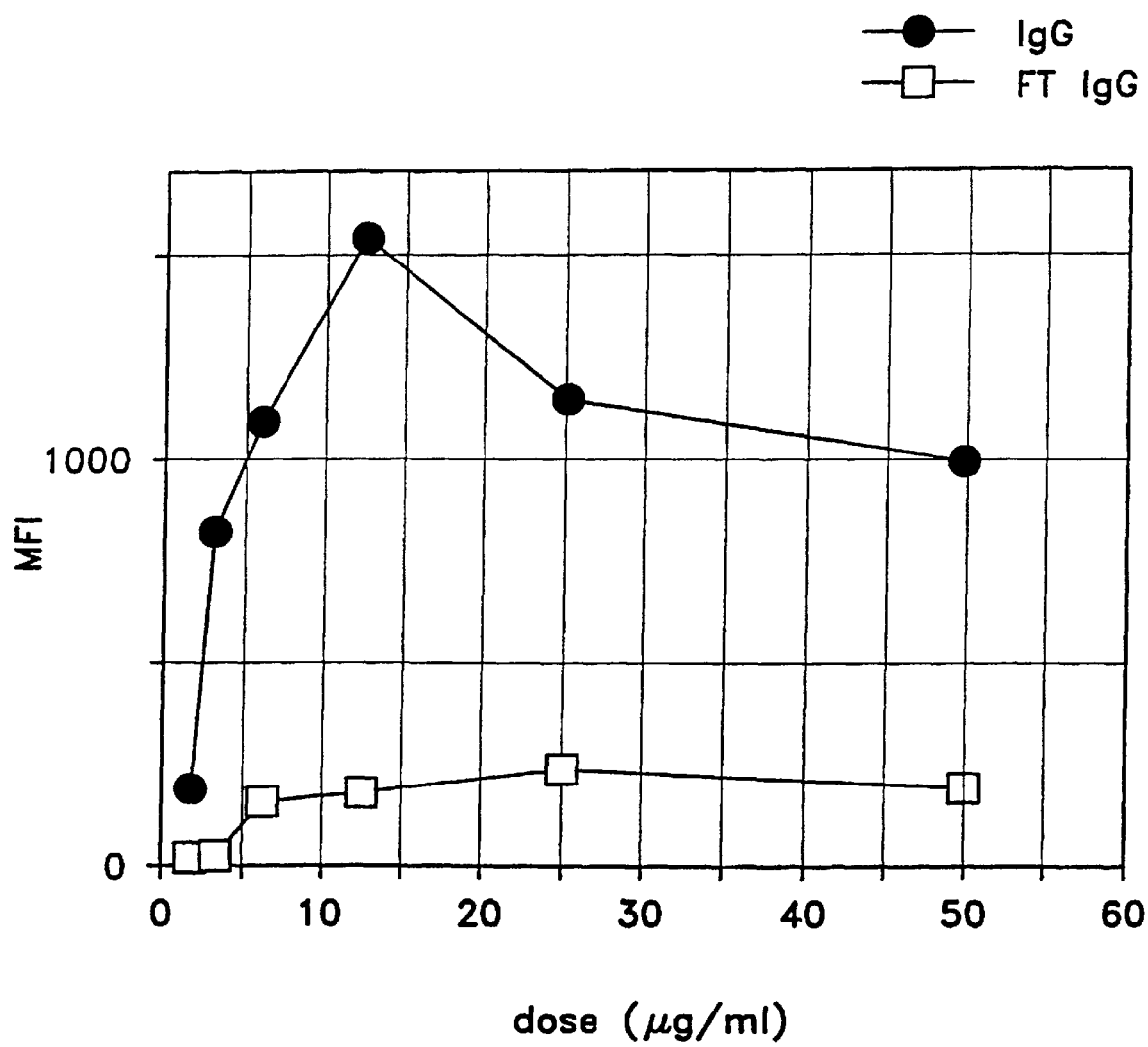
FIGS. 17A and 17B are graphs depicting affinity purified IgG (17A) and IgM (17B) anti-αGal binding to PK15 cells. Flow cytometric analysis results are shown as mean fluorescence intensity (MFI) versus dose, in μg/ml, of affinity-purified IgG or IgM (solid circles), or column flow-through IgG or IgM (open squares).
Figure 17B:
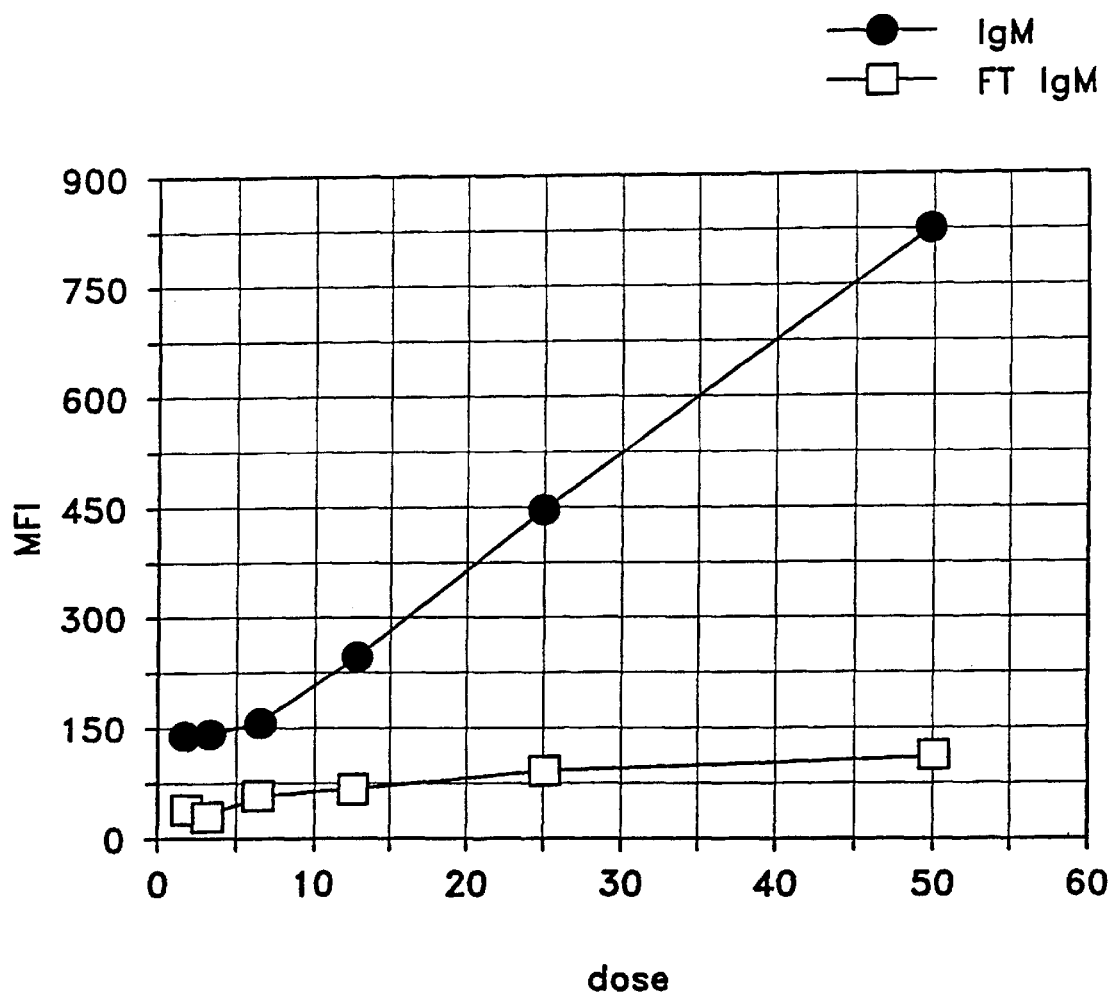

Antibodies. Blood was drawn from healthy normal volunteers. Plasma was separated by centrifugation and allowed to clot. Fibrin was removed and plasma was used immediately or stored in aliquots at −70° C. Rhesus monkey serum (California Regional Primate Research Center, Davis, Calif.) was obtained from blood drawn into vacutainer tubes and allowed to clot. After serum was separated by centrifugation, it was pooled, aliquoted and stored at −20° C. or −70° C. In some experiments, sera was heat-inactivated at 56° C. for 30 minutes to destroy complement hemolytic activity. Antibodies to the αGal epitope were affinity purified on an αGal-Sepharose column, which was prepared by coupling αGal-SH to maleimide-Sepharose (Pierce) through Michael addition chemistry at 10 mg/mL resin. Up to 20 mL pooled NHS or normal monkey serum (NMS) was applied to a 2 mL volume of packed αGal-Sepharose. After the flow through was collected, the column was washed with 10–20 column volumes or until $A_{280}$ reached baseline values and eluted with 0.1 M triethanolamine, pH 11.5 into tubes containing 1M Tris, pH 8.0. The column was immediately washed with 10–20 volumes of phosphate-buffered saline (PBS). Fractions were assessed for protein concentration by Bradford assay. Peak fractions were pooled and dialyzed against PBS. Affinity-purified anti-αGal Ig was negatively selected for IgG by purification over an MBP column (Pierce, Rockford, Ill.) which removed IgM anti-αGal antibodies. IgM anti-αGal was negatively selected by purification over a protein G-Sepharose column (Boehringer Mannheim, Indianapolis, Ind.) which removed IgG anti-αGal antibodies. An elution profile of anti-αGal Ig from an αGal affinity column is shown in FIG. 16.

SDS-PAGE and Immunoblot Analysis. Antibody-containing fractions and pools were resolved by 4–12% SDS-PAGE (Novex, San Diego, Calif.). Proteins were electrophoretically transferred to PROTRAN™ pure nitrocellulose membranes (Schleicher and Schuell, Keene, N.H.) using XCELL II™ Blot Module blot system (Novex). Membranes were blocked with 2% non-fat dry milk (NFDM) in PBS and probed with anti-human IgG or IgM coupled to alkaline phosphatase (Jackson ImmunoResearch, West Grove, Pa.) or anti-monkey IgG or IgM coupled to alkaline phosphatase (Advanced Chem Tech, Louisville, Ky.). Second step antibody was developed with Western Blue Stabilized Substrate for alkaline phosphatase (Promega Corporation, Madison, Wis.).

ELISA for anti-αGal antibodies. αGal-SH was coupled to maleimide-BSA (bovine serum albumin) (Pierce) at a 2:1 ratio (w/w) according to manufacturer's protocol. The ratio of αGal molecules coupled per BSA molecule was 10–12:1 or 25:1. Alternatively, αGal-BSA or αGal-HSA (human serum albumin) was purchased with C3 or C14 linker groups (Dextra, Redding, England). αGal-BSA (100 μl at 5 μg/mL in PBS) was adsorbed onto 96 well plates for 18 hours at 4° C. Plates were blocked with 2% NFDM in PBS at 4° C. for at least 48 hours prior to use. Plates were stable for at least 3 months. New lots of plates were compared with binding efficacy of the original lot using pooled standard serum. Pooled standard sera, individual sera or affinity purified anti-αGal Ig were titered. Serum (100 μL neat—1/256 diluted in HBSA) or affinity-purified anti-αGal IgG (100 μL of serial two-fold dilutions from 2 mg/mL–1 μg/mL in Hank's balanced salt solution without $Ca^{+2}$ or $Mg^{+2}$ (HBSA)) were incubated in αGal-BSA coated wells for 60 minutes at 20° C. After washing, anti-αGal Ig was developed with predetermined saturating concentrations (100 μL, usually 1:1000 dilution) of anti-monkey or anti-human IgG or IgM coupled to alkaline phosphatase for 60 minutes at 20° C. After washing the wells 5 times with wash buffer (1% Tween 20 in PBS), plates were developed with 100 μL PPMP (phenolphthalein monophosphate) (Sigma) for 5–20 minutes at 20° C. Reactions were stopped by addition of 100 μL 0.2M $Na_2HPO_4$ and plates read at $A_{550}$ (PowerWave 340 Microplate Spectrophotometer, Bio-Tek, Winooski, Vt.).

αgal Conjugates. αGal (galactose (α1, 3, galactose) epitopes were synthesized at a multigram scale as described in Example 1 and were coupled to a well-defined organic platform as described in Example 3.

Competition ELISA. Serum or affinity purified anti-α(gal Ig preparations were titered by ELISA and the 50% binding concentration was determined. For serum, the 50% binding point was reached at a serum dilution of ~1:5 while for affinity-purified Ig, the 50% dilution binding concentration was 12.5 μg/mL. Serum or Ig (50 μL) was incubated with an equal volume of HBSA containing inhibitor which was serially diluted in a two-fold manner from 4 mg/mL to 10 μg/mL or buffer alone for 60 minutes at 20° C. Anti-αGal Ig or serum±inhibitor was then added to αGal-BSA-coated plates and Ig binding was assessed as described. Percent inhibition of anti-digal binding was calculated as follows:

[($OD_{550}$ Ig source+INH)−$OD_{550}$ blank/($OD_{550}$ Ig source−INH)−$OD_{550}$ blank]×100. (INH=inhibitor)

ELISpot assay. Spleens from normal rhesus monkeys were minced and prepared as single cell suspension using deburred frosted glass slides. Contaminating erythrocytes were hypotonically lysed and mononuclear cells (MNC) isolated by Ficoll-hypaque density gradient centrifugation. MNC (100 μL) were added in serial two-fold dilutions from $10^4$/cells/mL to $5\times10^2$ cells/mL in quadruplicate to ELISA plates bearing αGal-BSA or anti-monkey IgG or IgM. Plates were incubated overnight at 37° C. in a humidified atmosphere with 5% $CO_2$ and then washed. The footprint of secreted anti-αGal Ig bound to αGal-BSA was developed by incubation with goat anti-monkey IgG or IgM coupled to biotin (Advanced ChemTech) for 60 minutes at 37° C. followed by the addition of ExtrAvidin-alkaline phosphatase (Sigma). Alkaline phosphatase substrate B (100 μL at 1:100 dilution, Bio-Rad, Hercules, Calif.) was added and incubation continued overnight at 20° C. Total Ig-producing cells were similarly determined. The footprints were quantified using a Microtek ScanMaker III flat-bed scanner and personal computer utilizing the Image-Pro imaging software (Media Cybernetics, Univ. Rochester Medical School, Rochester, N.Y.). The ratio of anti-αGal IgG- or IgM-producing cells/total IgG- or IgM-producing cells were calculated.

Cytoxicity assays. The porcine kidney epithelial cell line PK-15 and porcine aortic endothelial cells (PAEC) (ATCC, 10801 University Blvd., Manassas, Va. 20110-2209) were cultured as directed. For the assay, cells were removed with trypsin—EDTA and replated subconfluently in 96 well plates or on coverslips in 24-well plates. While still subconfluent (within 2 days of replating), cells were used in cytotoxicity assays. Neat, complement-sufficient serum was incubated with inhibitor as described for 60 minutes at 4° C. Serum was then added to wells containing subconfluent cells from which medium had been aspirated immediately prior to serum addition. Wells were incubated with serum±inhibitor for 60–90 minutes at 37° C. Wells were rinsed and cell death was visualized using a Live/Dead kit (Molecular Probes, Eugene, Oreg.) and quantified microscopically in 10 high powered fields or by counting 250 cells. For some experiments, cells were non-enzymatically removed from flasks with cell dissociation solution (Sigma) and single cell suspensions prepared. Assays were performed as for adherent cells except that cytoxicity was quantified by flow cytometry on a Becton-Dickinson FACScalibur.

Results

Antigenic Activity of αGal Epitope

The synthetically prepared αGal epitope (FIG. 2) was antigenically active, as demonstrated by its ability (when coupled to Sepharose) to remove >95% of anti-αGal Ig from normal rhesus monkey or human serum as measured by FACS.

Activity of tetrameric conjugates. We tested the αGal tetrameric platform constructs which included the PITG platform (compound (cpd) 38) and BMTG (cpd 37) platforms as described in Example 2 and found them to be equivalent in their ability to inhibit Ab from binding to the αGal epitope in the ELISA. Cpd 38 (LJP712) bound anti-αGal Ig and inhibited the binding of IgG anti-αgal to the αGal-expressing porcine kidney epithelial cell line PK-15 and to BSA-αGal adsorbed onto ELISA wells at ~1 mM. The binding of affinity purified IgM anti-αGal was inhibited 1000-fold less well by cpd 38 than was the IgG anti-αGal.

Figure 18:
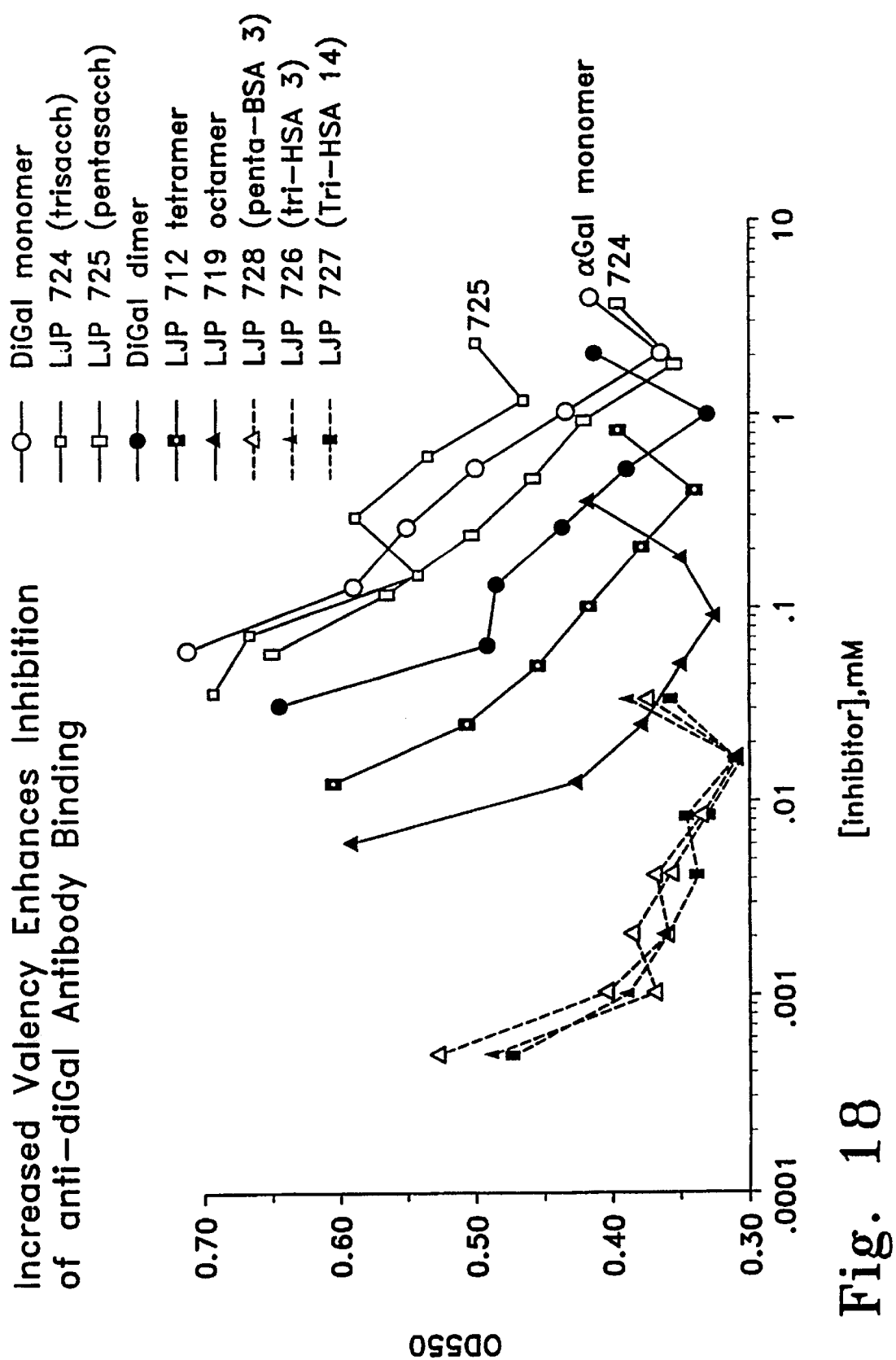
FIG. 18 is a graph depicting the effect of αGal valency of toleragens on inhibition of anti-αGal binding, measured by ELISA as described in Example 4. Symbols for inhibitors are as follows: open circles=αGal monomer; open squares, dashed lines=LJP 724 (trisaccharide monomer); open squares, dashed lines=LJP 725 (pentasaccharide monomer); solid circles, solid lines=αGal dimer; solid squares, solid lines=LJP 712 tetramer; solid triangles, solid lines=LJP 719 octamer; open triangles, dashed lines=LJP 728 (11-mer pentasaccharide-BSA); solid triangles, dashed lines=LJP 726 (11-mer trisaccharide [3-carbon linker]-HSA); solid squares, dashed lines=LJP 727 (11-mer trisaccharide [14-carbon linker]-HSA).

Activity of octameric conjugates. Octameric conjugates (as described in Example 2) were tested. Octameric conjugate cpd 44 (also referred to as LJP 719) was tested in vitro for its ability to inhibit in serum the anti-αGal IgM binding to BSA-αGal. ELISA analysis showed that the αGal epitope when presented on a platform as an octamer inhibited both IgG and IgM anti-αGal in serum from binding to BSA-αGal or to the αGal-expressing porcine kidney epithelial cell line PK-15 and was 5–10 fold more efficient at inhibiting the IgM anti-αGal binding to the αGal epitope, as shown in FIG. 18. This supported our hypothesis that valency of the toleragen was very important in binding the lower affinity IgM molecules.

Example 5

In Vivo Evaluation of Conjugates

The in vivo efficacy of the toleragens was tested in a dose-escalation study in rhesus monkeys which were treated IV with tetrameric or octameric toleragen or buffer.

Six male rhesus monkeys (3.5–4 kg) were housed at the California Regional Primate Research Center (CRPRC), Davis, Calif. All experimental protocols met CRPRC IACUC (Institutional Animal Care and Use Committee) standards. Monkeys were bled for baseline clinical values and anti-αGal antibody levels. Monkeys were bled for baseline clinical values. Four monkeys were treated IV daily with 2–20 mg/kg of tetravalent platform LJP 712 (cpd 38). Two monkeys received PBS alone intravenously (IV) as a control. Monkeys were bled weekly (5 mL) immediately prior to the IV injection in those animals treated for 60 days with LJP 712 at 2 mg/kg. When monkeys received 10 mg/kg or 20 mg/kg of tetrameric LJP 712 or 20 mg/kg octameric LJP 920 (cpd 46), treatment was for 5–7 days and animals were bled every 2–3 days for 3 mL. Serum samples were analyzed by ELISA for anti-αGal IgG and IgM. In one experiment, two monkeys were treated IV daily for 10 days with 20 mg/kg octameric platform LJP 719. In another experiment, monkeys were treated daily IV with octameric LJP 920 at 20 mg/kg.

Figure 20:
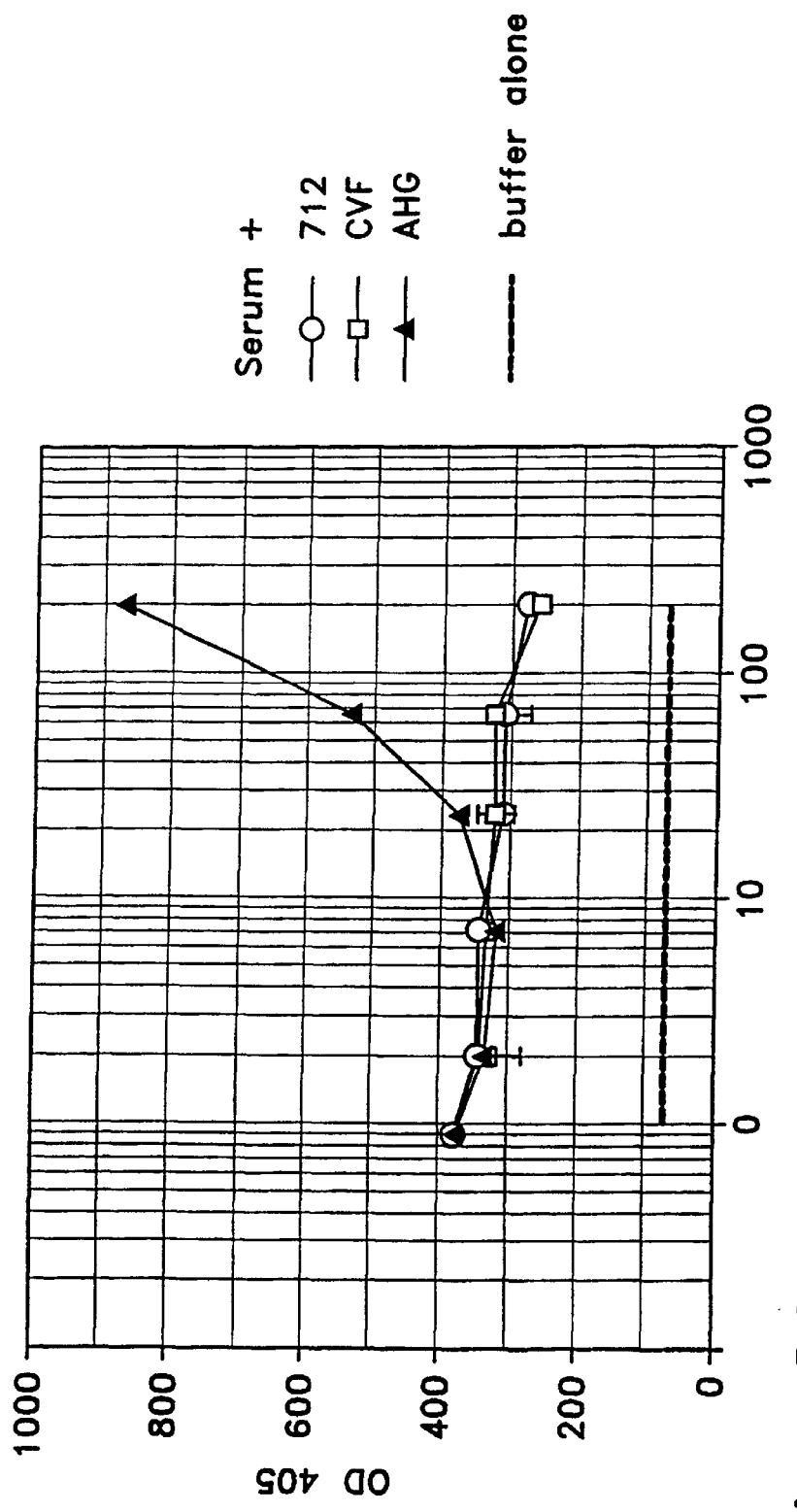
FIG. 20 is a graph depicting activation of the classical complement pathway by various substances, as described in Example 5. Symbols are as follows: open circles, LJP 712; open squares, cobra venom factor (CVF); solid triangles, aggregated human gamma globulin (AHG). The dashed line represents results obtained with buffer alone.
Figure 21:
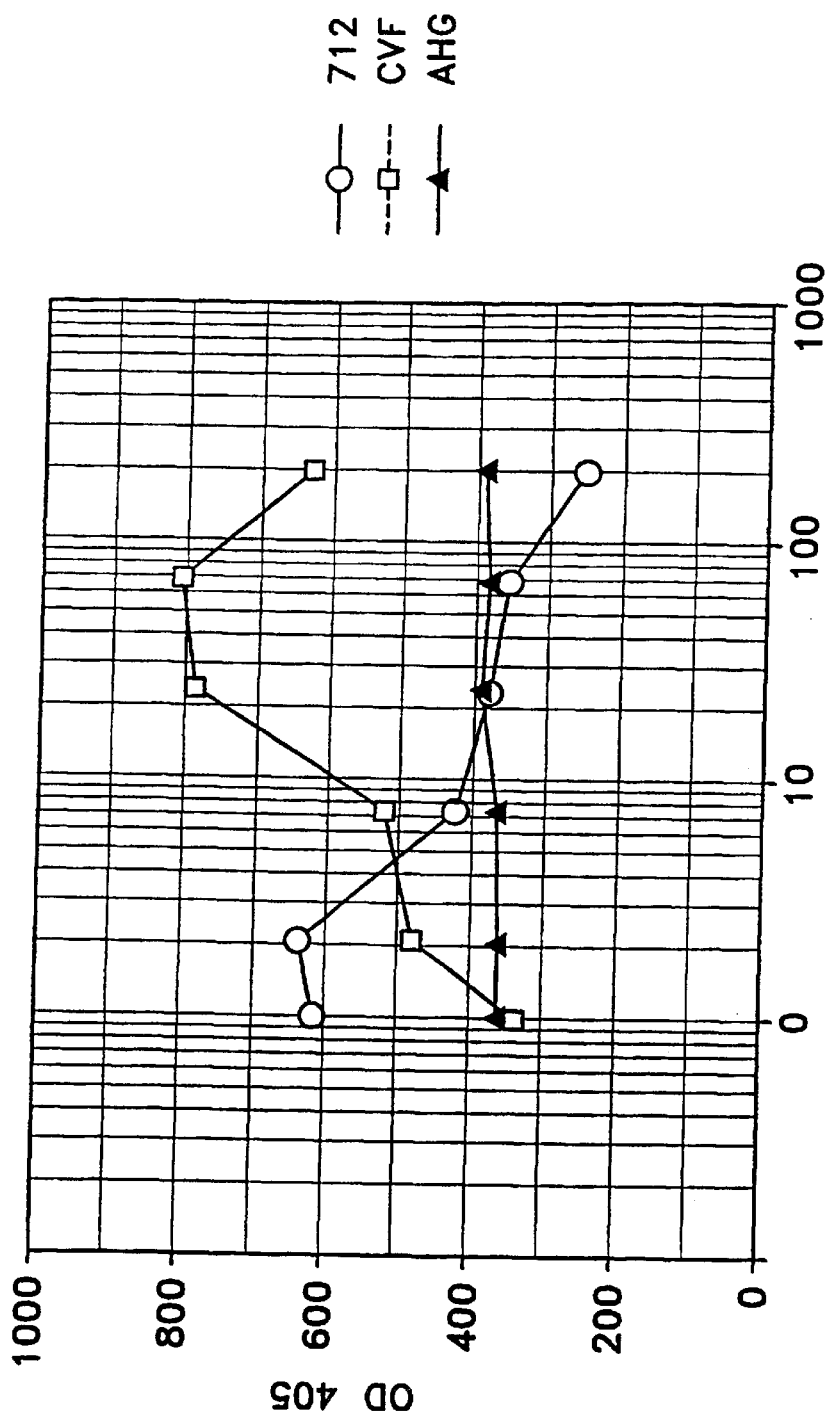
FIG. 21 is a graph depicting activation of the alternative complement pathway by various substances, as described in Example 5. Symbols are as follows: open circles, LJP 712; open squares, CVF; solid triangles, AHG.

Tetrameric conjugates. To test the in vivo efficacy of LJP 712, the tetravalent toleragen at doses high enough to create a molar excess of toleragen to anti-αGal antibody in the plasma based on 1% of circulating antibody being specific for αGal was used to treat monkeys. Monkeys were treated IV daily with 2 mg/kg of LJP 712 (n=4) or buffer (PBS) (n=2) for 60 days as described above. Blood was drawn weekly and serum tested by ELISA for IgG and IgM anti-αGal. LJP 712 was well-tolerated and did not activate either the classical or alternative complement pathways in vitro, as shown in FIGS. 20 and 21, respectively. There was no statistically significant diminution of anti-αGal Ig responses.

Figure 19:
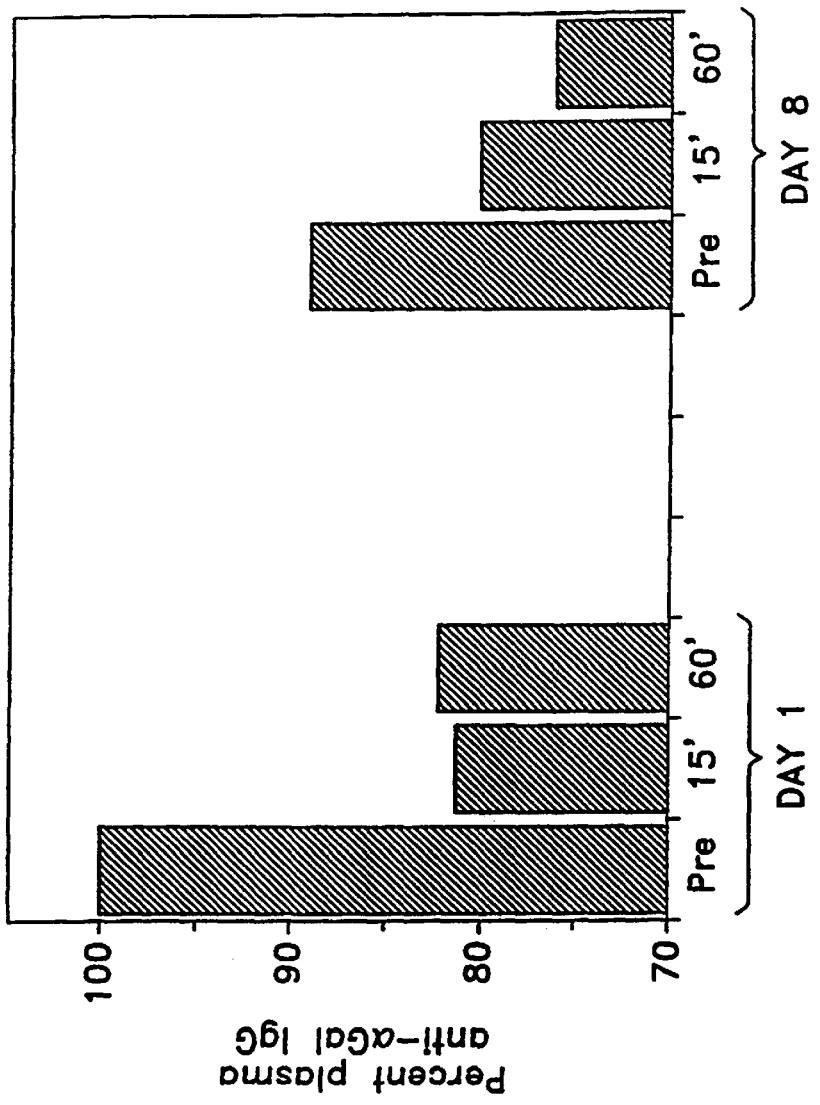
FIG. 19 is a bar graph of the percent plasma anti-αGal IgG following treatment of primates with LJP 712, as described in Example 5.

We next sought to determine whether higher doses of LJP 712 were able to effect clearance of anti-αGal Ab from the circulation using shorter term IV dosing modalities. When the dose was increased to 10 mg/kg LJP 712, little diminution of either IgG or IgM anti-αGal was observed. By contrast, daily IV treatment with 20 mg/kg LJP 712 resulted in the diminution of the anti-αGal IgG response by up to 24% (p<0.05) by day 8 of treatment and anti-αGal IgM levels by up to 12% (p=NS), as shown in FIG. 19.

Octameric Conjugates

Figure 22A:
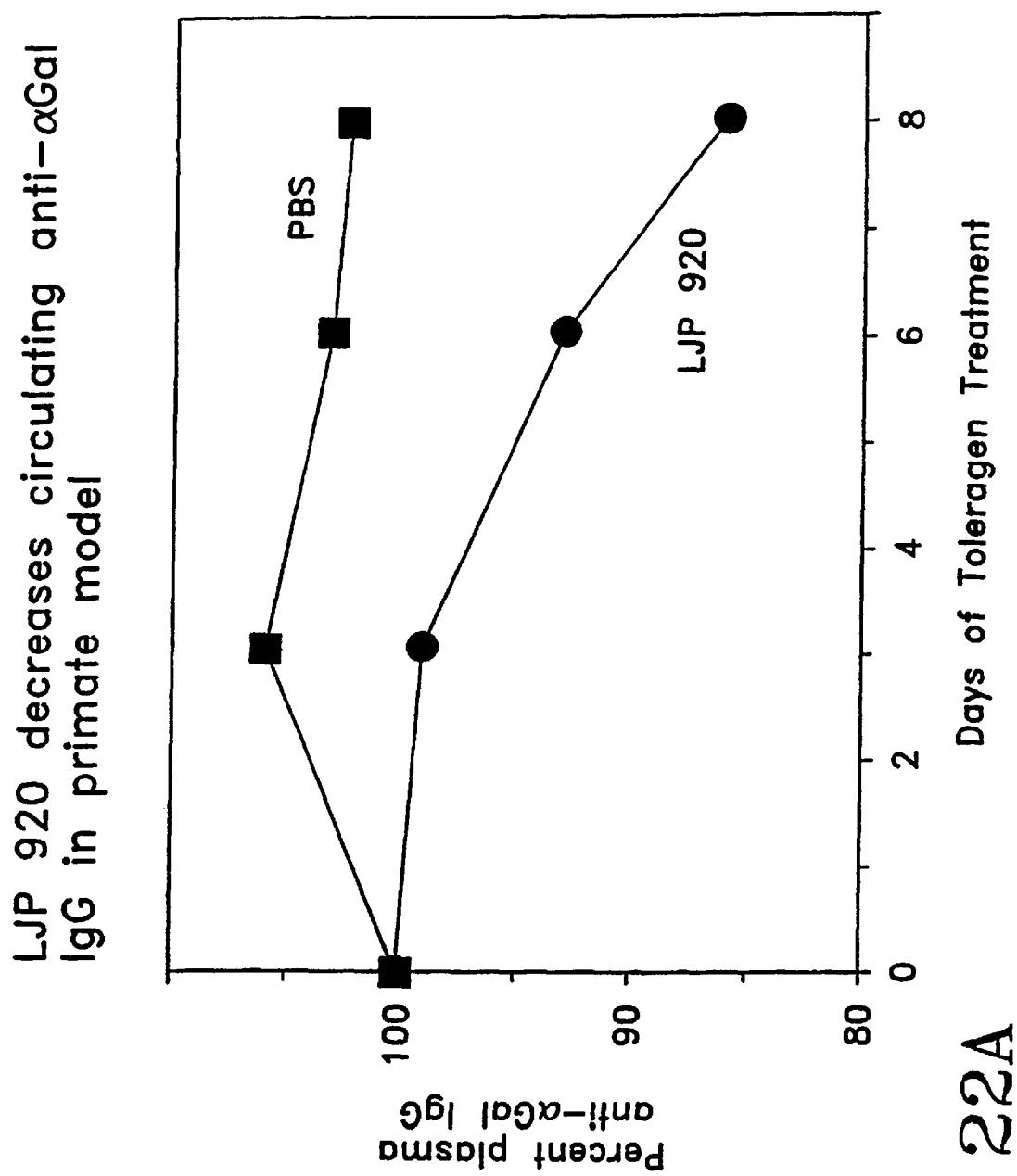
FIGS. 22A and 22B are graphs depicting the decrease in plasma anti-αGal IgG (22A) and IgM (22B) following treatment with octameric LJP 920 (cpd 46) (circles), compared with PBS (squares), as described in Example 5.
Figure 22B:
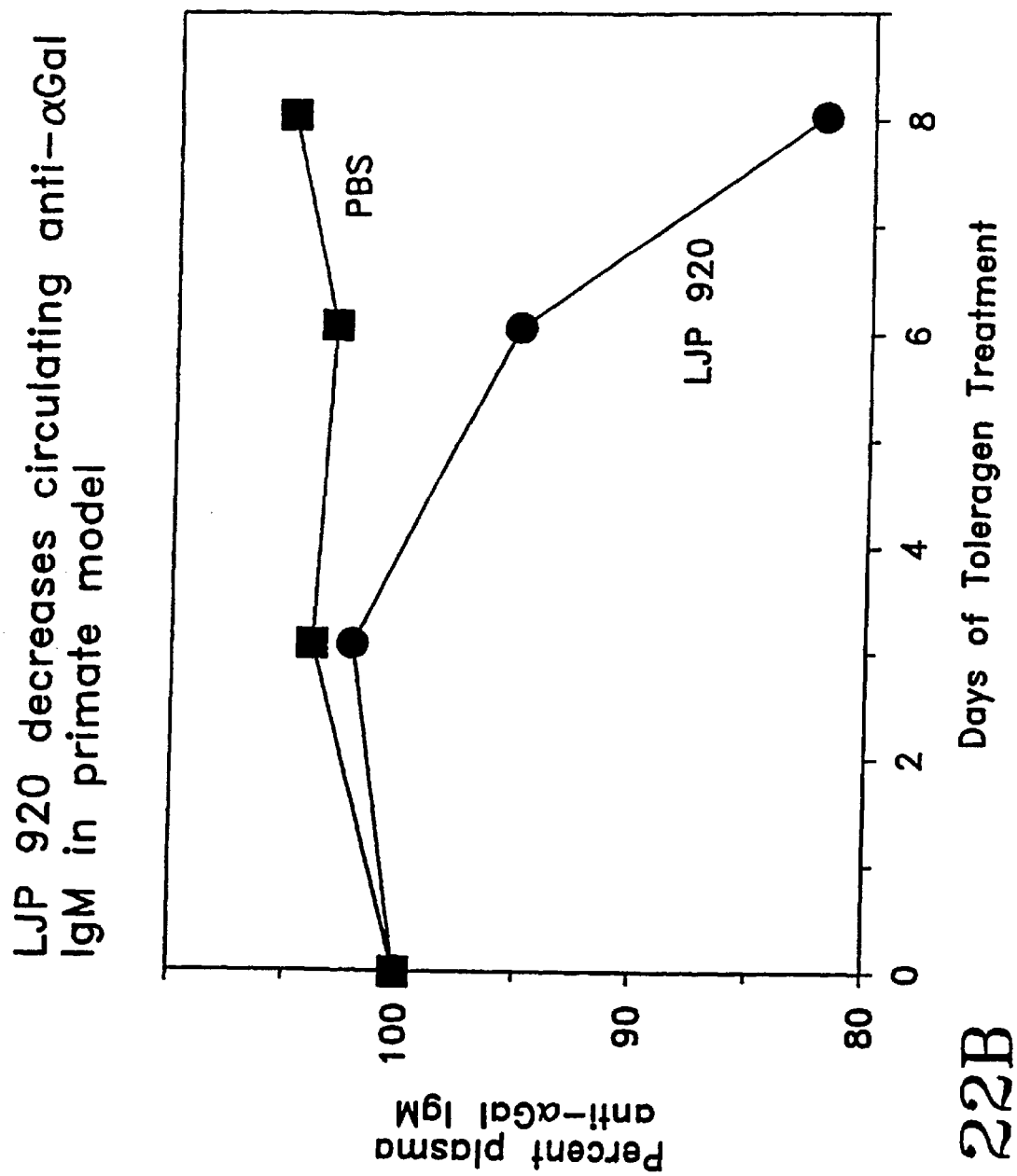
Figure 23:
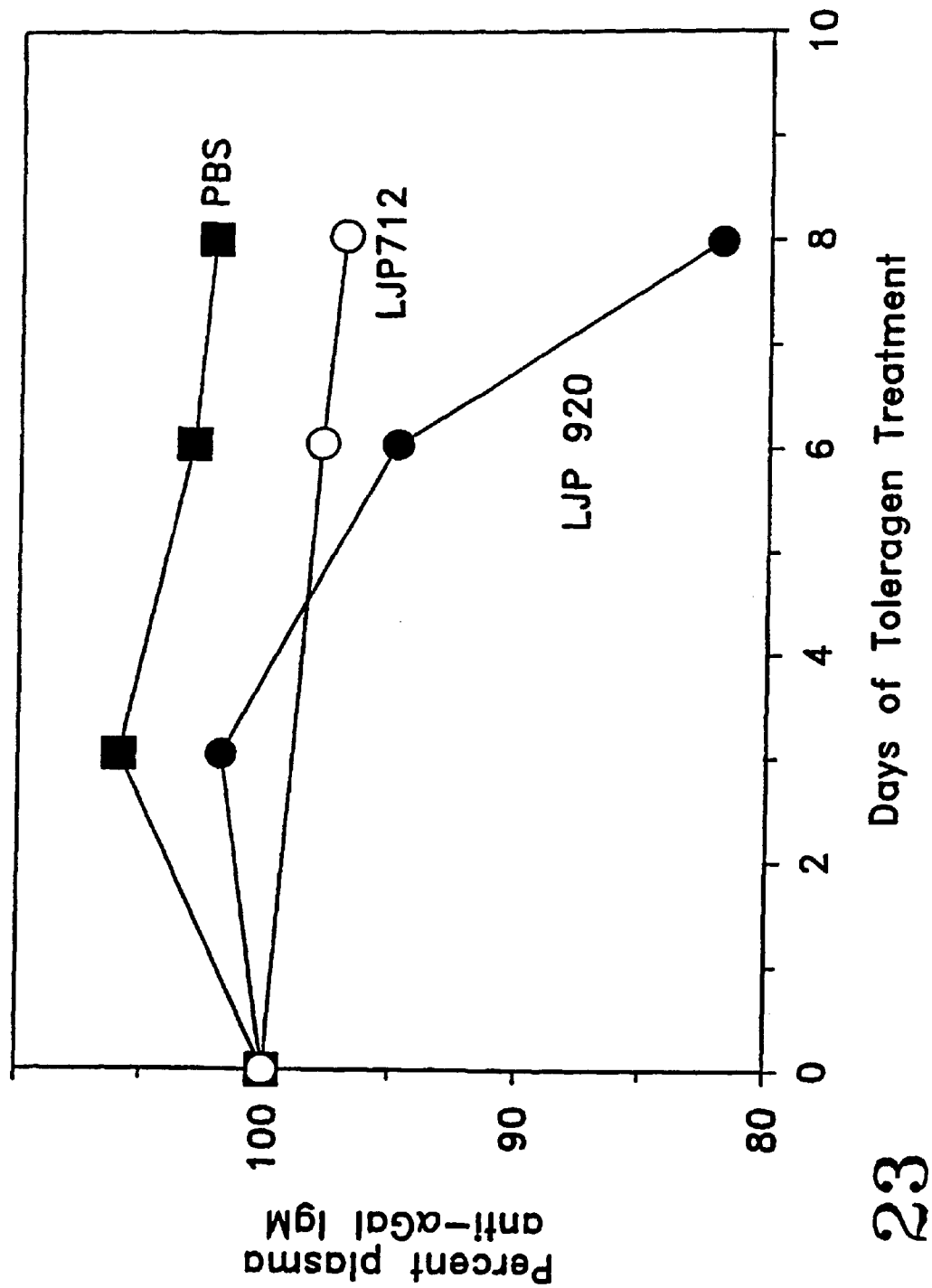
FIG. 23 is a graph comparing the effect of tetramer LJP 712 (open circles) with octamer LJP 920 (solid circles) on the percent plasma anti-αGal IgM, as described in Example 5. PBS (solid squares) was included as a negative control.

We next determined whether treatment of rhesus monkeys for 7 days with the octameric toleragen LJP 920 led to a diminution in serum levels of anti-αGal Ab. Two monkeys were treated IV daily with PBS and two were treated IV daily with LJP 920 (cpd 46) at 20 mg/kg, a dose which for tetrameric toleragen had shown a diminution in circulating IgG anti-αGal but not IgM anti-αGal. Serum samples were prepared from blood drawn immediately prior to drug or control administration on day 0 (prebleed) and on days 3 and 6 (24 hours post-drug administration). Serum was also prepared on day 8, 24 hours after the last dose with no subsequent dosing administered. LJP 920 (cpd 46) was well-tolerated in the treated animals with no untoward effects as observed by veterinary staff. At day 8, IgG anti-αGal levels were decreased by 11%, similar to the levels seen with tetramer. Control animals showed little change (FIG. 22A). Similarly, there was a diminution of 18% in IgM anti-αGal levels in one monkey and 5% in the replicate animal. By contrast, IgM anti-αGal levels in the control animals did not change in one animal and increased in the replicate animal, as shown in FIG. 22B. That the octamer is more efficient than tetramer at clearing IgM anti-αGal is shown in FIG. 23. These data show that increased valency results not only in a more efficacious molecule in vitro but also in vivo.

Example 6

In Vivo Evaluation of Octameric Conjugate: Induction of Tolerance gal α1,3-galactosyltransferase Knockout Mice using an Octameric Gal α1-3Gal Conjugate, LJP 920

The goal of this experiment was to determine whether treatment of GalT knock-out mice with octameric digal (used interchangeably with αGal) conjugate LJP 920 would induce digal (i.e., αGal)-specific tolerance.

α1,3-galactosyltransferase knockout mice (Thall et al. (1995) *J. Biol. Chem.* 270:21437–21440) (GalT KO) are unable to synthesize the Galα1α1-3Gal disaccharide (digal.) and as such are similar to humans, apes and Old world monkeys in that they spontaneously form antibodies that recognize terminal Galα1-3Gal epitopes. The GalT KO mouse therefore is an extremely useful system in which to test potential methods of diminishing natural anti-Galα1-3Gal antibodies. Yang et al. (1998) *J. Exp. Med.* 187:1335–1342.

Materials and Methods

ELISA for anti αGal antibody. Immunoassay plates (Costar #3590) were coated overnight at 4° C. with 100 μl/well digal (i.e., αGal)-bovine serum albumin (BSA-digal) at 5 μg/ml in phosphate buffered saline (PBS). Plates were washed with PBS and remaining protein-binding sites blocked overnight at 4° C. with 250 μl/well 5% non-fat dried milk in PBS. Serum samples were diluted in Hanks Balanced salt solution (HBSS) containing 0.5% BSA (HBSA). Blocked plates were washed with PBS-0.1% Tween 20 and 50 μl of serum sample dilutions added. Plates were incubated for 1 hour at room temperature. Plates were washed with PBS-0.1% Tween 20. Alkaline phosphatase-conjugated goat anti-mouse IgG or IgM (Jackson #115-055-146 or 115-055-075, 1/1000 in HBSA) was added (100 μl/well) and plates were incubated for 1 hour at room temperature. Plates were washed with PBS-0.1% Tween 20. Phenolphthalein monophosphate (1:26 in distilled water, 100 μl per well) was added and the plates incubated at room temperature. Optical density was read at 550 nm after 10 and 30 minutes incubation on a PowerWave 340 Microplate spectrophotometer.

ELISpot for anti-digal specific antibody forming cells. Immunoassay plates were coated with BSA-digal and blocked as above. Blocked plates were washed 6× with PBS-0.1% Tween 20, 2× with PBS and once with RPMI-1640 (Sigma) containing 1% fetal bovine serum (FBS, Gibco #16000-044), 2 mM glutamine (Gibco #25030-081), 1× antibiotics (Gibco #15240-062) and 10 mM HEPES (Gibco #15630-080) (RPMI-1). Spleens were removed from mice and disaggregated into RPMI-1 by crushing between two ground glass slides. Peritoneal cells were obtained by washing the peritoneal cavity with RPMI-1. Cells were washed two times in RPMI-1 and resuspended in the same medium containing 10% FBS (RPMI-10). Dilutions of cells were plated onto coated plates in a final volume of 100 μl RPMI-10. Plates were incubated overnight at 37° C. in 5% $CO_2$, 95% humidity.

Plates were washed 6× with PBS-0.1% Tween 20 and incubated with 100 μl biotin-conjugated anti-IgM or anti-IgG (Jackson #115-065-020 or 115-065-008, 1/1000 in PBS containing 10% goat serum, 1% fish gelatin and 0.05% Tween-20) for 1 hour at 37° C. Plates were washed 6× with PBS-0.1% Tween 20 and incubated with 100 μl ExtrAvidin-alkaline phosphatase (Sigma, #E2636, 1/1000 in PBS containing 10% goat serum, 1% fish gelatin and 0.05% Tween-20) for 1 hour at 37° C. Plates were washed 6× with PBS-0.1% Tween 20 and incubated with 100 μl alkaline phosphatase substrate B, 1/100 in developing buffer (Biorad #170-6432) overnight at room temperature in the dark. Plates were then rinsed with distilled water, air-dried, and spots counted manually by microscopic examination.

Experimental protocol. GalT KO mice were obtained from John Lowe (University of Michigan). Mice (15–16 weeks old) were treated daily (excluding Sundays) for 15 weeks i.p. with 400 μg LJP 920 dissolved in phosphate buffered saline (PBS) or PBS alone. Blood samples were collected prior to treatment and weekly thereafter. After 15 weeks LJP 920 treatment was halted and mice were immunized with $1 \times 10^9$ rabbit red blood cells (rRBC) i.p. Immunization was necessary for the detection of anti-digal specific antibody forming cells (AFC) and allowed determination of whether tolerance had been induced. Eight days later animals were sacrificed and spleen and peritoneal cells assayed for digal-specific AFC by ELISpot. Serum samples were assayed for anti-digal-antibodies by ELISA. For comparison, wild type C57B1/6×DBA/2 mice were also tested. These mice express the α1,3-galactosyltransferase enzyme and so do not make anti-digal antibodies. Values from these mice represent background in ELISA assays.

Results

Figure 27A:
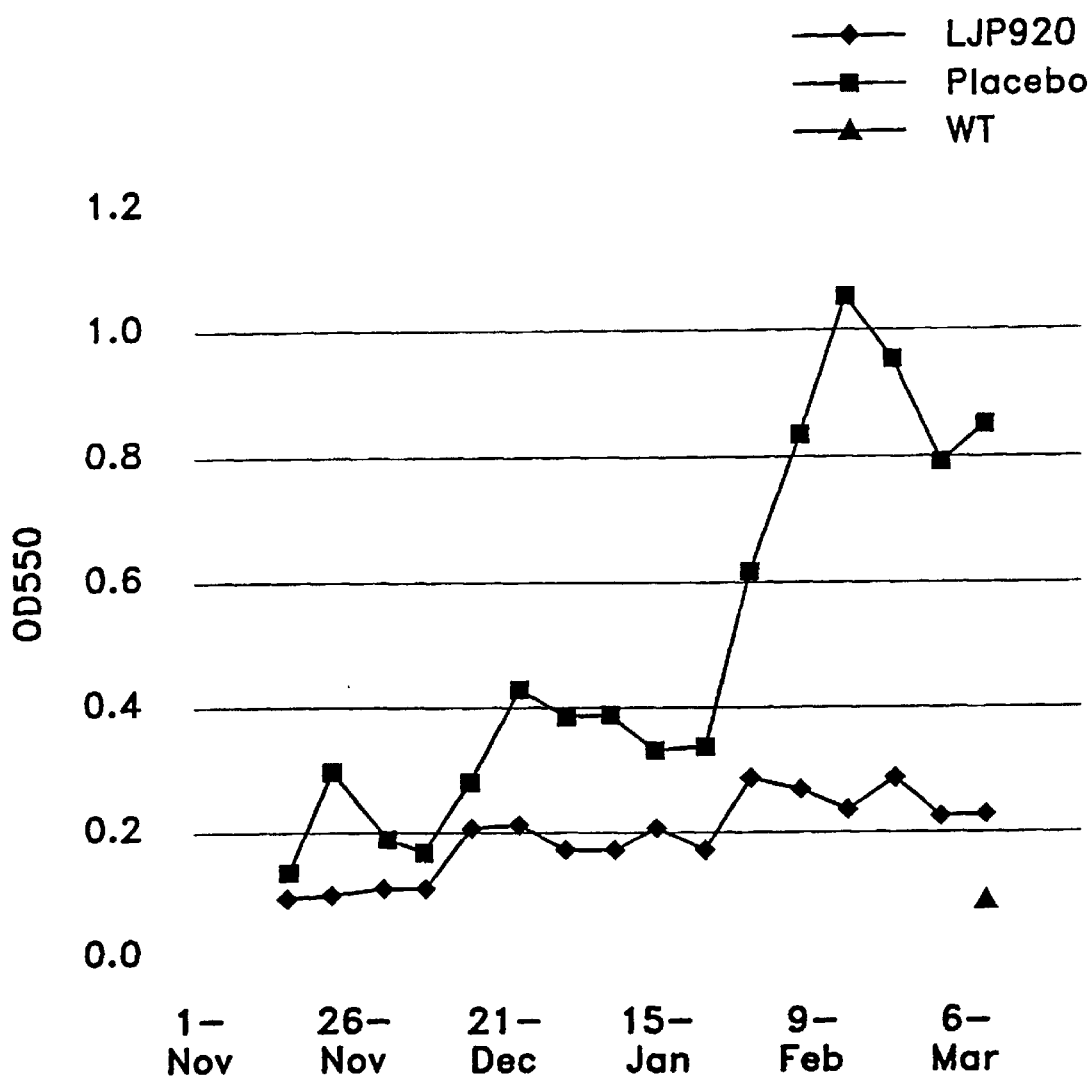
FIGS. 27A and 27B are graphs depicting the decrease in anti-αGal IgM (27A) and IgG (27B) following treatment in GalT knock-out mice with octameric conjugate LJP 920 (diamonds), compared with PBS (squares), as described in Example 6.
Figure 27B:
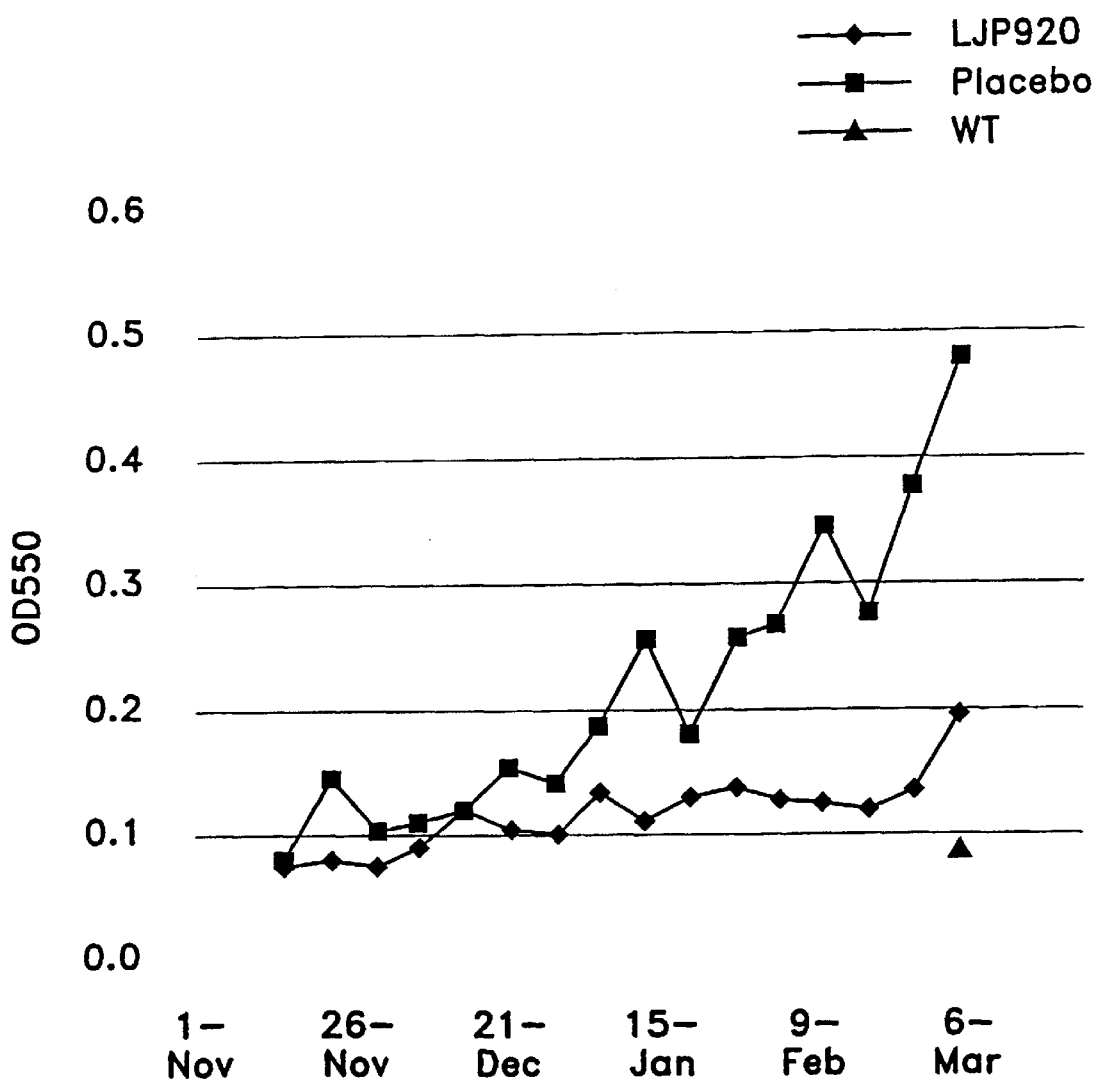

Serum anti-digal antibody levels. Data from sequential bleeds were analyzed by repeated measures ANOVA. IgM and IgG anti-digal antibodies were significantly reduced in LJP 920 treated animals relative to placebo treated animals ($p \leq 0.001$ in both cases; FIGS. 27A and 27B).

Figure 28A:
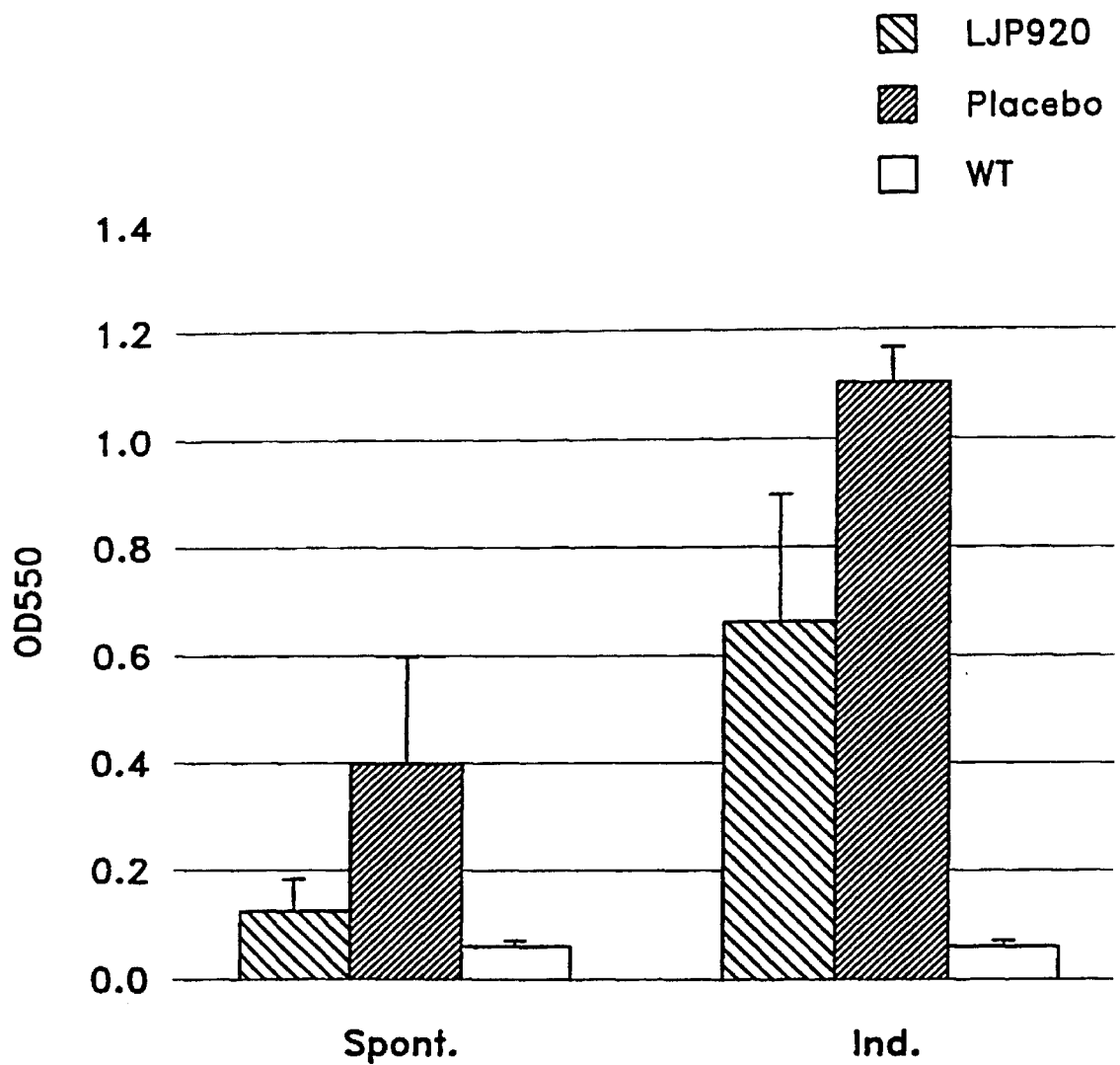
FIGS. 28A and 28B are bar graphs depicting the decrease in spontaneous and rRBC-induced anti-αGal IgM (28A) and IgG (28B) following treatment in GalT knock-out mice with octameric LJP 920 (left bar), compared with PBS (middle bar), as described in Example 6. Wild-type levels are shown in the right bar.
Figure 28B:
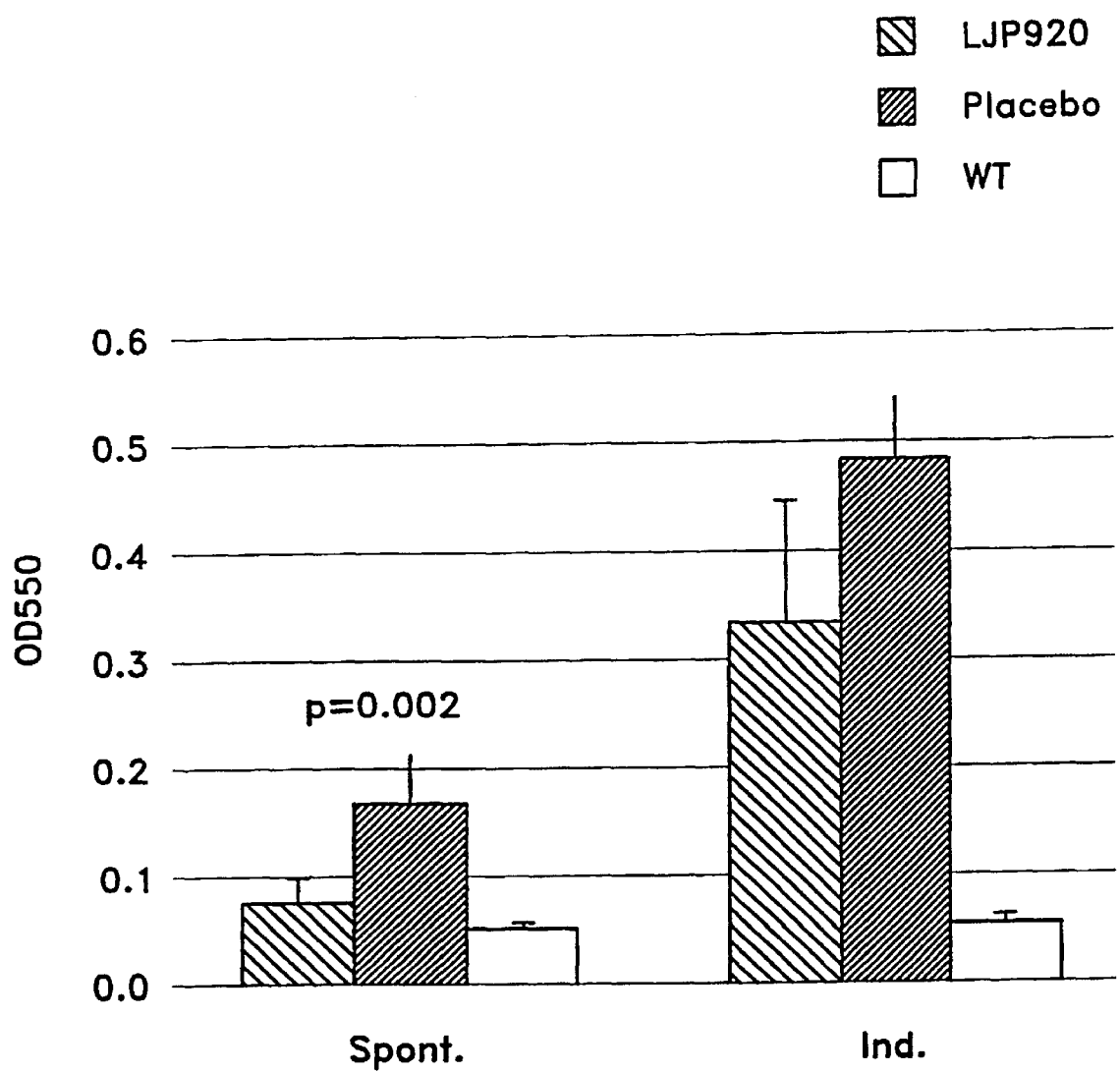

At 15 weeks, prior to rRBC immunization, levels of IgM anti-digal antibodies were significantly decreased in LJP 920 treated animals relative to placebo treated animals (mean OD 0.124 vs 0.399, p=0.0004, ANOVA; FIG. 28A). Similarly, levels of IgG anti-digal antibodies were significantly decreased in LJP 920 treated animals relative to placebo treated animals (mean OD 0.079 vs 0.179, p=0.0005, ANOVA; FIG. 28B). In LJP 920 treated animals, levels of IgM and IgG anti-digal were not significantly different from background (IgM: WT, mean OD 0.061 vs LJP 920, mean OD 0.124; IgG: WT, mean OD 0.055 vs LJP 920, mean OD 0.079; FIGS. 28A and B).

Following immunization with rRBC, levels of IgM anti digal antibodies were significantly lower in LJP 920 treated animals vs. placebo treated animals (LJP 920 mean OD 0.658 vs placebo mean 1.097, p=0.008, ANOVA; FIG. 28A). Levels of IgG anti-digal antibodies were similarly lower in LJP 920 treated animals (LJP 920 mean OD 0.335 vs placebo mean 0.481, p=0.038, ANOVA; FIG. 28B). Both IgM and IgG anti-digal antibody levels in LJP 920 treated animals were significantly increased following rRBC immunization relative to WT controls however (IgM: WT, mean OD 0.062 vs LJP 920, mean OD 0.658, p=0.001; IgG: WT, mean OD 0.058 vs LJP 920, mean OD 0.335, p=0.001, ANOVA; FIGS. 28A and B).

Figure 29:
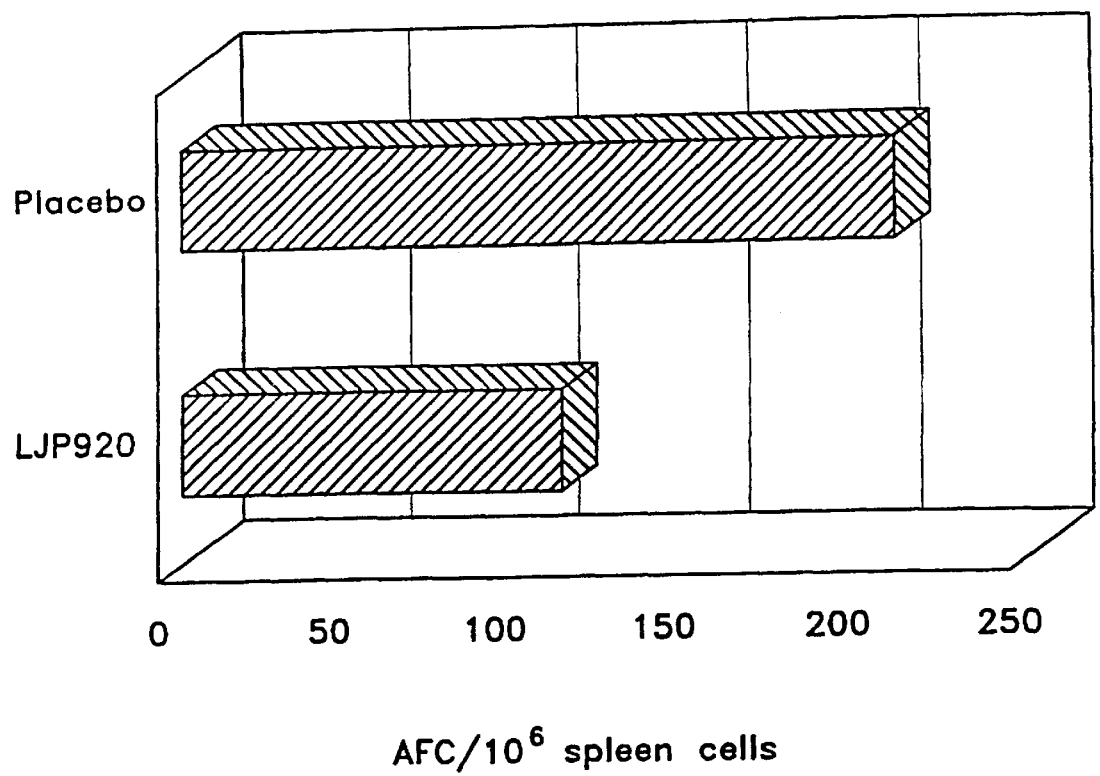
FIG. 29 is a bar graph depicting the decrease in IgM anti-αGal antibody forming cells in GalT knock-out mice treated with octameric LJP 920 compared with PBS as described in Example 6.

Digal-specific AFC. The frequency of digal-specific AFC following rRBC immunization was determined by ELISpot analysis. IgM anti-digal AFC were significantly lower in LJP 920 treated animals compared with placebo treated animals (p=0.02, ANOVA; FIG. 29); however the number of AFC did not decrease to background levels. Neither anti-digal-specific AFC in peritoneal cells nor IgG anti-digal. secreting cells in the spleen were detected.

These results indicate that treatment with LJP920 is highly effective at decreasing the level of both IgM and IgG anti-αGal antibodies. That this result reflects tolerance induced by the toleragen is supported by the observation of a significant decrease in αGal-specific AFC following LJP920 treatment.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

We claim:

1. A conjugate comprising a valency platform molecule and an αGal epitope, wherein the valency platform molecule is

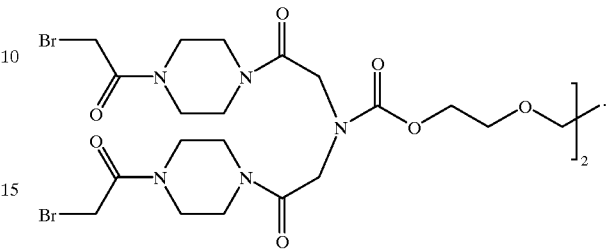

2. A conjugate comprising a valency platform molecule and an αGal epitope, wherein the valency platform molecule is

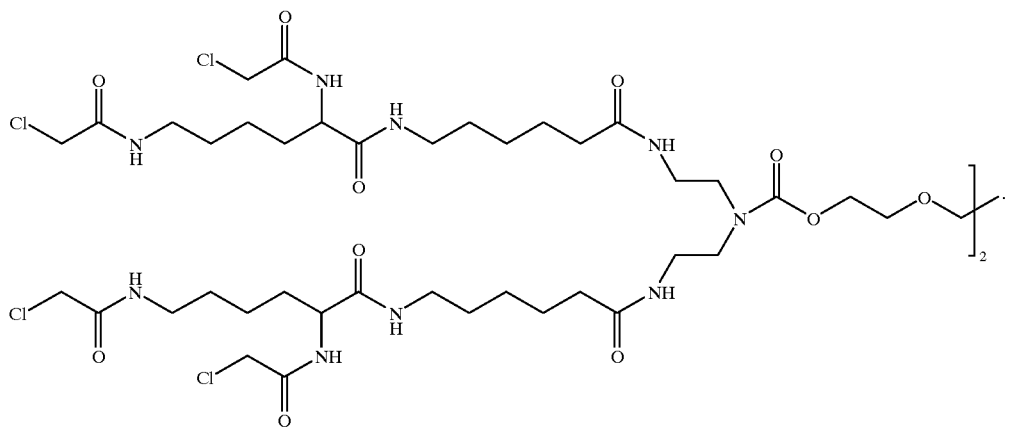

3. A conjugate according to claim 1, wherein the conjugate has the structure of

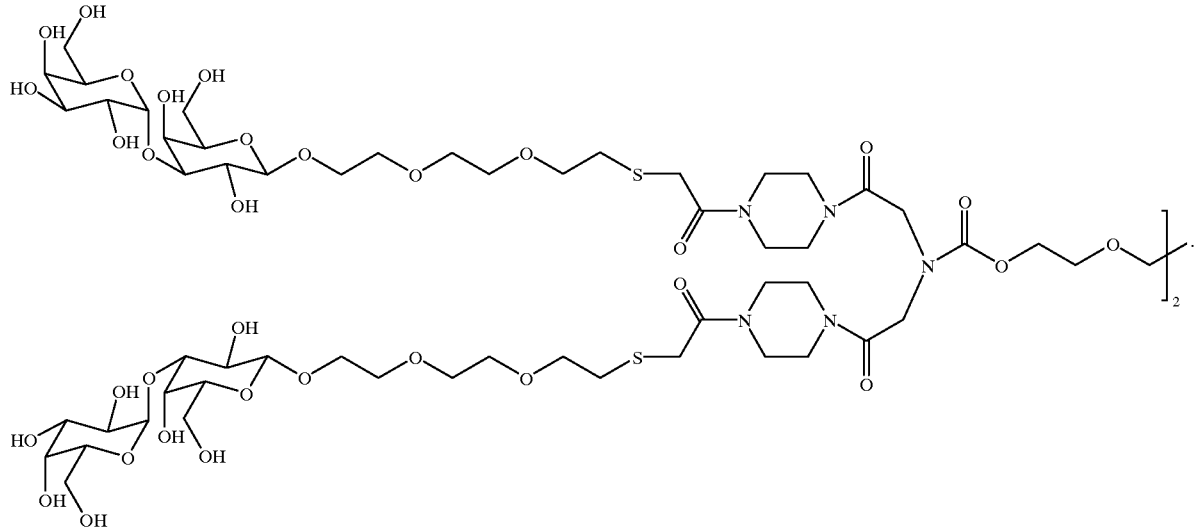

4. A conjugate according to claim 2, wherein the conjugate has the structure of

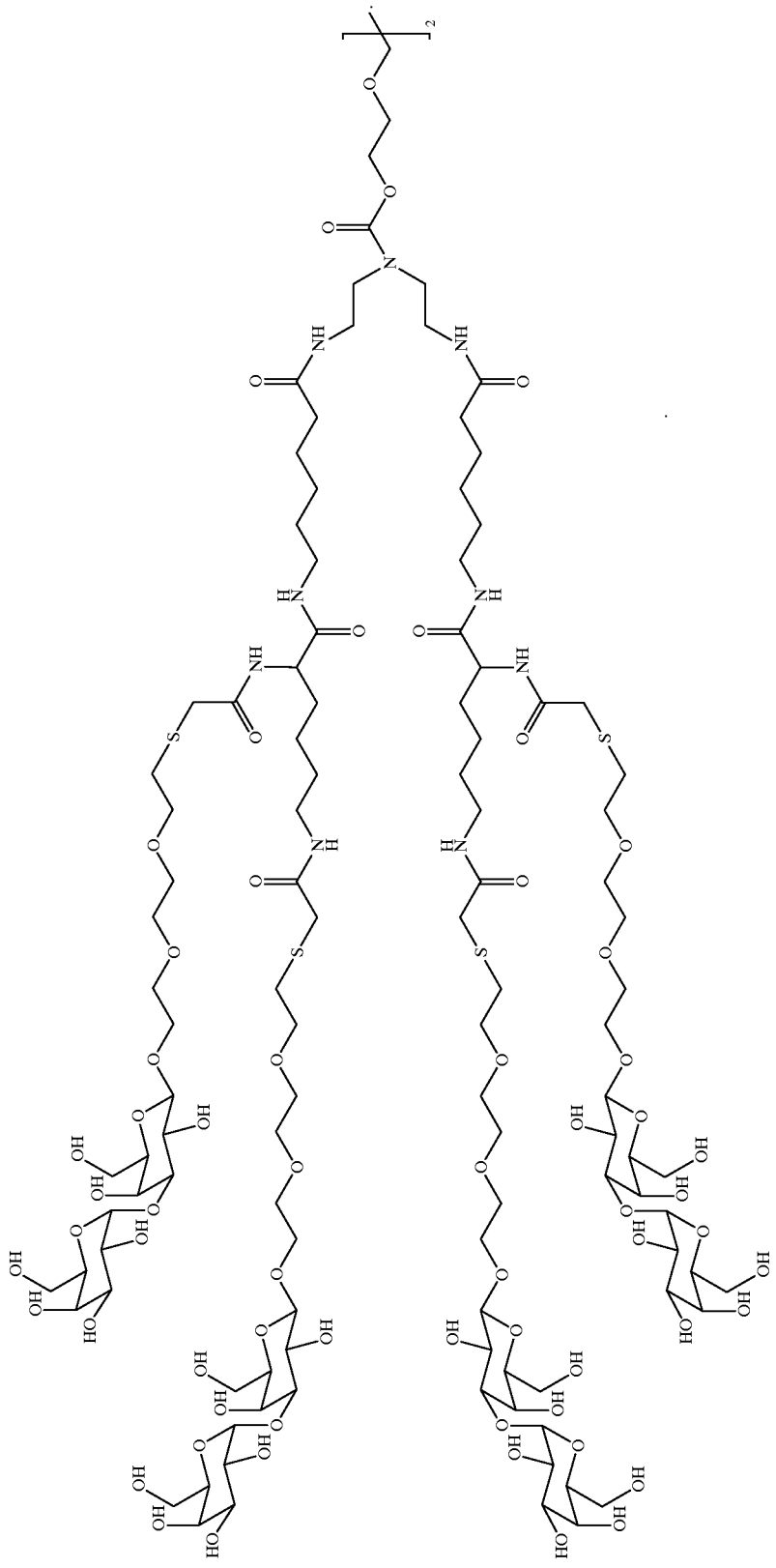

5. A composition comprising the conjugate of claim 3, and a pharmaceutically acceptable excipient.

6. A composition comprising the conjugate of claim 4, and a pharmaceutically acceptable excipient.

7. A method of reducing circulating levels of anti-αGal antibody in an individual, comprising administering the conjugate of claim 2 to the individual in an amount sufficient to induce tolerance to αGal in the individual.

8. A method of reducing circulating levels of anti-αGal antibody in an individual, comprising administering the conjugate of claim 4 to the individual in an amount sufficient to reduce circulating levels of anti-αGal antibody in the individual.

9. A method of inducing tolerance to αGal in an individual, comprising administering the conjugate of claim 4 to the individual in an amount sufficient to induce tolerance to αGal in the individual.

10. A method of performing a xenotransplantation in an individual, comprising the steps of:
    (a) introducing xenotissue to an individual, wherein the xenotissue comprises an αGal epitope; and
    (b) administering the conjugate of claim 3 to the individual.

11. The method of claim 10, wherein step (b) is performed at least about 30 days before step (a).

12. A method of performing a xenotransplantation in an individual, comprising the steps of:
    (a) introducing xenotissue to an individual, wherein the xenotissue comprises an αGal epitope; and
    (b) administering the conjugate of claim 4 to the individual.

13. The method of claim 12, wherein step (b) is performed at least about 30 days before step (a).

14. A conjugate comprising a valency platform molecule and an αGal epitope, wherein the valency platform molecule is

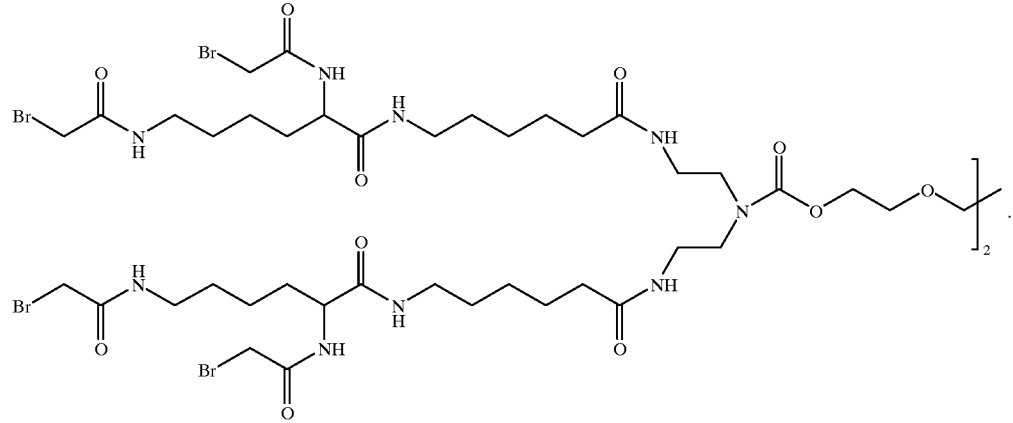

15. A composition comprising the conjugate of claim 14, and a pharmaceutically-acceptable excipient.

16. A method of reducing circulating levels of anti-αGal antibody in an individual, comprising administering the conjugate of claim 1 to the individual in an amount sufficient to reduce circulating levels of anti-αGal antibody in the individual.

17. A method of reducing circulating levels of anti-αGal antibody in an individual, comprising administering the conjugate of claim 2 to the individual in an amount sufficient to reduce circulating levels of anti-αGal antibody in the individual.

18. A method of reducing circulating levels of anti-αGal antibody in an individual, comprising administering the conjugate of claim 14 to the individual in an amount sufficient to reduce circulating levels of anti-αGal antibody in the individual.

19. A method of inducing tolerance to αGal in an individual, comprising administering the conjugate of claim 1 to the individual in an amount sufficient to induce tolerance to αGal in the individual.

20. A method of inducing tolerance to αGal in an individual, comprising administering the conjugate of claim 2 to the individual in an amount sufficient to induce tolerance to αGal in the individual.

21. A method of inducing tolerance to αGal in an individual, comprising administering the conjugate of claim 3 to the individual in an amount sufficient to induce tolerance to αGal in the individual.

22. A method of inducing tolerance to αGal in an individual, comprising administering the conjugate of claim 14 to the individual in an amount sufficient to induce tolerance to αGal in the individual.

* * * * *

UNITED STATES PATENT AND TRADEMARK OFFICE
CERTIFICATE OF CORRECTION

PATENT NO.   : 6,399,578 B1
DATED        : June 4, 2002
INVENTOR(S)  : Richard M. Jack et al.

It is certified that error appears in the above-identified patent and that said Letters Patent is hereby corrected as shown below:

<u>Column 44,</u>
Line 8, please delete "claim 2" and insert -- claim 3 --.

Signed and Sealed this

Fifteenth Day of October, 2002

*Attest:*

*Attesting Officer*

JAMES E. ROGAN
*Director of the United States Patent and Trademark Office*